US012781190B2

(12) United States Patent
Shusta et al.

(10) Patent No.: US 12,781,190 B2
(45) Date of Patent: Nov. 3, 2026

(54) METHOD FOR DIFFERENTIATION OF BRAIN MURAL CELLS FROM HUMAN PLURIPOTENT STEM CELLS

(71) Applicant: WISCONSIN ALUMNI RESEARCH FOUNDATION, Madison, WI (US)

(72) Inventors: Eric Shusta, Madison, WI (US); Benjamin Gastfriend, Madison, WI (US); Sean Palecek, Verona, WI (US)

(73) Assignee: Wisconsin Alumni Research Foundation, Madison, WI (US)

(*) Notice: Subject to any disclaimer, the term of this patent is extended or adjusted under 35 U.S.C. 154(b) by 354 days.

(21) Appl. No.: 17/933,730

(22) Filed: Sep. 20, 2022

(65) Prior Publication Data

US 2023/0089966 A1 Mar. 23, 2023

Related U.S. Application Data

(60) Provisional application No. 63/246,238, filed on Sep. 20, 2021.

(51) Int. Cl.
*C12N 5/071* (2010.01)
*C12N 15/86* (2006.01)

(52) U.S. Cl.
CPC ............ *C12N 5/069* (2013.01); *C12N 15/86* (2013.01); *C12N 2500/90* (2013.01); *C12N 2502/00* (2013.01); *C12N 2506/03* (2013.01); *C12N 2740/15043* (2013.01)

(58) Field of Classification Search
None
See application file for complete search history.

(56) References Cited

U.S. PATENT DOCUMENTS

| | | | | |
|---|---|---|---|---|
| 8,293,495 | B2 | 10/2012 | Shusta et al. | |
| 11,643,636 | B2 * | 5/2023 | Shusta | C12N 5/069 435/368 |
| 2014/0134732 | A1 | 5/2014 | Ashton et al. | |
| 2016/0032244 | A1 * | 2/2016 | Rusanescu | C12N 5/0618 435/377 |
| 2017/0025935 | A1 | 1/2017 | Pais | |
| 2019/0093084 | A1 | 3/2019 | Shusta et al. | |
| 2020/0017827 | A1 | 1/2020 | Shusta et al. | |

OTHER PUBLICATIONS

Miller, Sophie R., Surangi N. Perera, and Clare VH Baker. "Constitutively active Notch1 converts cranial neural crest-derived frontonasal mesenchyme to perivascular cells in vivo." Biology Open 6.3 (2017): 317-325. (Year: 2017).*

Aqvi, Sabia, Lena Dixit, and Krishnendu Roy. "Biomaterial-based notch signaling for the differentiation of hematopoietic stem cells into T cells." Journal of Biomedical Materials Research Part A:79.3 (2006): 689-697. (Year: 2006).*

Aihara, Yuko, et al. "Induction of neural crest cells from mouse embryonic stem cells in a serum-free monolayer culture." International Journal of Developmental Biology 54.8 (2010): 1287. (Year: 2010).*

Chen, Lijuan, et al. "The role of notch 1 activation in cardiosphere derived cell differentiation." Stem cells and development 21.12 (2012): 2122-2129. (Year: 2012).*

Schroeter, Eric H., Jeffrey A. Kisslinger, and Raphael Kopan. "Notch-1 signalling requires ligand-induced proteolytic release of intracellular domain." Nature 393.6683 (1998): 382-386. (Year: 1998).*

Sato, Yuki, et al. "Notch mediates the segmental specification of angioblasts in somites and their directed migration toward the dorsal aorta in avian embryos." Developmental cell 14.6 (2008): 890-901. (Year: 2008).*

Kisler, K. et al., Acute Ablation of Cortical Pericytes Leads to Rapid Neurovascular Uncoupling. Front. Cell. Neurosci. 14, 1-8 (2020).

Kisler, K. et al., Pericyte degeneration leads to neurovascular uncoupling and limits oxygen supply to brain. Nat. Neurosci. 20, 406-416 (2017).

Korn, J. et al., Neuroectodermal origin of brain pericytes and vascular smooth muscle cells. J. Comp. Neurol. 442, 78-88 (2002).

Kreitzer, et al., A robust method to derive functional neural crest cells from human pluripotent stem cells. Am. J. Stem Cells 2, 119-31 (2013).

Kubota, Y., H. K. Kleinman, G. R. Martin, T. J. Lawley, Role of laminin and basement membrane in the morphological differentiation of human endothelial cells into capillarylike structures. J. Cell Biol. 107, 1589-1598 (1988).

Kumar, A., et al., Specification and Diversification of Pericytes and Smooth Muscle Cells from Mesenchymoangioblasts. Cell Rep. 19, 1902-1916 (2017).

La Manno, et al., Molecular architecture of the developing mouse brain. bioRxiv (2020) https:/doi.org/10.1101/2020.07.02.184051.

La Manno, et al., Molecular Diversity of Midbrain Development in Mouse, Human, and Stem Cells. Cell 167, 566-580. e19 (2016).

Langmead, B., S. L. Salzberg, Fast gapped-read alignment with Bowtie 2. Nat. Methods 9, 357-359 (2012).

Langridge, P.D., G. Struhl, Epsin-Dependent Ligand Endocytosis Activates Notch by Force. Cell 171, 1383-1396.e12 (2017).

Le Lièvre, C.S., N. M. Le Douarin, Mesenchymal derivatives of the neural crest: analysis of chimaeric quail and chick embryos. J. Embryol. Exp. Morphol. 34, 125-154 (1975).

Lee, G., et al., Isolation and directed differentiation of neural crest stem cells derived from human embryonic stem cells. Nat. Biotechnol. 25 (2007).

Lehal, et al., Pharmacological disruption of the Notch transcription factor complex. Proc. Natl. Acad. Sci. U. S. A. 117, 16292-16301 (2020).

(Continued)

*Primary Examiner* — Tracy Vivlemore
*Assistant Examiner* — Fatimah Khalaf Matalkah
(74) *Attorney, Agent, or Firm* — Quarles & Brady LLP

(57) ABSTRACT

The present invention provides in vitro methods of differentiating brain mural cells and methods of use, including use in blood brain barrier models. Suitable in vitro derived cell populations of brain mural cells are also provided.

17 Claims, 35 Drawing Sheets
(35 of 35 Drawing Sheet(s) Filed in Color)
Specification includes a Sequence Listing.

(56) References Cited

OTHER PUBLICATIONS

Liao, Y., G. K. Smyth, W. Shi, FeatureCounts: An efficient general purpose program for assigning sequence reads to genomic features. Bioinformatics 30, 923-930 (2014).
Lilly, B., S. Kennard, Differential gene expression in a coculture model of angiogenesis reveals modulation of select pathways and a role for Notch signaling. Physiol. Genomics 36, 69-78 (2009).
Lindahl, P., B. R. Johansson, P. Levéen, C. Betsholtz, Pericyte loss and microaneurysm formation in PDGF-B-deficient mice. Science (80-. ). 277, 242-245 (1997).
Love, M.I, W. Huber, S. Anders, Moderated estimation of fold change and dispersion for RNA-seq data with DESeq2. Genome Biol. 15, 550 (2014).
Luo, et al., New developments on the Encyclopedia of DNA Elements (Encode) data portal. Nucleic Acids Res. 48, D882-D889 (2020).
Machanick, P., T. L. Bailey, MEME-ChIP: Motif analysis of large DNA datasets. Bioinformatics 27, 1696-1697 (2011).
Menendez, L., et al., Wnt signaling and a Smad pathway blockade direct the differentiation of human pluripotent stem cells to multipotent neural crest cells. Proc. Natl. Acad. Sci. 108, 19240-19245 (2011).
Montagne, et al., Pericyte degeneration causes white matter dysfunction in the mouse central nervous system. Nat. Med. 24, 326-337 (2018).
Nikolakopoulou, A.M. et al., Pericyte loss leads to circulatory failure and pleiotrophin depletion causing neuron loss. Nat. Neurosci. 22, 1089-1098 (2019).
Nishihara, et al., Intrinsic blood-brain barrier dysfunction contributes to multiple sclerosis pathogenesis. Brain (2022) https:/doi.org/10.1093/brain/awac019.
Nortley, R.et al., Amyloid β oligomers constrict human capillaries in Alzheimer's disease via signaling to pericytes. Science (80-. ). 365, eaav9518 (2019).
Patsch, et al., Generation of vascular endothelial and smooth muscle cells from human pluripotent stem cells. Nat. Cell Biol. 17, 994-1003 (2015).
Peppiatt, C.M., C. Howarth, P. Mobbs, D. Attwell, Bidirectional control of CNS capillary diameter by pericytes. Nature 443, 700-704 (2006).
Polioudakis, et al., A Single-Cell Transcriptomic Atlas of Human Neocortical Development during Mid-gestation. Neuron 103, 785-801.e8 (2019).
Ramírez, et al., deepTools2: a next generation web server for deep-sequencing data analysis. Nucleic Acids Res. 44, W160-W165 (2016).
Reyahi, et al., Foxf2 Is Required for Brain Pericyte Differentiation and Development and Maintenance of the Blood-Brain Barrier. Dev. Cell 34, 19-32 (2015).
Rungta, R.L., E. Chaigneau, B.-F. F. Osmanski, S. Charpak, Vascular Compartmentalization of Functional Hyperemia from the Synapse to the Pia. Neuron 99, 362-375.e4 (2018).
Shah, N.M., a K. Groves, D. J. Anderson, Alternative neural crest cell fates are instructively promoted by TGFbeta superfamily members. Cell 85, 331-43 (1996).
Siegenthaler, et al., Foxc1 is required by pericytes during fetal brain angiogenesis. Biol. Open 2, 647-659 (2013).
Soldatov, et al., Spatiotemporal structure of cell fate decisions in murine neural crest. Science (80-. ). 364, eaas9536 (2019).
Song, H.W., et al., Transcriptomic comparison of human and mouse brain microvessels. Sci. Rep. 10, 12358 (2020).
Stark, R., G. Brown, DiffBind: differential binding analysis of ChIP-Seq peak data.
Stebbins, M.J., et al., Human pluripotent stem cell-derived brain pericyte-like cells induce blood-brain barrier properties. Sci. Adv. 5, eaau7375 (2019).
Subramanian, et al., Gene set enrichment analysis: A knowledge-based approach for interpreting genome-wide expression profiles. Proc. Natl. Acad. Sci. 102, 15545-15550 (2005).
Sun, J., et al., Transplantation of hPSC-derived pericyte-like cells promotes functional recovery in ischemic stroke mice. Nat. Commun. 11 (2020).
Thomson, J.A., Embryonic stem cell lines derived from human blastocysts. Science (80-. ). 282, 1145-1147 (1998).
Vanlandewijck, et al., A molecular atlas of cell types and zonation in the brain vasculature. Nature 554, 475-480 (2018).
Wang, Y., L. Pan, C. B. Moens, B. Appel, Notch3 establishes brain vascular integrity by regulating pericyte number. Development 141, 307-317 (2014).
Wolf, F.A., P. Angerer, F. J. Theis, SCANPY: large-scale single-cell gene expression data analysis. Genome Biol. 19, 15 (2018).
Wurdak, H., Inactivation of TGFβ signaling in neural crest stem cells leads to multiple defects reminiscent of DiGeorge syndrome. Genes Dev. 19, 530-535 (2005).
Yamanishi E., M. Takahashi, Y. Saga, N. Osumi, Penetration and differentiation of cephalic neural crest-derived cells in the developing mouse telencephalon. Dev. Growth Differ. 54, 785-800 (2012).
Yang, et al., A human brain vascular atlas reveals diverse mediators of Alzheimer's risk. Nature 603, 885-892 (2022).
Yu G., L. G. Wang, Q. Y. He, ChIP seeker: An R/Bioconductor package for ChIP peak annotation, comparison and visualization. Bioinformatics 31, 2382-2383 (2015).
Yu, et al., Human Induced Pluripotent Stem Cells Free of Vector and Transgene Sequences. Science (80-. ). 324, 797-801 (2009).
Yu, et al., Induced pluripotent stem cell lines derived from human somatic cells. Science 318, 1917-20 (2007).
Zambach, et al., Precapillary sphincters and pericytes at first-order capillaries as key regulators for brain capillary perfusion. Proc. Natl. Acad. Sci. 118 (2021).
Zhang, et al., Model-based analysis of ChIP-Seq (MACS). Genome Biol. 9 (2008).
Zhong, et al., Decoding the development of the human hippocampus. Nature 577, 531-536 (2020).
Ziffra, et al., Single-cell epigenomics reveals mechanisms of human cortical development. Nature 598, 205-213 (2021).
Amemiya, H.M., A. Kundaje, A. P. Boyle, The Encode Blacklist: Identification of Problematic Regions of the Genome. Sci. Rep. 9, 1-5 (2019).
Ando, et al., KCNJ8/ABCC9-containing K-ATP channel modulates brain vascular smooth muscleneurovascular coupling. Dev. Cell, 1-17 (2022).
Ando, K., et al., Peri-arterial specification of vascular mural cells from naïve mesenchyme require Notch signaling. Development 146 (2019).
Armulik, A. et al., Pericytes regulate the blood-brain barrier. Nature 468, 557-561 (2010).
Armulik, A., A. Abramsson, C. Betsholtz, Endothelial/pericyte interactions. Circ. Res. 97, 512-523 (2005).
Armulik, A., G. Genové, C. Betsholtz, Pericytes: Developmental, Physiological, and Pathological Perspectives, Problems, and Promises. Dev. Cell 21, 193-215 (2011).
Ashburner, et al., Gene ontology: tool for the unification of biology. The Gene Ontology Consortium. Nat Genet. 25, 25-9 (2000).
Bell, R.D. et al., Apolipoprotein e controls cerebrovascular integrity via cyclophilin A. Nature 485, 512-516 (2012).
Bell, R.D. et al., Pericytes Control Key Neurovascular Functions and Neuronal Phenotype in the Adult Brain and during Brain Aging. Neuron 68, 409-427 (2010).
Bhattacharya, D., M. Rothstein, A. P. Azambuja, M. Simoes-Costa, Control of neural crest multipotency by Wnt signaling and the Lin28/let-7 axis. Elife 7, 1-24 (2018).
Blanchard, et al., Reconstruction of the human blood-brain barrier in vitro reveals a pathogenic mechanism of APOE4 in pericytes. Nat. Med. 26, 952-963 (2020).
Bray, S.J., M. Gomez-Lamarca, Notch after cleavage. Curr. Opin. Cell Biol. 51, 103-109 (2018).
Brown, L.A.; P. Sava, C. Garcia, A. L. Gonzalez, Proteomic Analysis of the Pericyte Derived Extracellular Matrix. Cell. Mol. Bioeng. 8, 349-363 (2015).
Castel, et al., Dynamic binding of RBPJ is determined by notch signaling status. Genes Dev. 27, 1059-1071 (2013).

(56) References Cited

OTHER PUBLICATIONS

Castro-Mondragon, et al., JASPAR 2022: The 9th release of the open-access database of transcription factor binding profiles. Nucleic Acids Res. 50, D165-D173 (2022).
Chen, et al., Chemically defined conditions for human iPSC derivation and culture. Nat. Methods 8, 424-9 (2011).
Chen, S., R. J. Lechleider, Transforming growth factor-beta-induced differentiation of smooth muscle from a neural crest stem cell line. Circ. Res. 94, 1195-202 (2004).
Cheung, C.; A. S. Bernardo, M. W. B. Trotter, R. A. Pedersen, S. Sinha, Generation of human vascular smooth muscle subtypes provides insight into embryological origin-dependent disease susceptibility. Nat. Biotechnol. 30, 165-173 (2012).
Cheung, C.; Y. T. Y. Y. T. Y. Y. T. Goh, J. Zhang, C. Wu, E. Guccione, Modeling cerebrovascular pathophysiology in amyloid-β metabolism using neural-crest-derived smooth muscle cells. Cell Rep. 9, 391-401 (2014).
Daneman, R., L. Zhou, A. A. Kebede, B. A. Barres, Pericytes are required for blood-brain barrier integrity during embryogenesis. Nature 468, 562-6 (2010).
Dobin, et al., STAR: Ultrafast universal RNA-seq aligner. Bioinformatics 29, 15-21 (2013).
Etchevers, H.C., C. Vincent, N. M. Le Douarin, G. F. Couly, The cephalic neural crest provides pericytes and smooth muscle cells to all blood vessels of the face and forebrain. Development 128, 1059-1068 (2001).
Etchevers, H.C., G. Couly, C. Vincent, N. M. Le Douarin, Anterior cephalic neural crest is required for forebrain viability. Development 126, 3533-43 (1999).
Everson, et al., Sonic hedgehog regulation of Foxf2 promotes cranial neural crest mesenchyme proliferation and is disrupted in cleft lip morphogenesis. Development 144, 2082-2091 (2017).
Faal, et al., Induction of Mesoderm and Neural Crest-Derived Pericytes from Human Pluripotent Stem Cells to Study Blood-Brain Barrier Interactions. Stem Cell Reports 12, 451-460 (2019).
Floy, et al., Developmental lineage of human pluripotent stem cell-derived cardiac fibroblasts affects their functional phenotype. FASEB J. 35, 1-23 (2021).
Garcia, et al., Single-cell dissection of the human brain vasculature. Nature 603, 893-899 (2022).
Gastfriend, B.D., K. L. Foreman, M. E. Katt, S. P. Palecek, E. V. Shusta, Integrative analysis of the human brain mural cell transcriptome. J. Cereb. Blood Flow Metab. 41, 3052-3068 (2021).
Gastfriend, B.D., M. J. Stebbins, F. Du, E. V. Shusta, S. P. Palecek, Differentiation of Brain Pericyte-Like Cells from Human Pluripotent Stem Cell-Derived Neural Crest. Curr. Protoc. 1, 1-32 (2021).
Gastfriend, B.D., S. P. Palecek, E. V Shusta, Modeling the blood-brain barrier: Beyond the endothelial cells. Curr. Opin. Biomed. Eng. 5, 6-12 (2018).
Gastfriend, et al., Wnt signaling mediates acquisition of blood-brain barrier properties in naïve endothelium derived from human pluripotent stem cells. Elife 10 (2021).
Ghosh, M. et al., Pericytes are involved in the pathogenesis of cerebral autosomal dominant arteriopathy with subcortical infarcts and leukoencephalopathy. Ann. Neurol. 78, 887-900 (2015).
Gonzales, et al., Contractile pericytes determine the direction of blood flow at capillary junctions. Proc. Natl. Acad. Sci. U. S. A. 117, 27022-27033 (2020).
Griffin, C., R. Bajpai, Neural Crest-Derived Human Cranial Pericytes Model Primary Forebrain Pericytes and Predict Disease-Specific Cranial Vasculature Defects. SSRN Electron. J. (2018) https:/doi.org/10.2139/ssrn.3189103.
Grubb, S. et al., Precapillary sphincters maintain perfusion in the cerebral cortex. Nat. Commun. 11, 395 (2020).
Hall, C.N. et al., Capillary pericytes regulate cerebral blood flow in health and disease. Nature 508, 55-60 (2014).
Halliday, M.R. et al., Accelerated pericyte degeneration and blood-brain barrier breakdown in apolipoprotein E4 carriers with Alzheimer's disease. J. Cereb. Blood Flow Metab. 36, 217-227(2016).
Han, et al., Construction of a human cell landscape at single-cell level. Nature 581, 303-309 (2020).
Hartmann, D.A. et al., Brain capillary pericytes exert a substantial but slow influence on blood flow. Nat. Neurosci. 24, 633-645 (2021).
Hartmann, D.A., V. Coelho-Santos, A. Y. Shih, Pericyte Control of Blood Flow Across Microvascular Zones in the Central Nervous System. Annu. Rev. Physiol. 84, 1-24 (2022).
He, et al., Analysis of the brain mural cell transcriptome. Sci. Rep. 6, 35108 (2016).
Hellström, M., M. Kalén, P. Lindahl, A. Abramsson, C. Betsholtz, Role of PDGF-B and PDGFR-beta in recruitment of vascular smooth muscle cells and pericytes during embryonic blood vessel formation in the mouse. Development 126, 3047-3055 (1999).
Hill, R.A et al., Regional Blood Flow in the Normal and Ischemic Brain Is Controlled by Arteriolar Smooth Muscle Cell Contractility and Not by Capillary Pericytes. Neuron 87, 95-110 (2015).
Hirschi, K.K., S. A. Rohovsky, P. A. D'Amore, PDGF, TGF-beta, and heterotypic cellcell interactions mediate endothelial cell-induced recruitment of 10T1/2 cells and their differentiation to a smooth muscle fate. J. Cell Biol. 141, 805-814 (1998).
Hodge, et al., Conserved cell types with divergent features in human versus mouse cortex. Nature 573, 61-68 (2019).
Hosford, P.S. et al., A critical role for the ATP-sensitive potassium channel subunit KIR6.1 in the control of cerebral blood flow. J. Cereb. Blood Flow Metab. 39, 2089-2095 (2019).
Jiang, X., S. Iseki, R. E. Maxson, H. M. Sucov, G. M. Morriss-Kay, Tissue Origins and Interactions in the Mammalian Skull Vault. Dev. Biol. 241, 106-116 (2002).
Joutel, A. et al., The ectodomain of the Notch3 receptor accumulates within the cerebrovasculature of CADASIL patients. J. Clin. Invest. 105, 597-605 (2000).
Kanehisa, M., S. Goto, KEGG: kyoto encyclopedia of genes and genomes. Nucleic Acids Res. 28, 27-30 (2000).
Kent, et al., The Human Genome Browser at UCSC. Genome Res. 12, 996-1006 (2002).

* cited by examiner

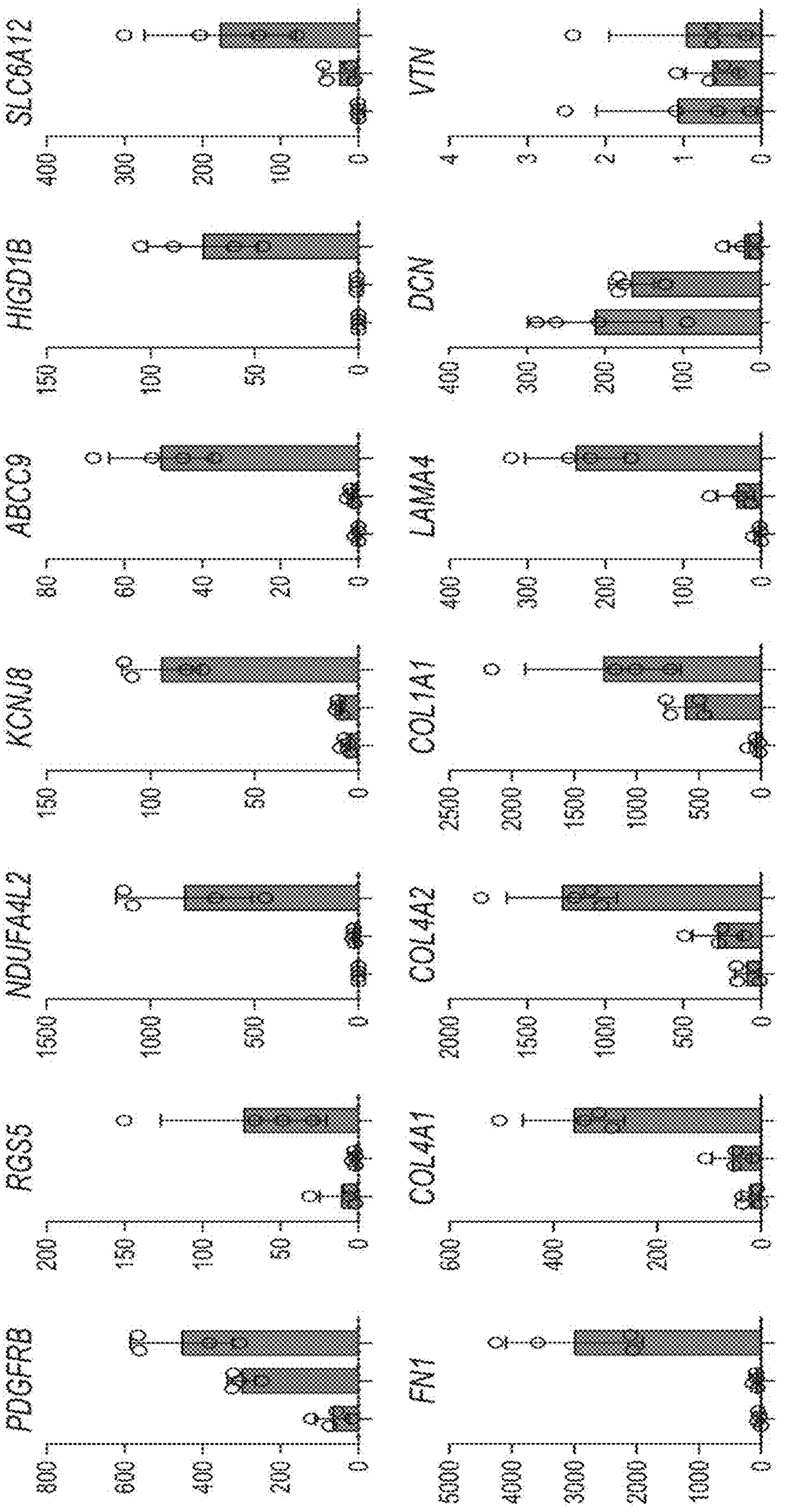
Figure 3 panel E continued

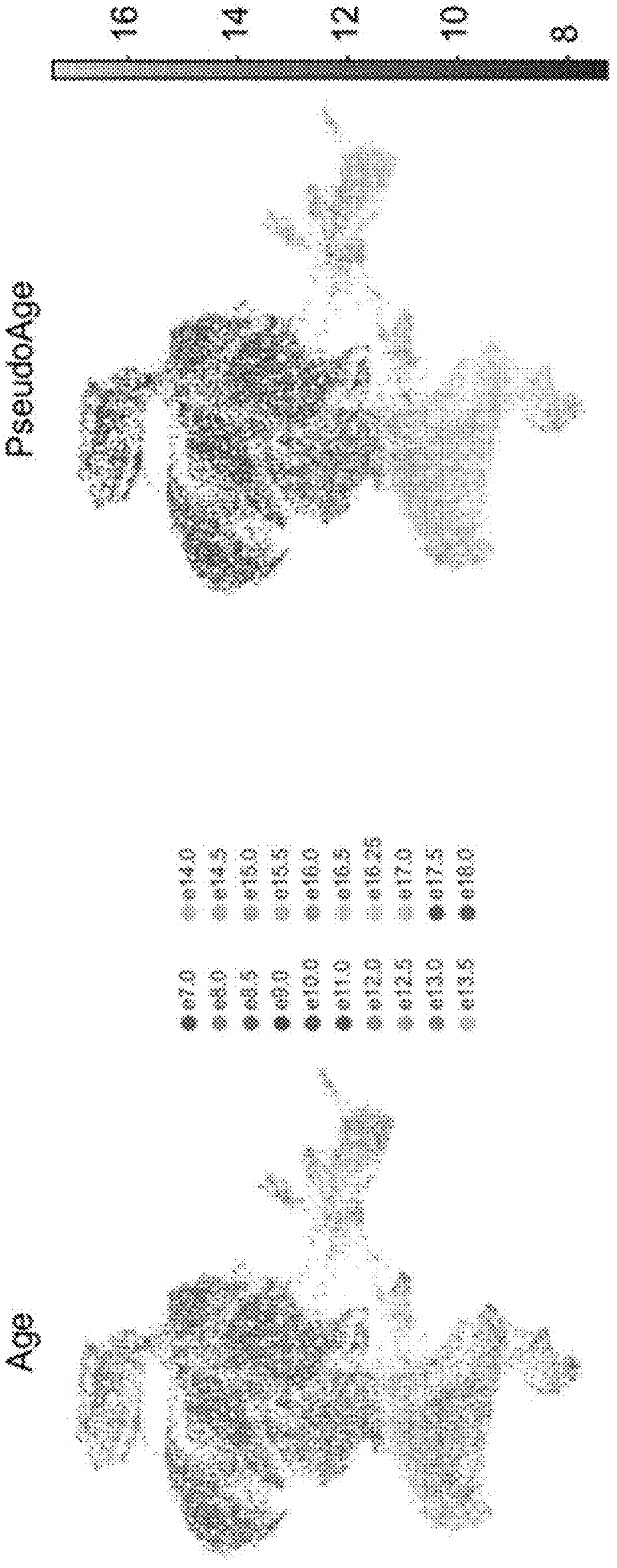
Figure 7 Panel A Continued

C

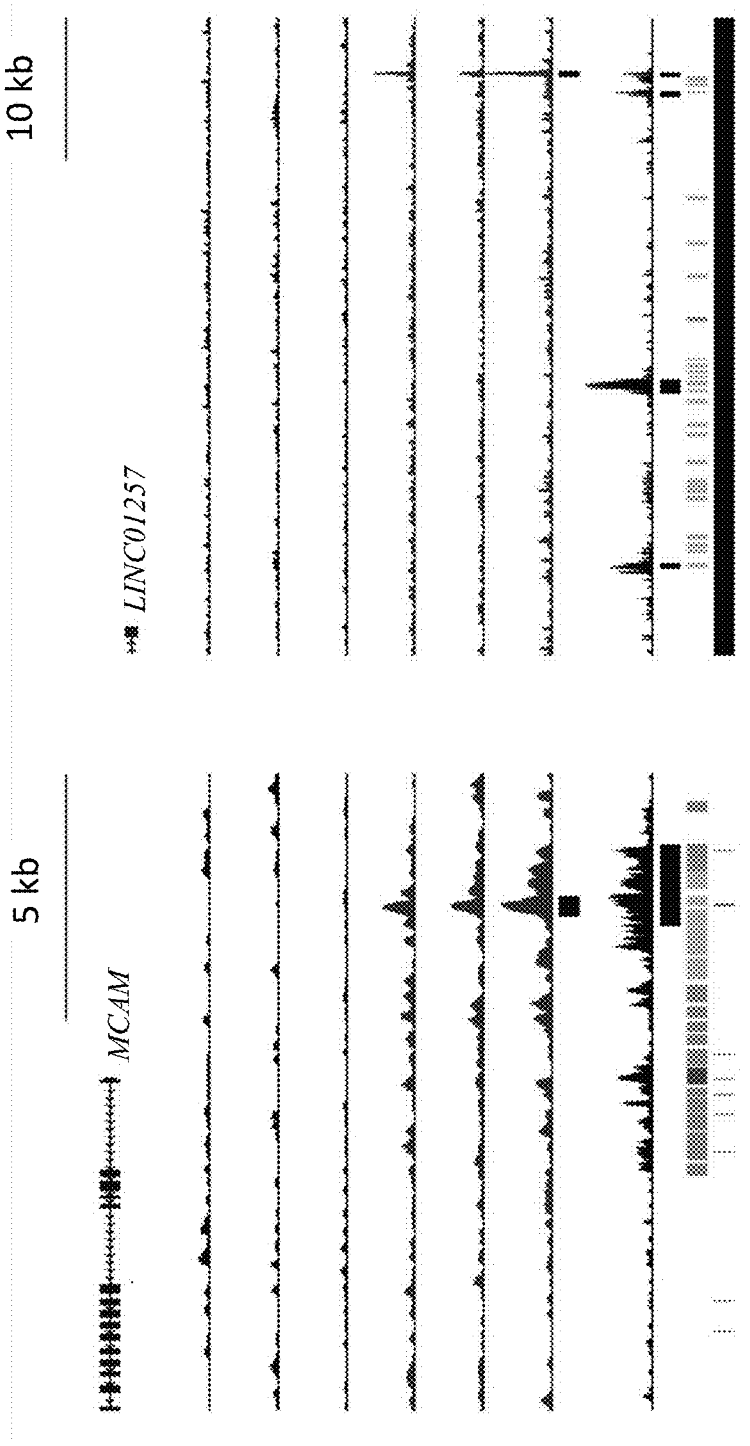
Figure 16 part B continued

SEQUENCE LISTING

```
Sequence total quantity: 44
SEQ ID NO: 1            moltype = DNA  length = 1986
FEATURE                 Location/Qualifiers
source                  1..1986
                        mol_type = other DNA
                        organism = synthetic construct
SEQUENCE: 1
atggtcatgg tggcccggcg caagcgcgag cacagcaccc tctggttccc tgagggcttc  60
tcactgcaca aggacgtggc ctctggtcac aagggccggc gggaacccgt gggccaggac  120
gcgctgggca tgaagaacat ggccaagggt gagagcctga tgggggaggt ggccacagac  180
tggatggaca cagagtgccc agaggccaag cggctaaagg tagaggagcc aggcatgggg  240
gctgaggagg ctgtggattg ccgtcagtgg actcaacacc atctggttgc tgctgacatc  300
cgcgtggcac cagccatggc actgacacca ccacagggcg acgcagatgc tgatggcatg  360
gatgtcaatg tgcgtggccc agatggcttc accccgctaa tgctggcttc cttctgtggg  420
ggggctctgg agccaatgcc aactgaagag gatgaggcag atgacacatc agctagcatc  480
atctccgacc tgatctgcca gggggctcag cttggggcac ggactgaccg tactggcgag  540
actgctttgc acctggctgc ccgttatgcc cgtgctgatg cagccaagcg gctgctggat  600
gctggggcag acaccaatgc ccaggaccac tcaggccgca ctcccctgca cacagctgtc  660
acagccgatg cccagggtgt cttccagatt ctcatccgaa accgctctac agacttggat  720
gcccgcatgg cagatggctc aacggcactg atcctggcgg cccgcctggc agtagagggc  780
atggtggaag agctcatcgc cagccatgct gatgtcaatg ctgtggatga gcttgggaaa  840
tcagccttac actgggctgc ggctgtgaac aacgtggaag ccactttggc cctgctcaaa  900
aatggagcca ataaggacat gcaggatagc aaggaggaga ccccccctatt cctggccgcc  960
cgcgagggca gctatgaggc tgccaagctg ctgttggacc actttgccaa ccgtgagatc  1020
accgaccacc tggacaggct gccgcgggac gtagcccagg agagactgca ccaggacatc  1080
gtgcgcttgc tggatcaacc cagtgggccc cgcagccccc ccggtcccca cggcctgggg  1140
cctctgctct gtcctccagg ggccttcctc cctggcctca aagcggcaca gtcggggtcc  1200
aagaagagca ggaggccccc cgggaaggcg gggctggggc cgcaggggcc ccgggggcgg  1260
ggcaagaagc tgacgctggc ctgcccgggc cccctggctg acagctcggt cacgctgtcg  1320
cccgtggact cgctggactc cccgcggcct ttcggtgggc cccctgcttc ccctggtggc  1380
ttccccccttg aggggcccta tgcagctgcc actgccactg cagtgtctct ggcacagctt  1440
ggtggcccag gccgggcggg tctagggcgc cagccccctg gaggatgtgt actcagcctg  1500
ggcctgctga accctgtggc tgtgcccctc gattgggccc ggctgccccc acctgcccct  1560
ccaggcccct cgttcctgct gccactggcg ccgggacccc agctgctcaa cccagggacc  1620
cccgtctccc cgcaggagcg gcccccgcct tacctggcag tcccaggaca tggcgaggag  1680
tacccggcgg ctggggcaca cagcagcccc ccaaaggccc gcttcctgcg ggttcccagt  1740
gagcaccctt acctgacccc atcccccgaa tcccctgagc actgggccag cccctcacct  1800
ccctccctct cagactggtc cgaatccacg cctagcccag ccactgccac tggggccatg  1860
gccaccacca ctggggcact gcctgcccag ccacttccct tgtctgttcc cagctccctt  1920
```

```
gctcaggccc agacccagct ggggccccag ccggaagtta cccccaagag gcaagtgttg  1980
gcctga                                                             1986

SEQ ID NO: 2           moltype = AA  length = 661
FEATURE                Location/Qualifiers
source                 1..661
                       mol_type = protein
                       organism = synthetic construct
SEQUENCE: 2
MVMVARRKRE HSTLWFPEGF SLHKDVASGH KGRREPVGQD ALGMKNMAKG ESLMGEVATD  60
WMDTECPEAK RLKVEEPGMG AEEAVDCRQW TQHHLVAADI RVAPAMALTP PQGDADADGM  120
DVNVRGPDGF TPLMLASFCG GALEPMPTEE DEADDTSASI ISDLICQGAQ LGARTDRTGE  180
TALHLAARYA RADAAKRLLD AGADTNAQDH SGRTPLHTAV TADAQGVFQI LIRNRSTDLD  240
ARMADGSTAL ILAARLAVEG MVEELIASHA DVNAVDELGK SALHWAAAVN NVEATLALLK  300
NGANKDMQDS KEETPLFLAA REGSYEAAKL LLDHFANREI TDHLDRLPRD VAQERLHQDI  360
VRLLDQPSGP RSPPGPHGLG PLLCPPGAFL PGLKAAQSGS KKSRRPPGKA GLGPQGPRGR  420
GKKLTLACPG PLADSSVTLS PVDSLDSPRP FGGPPASPGG FPLEGPYAAA TATAVSLAQL  480
GGPGRAGLGR QPPGGCVLSL GLLNPVAVPL DWARLPPPAP PGPSFLLPLA PGPQLLNPGT  540
PVSPQERPPP YLAVPGHGEE YPAAGAHSSP PKARFLRVPS EHPYLTPSPE SPEHWASPSP  600
PSLSDWSEST PSPATATGAM ATTTGALPAQ PLPLSVPSSL AQAQTQLGPQ PEVTPKRQVL  660
A                                                                  661

SEQ ID NO: 3           moltype = DNA  length = 2412
FEATURE                Location/Qualifiers
source                 1..2412
                       mol_type = other DNA
                       organism = synthetic construct
SEQUENCE: 3
atggtgctgc tgtcccgcaa gcgccggcgg cagcatggcc agctctggtt ccctgagggc  60
ttcaaagtgt ctgaggccag caagaagaag cggcgggagc ccctcggcga ggactccgtg  120
ggcctcaagc ccctgaagaa cgcttcagac ggtgccctca tggacgacaa ccagaatgag  180
tggggggacg aggacctgga gaccaagaag ttccggttcg aggagcccgt ggttctgcct  240
gacctggacg accagacaga ccaccggcag tggactcagc agcacctgga tgccgctgac  300
ctgcgcatgt ctgccatggc ccccacaccg ccccagggtg aggttgacgc cgactgcatg  360
gacgtcaatg tccgcgggcc tgatggcttc accccgctca tgatcgcctc ctgcagcggg  420
ggcggcctgg agacgggcaa cagcgaggaa gaggaggacg cgccggccgt catctccgac  480
ttcatctacc agggcgccag cctgcacaac cagacagacc gcacgggcga gaccgccttg  540
cacctggccg cccgctactc acgctctgat gccgccaagc gcctgctgga ggccagcgca  600
gatgccaaca tccaggacaa catgggccgc accccgctgc atgcggctgt gtctgccgac  660
gcacaaggtg tcttccagat cctgatccgg aaccgagcca cagacctgga tgcccgcatg  720
catgatggca cgacgccact gatcctggct gcccgcctgg ccgtggaggg catgctggag  780
gacctcatca actcacacgc cgacgtcaac gccgtagatg acctgggcaa gtccgccctg  840
cactgggccg ccgccgtgaa caatgtggat gccgcagttg tgctcctgaa gaacggggct  900
aacaaagata tgcagaacaa cagggaggag acacccctgt ttctggccgc ccgggagggc  960
agctacgaga ccgccaaggt gctgctggac cactttgcca accgggacat cacggatcat  1020
atggaccgcc tgccgcgcga catcgcacag gagcgcatgc atcacgacat cgtgaggctg  1080
ctggacgagt acaacctggt gcgcagcccg cagctgcacg gagcccccgct gggggggcacg  1140
cccaccctgt cgcccccgct ctgctcgccc aacggctacc tgggcagcct caagcccggc  1200
gtgcagggca agaaggtccg caagcccagc agcaaaggcc tggcctgtgg aagcaaggag  1260
gccaaggacc tcaaggcacg gaggaagaag tcccaggacg gcaagggctg cctgctggac  1320
agctccggca tgctctcgcc cgtggactcc ctggagtcac cccatggcta cctgtcagac  1380
gtggcctcgc cgccactgct gccctccccg ttccagcagt ctccgtccgt gcccctcaac  1440
cacctgcctg ggatgcccga cacccacctg ggcatcgggc acctgaacgt ggcggccaag  1500
cccgagatgg cggcgctggg tgggggcggc cggctggcct ttgagactgg cccacctcgt  1560
ctctcccacc tgcctgtggc ctctggcacc agcaccgtcc tgggctccag cagcggaggg  1620
gccctgaatt tcactgtggg cgggtccacc agtttgaatg gtcaatgcga gtggctgtcc  1680
cggctgcaga gcggcatggt gccgaaccaa tacaaccctc tgcgggggag tgtggcacca  1740
ggccccctga gcacacaggc cccctccctg cagcatggca tggtaggccc gctgcacagt  1800
agccttgctg ccagcgccct gtcccagatg atgagctacc agggcctgcc cagcacccgg  1860
ctggccaccc agcctcacct ggtgcagacc cagcaggtgc agccacaaaa cttacagatg  1920
cagcagcaga acctgcagcc agcaaacatc cagcagcagc aaagcctgca gccgccacca  1980
ccaccaccac agccgcacct tggcgtgagc tcagcagcca gcggccacct gggccggagc  2040
ttcctgagtg gagagccgag ccaggcagac gtgcagccac tgggccccag cagcctggcg  2100
gtgcacacta ttctgcccca ggagagcccc gccctgccca cgtcgctgcc atcctcgctg  2160
gtcccacccg tgaccgcagc ccagttcctg acgcccccct cgcagcacag ctactcctcg  2220
cctgtggaca acacccccag ccaccagcta caggtgcctg agcacccctt cctcaccccg  2280
tcccctgagt cccctgacca gtggtccagc tcgtccccgc attccaacgt ctccgactgg  2340
tccgagggcg tctccagccc tcccaccagc atgcagtccc agatcgcccg cattccggag  2400
gccttcaagt aa                                                      2412

SEQ ID NO: 4           moltype = AA  length = 803
FEATURE                Location/Qualifiers
source                 1..803
                       mol_type = protein
                       organism = synthetic construct
SEQUENCE: 4
MVLLSRKRRR QHGQLWFPEG FKVSEASKKK RREPLGEDSV GLKPLKNASD GALMDDNQNE  60
WGDEDLETKK FRFEEPVVLP DLDDQTDHRQ WTQQHLDAAD LRMSAMAPTP PQGEVDADCM  120
DVNVRGPDGF TPLMIASCSG GGLETGNSEE EEDAPAVISD FIYQGASLHN QTDRTGETAL  180
```

-continued

```
HLAARYSRSD AAKRLLEASA DANIQDNMGR TPLHAAVSAD AQGVFQILIR NRATDLDARM  240
HDGTTPLILA ARLAVEGMLE DLINSHADVN AVDDLGKSAL HWAAAVNNVD AAVVLLKNGA  300
NKDMQNNREE TPLFLAAREG SYETAKVLLD HFANRDITDH MDRLPRDIAQ ERMHHDIVRL  360
LDEYNLVRSP QLHGAPLGGT PTLSPPLCSP NGYLGSLKPG VQGKKVRKPS SKGLACGSKE  420
AKDLKARRKK SQDGKGCLLD SSGMLSPVDS LESPHGYLSD VASPPLLPSP FQQSPSVPLN  480
HLPGMPDTHL GIGHLNVAAK PEMAALGGGG RLAFETGPPR LSHLPVASGT STVLGSSSGG  540
ALNFTVGGST SLNGQCEWLS RLQSGMVPNQ YNPLRGSVAP GPLSTQAPSL QHGMVGPLHS  600
SLAASALSQM MSYQGLPSTR LATQPHLVQT QQVQPQNLQM QQQNLQPANI QQQQSLQPPP  660
PPPQPHLGVS SAASGHLGRS FLSGEPSQAD VQPLGPSSLA VHTILPQESP ALPTSLPSSL  720
VPPVTAAQFL TPPSQHSYSS PVDNTPSHQL QVPEHPFLTP SPESPDQWSS SSPHSNVSDW  780
SEGVSSPPTS MQSQIARIPE AFK                                          803

SEQ ID NO: 5           moltype = DNA  length = 2139
FEATURE                Location/Qualifiers
source                 1..2139
                       mol_type = other DNA
                       organism = synthetic construct
SEQUENCE: 5
atgagagagc cggcgctggc ggccagcgcc atggcttacc acccgttcca cgcgccacgg  60
cccgccgact tccccatgtc cgcctttctg gcggcggcgc agccctcctt cttcccggca  120
ctcgcgctgc cgcccggcgc gctggccaag ccgctgcccg acccgggcct ggcgggggcg  180
gcggccgcgg cggcggcggc ggcagcagcg gccgaggcgg ggctgcacgt ctcggcactg  240
ggcccgcacc cgcccgccgc gcatctgcgc tccctcaaga gcctggagcc cgaggacgag  300
gtggaggacg accccaaggt gacgctggag gccaaggagc tgtgggacca gttccacaag  360
ctaggcacgg agatggtcat caccaagtcc gggaggcgga tgttcccccc cttcaaggtg  420
cgagtcagcg gcctggacaa gaaggccaag tatatcctgc tgatggacat tgtagccgct  480
gacgattgcc gctataagtt ccacaactcg cgctggatgg tggcgggcaa ggccgaccct  540
gagatgccca aacgcatgta catccaccca gacagcccag ccacggggga gcagtggatg  600
gctaagcctg tggccttcca caagctgaag ctgaccaaca acatctctga caagcacggc  660
ttcaccatcc taaactccat gcacaagtac cagccgcgct tccacatagt gcgagccaac  720
gacatcctga agctgcctta cagcaccttc cgcacctacg tgttcccgga gaccgacttc  780
atcgccgtca ctgcctacca gaatgacaag atcacacagc tgaagatcga caacaacccg  840
tttgccaagg gcttccggga caccgggaac ggccggcggg agaaaaggaa gcagctgacg  900
ctgccgtctc tacgcttgta cgaggagcac tgcaaacccg agcgcgatgg cgcggagtca  960
gacgcctcgt cgtgcgaccc tccccccgcg cgggaaccac ccacctcccc gggcgcagcg  1020
cccagtccgc tgcgcctgca ccgggcccga gctgaggaga agtcgtgcgc cgcggacagc  1080
gacccggagc ctgagcggtt gagcgaggag cgtgcggggg cgccgctagg ccgcagcccg  1140
gctccagaca gcgccagccc cactcgcttg accgaacccg agcgcgcccg ggagcggcgt  1200
agtcccgaga ggggcaagga gccggccgag agcggcgggg acggcccgtt cggcctgagg  1260
agcctggaga aggagcgcgc cgaagctcgg aggaaggacg aggggcgcaa ggaggcggcc  1320
gagggcaagg agcagggcct ggcgccgctg gtggtgcaga cagacagtgc gtccccccctg  1380
ggcgccggac acctgcccgg cctggccttt tccagccact tgcacgggca gcagttcttt  1440
gggccgctgg gagccggcca gccgctcttc ctgcaccctg gacagttcac catgggccct  1500
ggcgccttct ccgccatggg catgggtcac ctactggcct cggtggcagg cggcggcaac  1560
ggcggaggtg gcgggcctgg gaccgccgcg gggctggacg caggcgggct gggtcccgcg  1620
gccagcgcag caagcaccgc cgcgcccttc ccgttccacc tctcccagca catgctggca  1680
tctcagggaa ttccaatgcc cactttcgga ggcctcttcc cctaccccta cacctacatg  1740
gcagcagcag ccgcagccgc ctcggctttg cccgccacta gtgctgcagc tgccgccgcc  1800
gcagccgccg gctccctctc ccggagcccc ttcctgggca gtgcccggcc ccgactgcgt  1860
ttcagcccct atcagatccc ggtcaccatc ccgcctagca ctagcctcct caccaccggg  1920
ctggcctctg agggctccaa ggccgctggt ggaaacagcc gggagcctag ccccctgccc  1980
gagctggctc tccgcaaagt aggggcccca tcccgcggtg ccctgtcgcc cagtggctcg  2040
gccaaggagg cggccaatga actgcagagc atccagagac tggtgagtgg gctggagagc  2100
cagcgagccc tctccccagg ccgggagtcg cccaagtga                         2139

SEQ ID NO: 6           moltype = AA  length = 712
FEATURE                Location/Qualifiers
source                 1..712
                       mol_type = protein
                       organism = synthetic construct
SEQUENCE: 6
MREPALAASA MAYHPFHAPR PADFPMSAFL AAAQPSFFPA LALPPGALAK PLPDPGLAGA  60
AAAAAAAAAA AEAGLHVSAL GPHPPAAHLR SLKSLEPEDE VEDDPKVTLE AKELWDQFHK  120
LGTEMVITKS GRRMFPPFKV RVSGLDKKAK YILLMDIVAA DDCRYKFHNS RWMVAGKADP  180
EMPKRMYIHP DSPATGEQWM AKPVAFHKLK LTNNISDKHG FTILNSMHKY QPRFHIVRAN  240
DILKLPYSTF RTYVFPETDF IAVTAYQNDK ITQLKIDNNP FAKGFRDTGN GRREKRKQLT  300
LPSLRLYEEH CKPERDGAES DASSCDPPPA REPPTSPGAA PSPLRLHRAR AEEKSCAADS  360
DPEPERLSEE RAGAPLGRSP APDSASPTRL TEPERARERR SPERGKEPAE SGGDGPFGLR  420
SLEKERAEAR RKDEGRKEAA EGKEQGLAPL VVQTDSASPL GAGHLPGLAF SSHLHGQQFF  480
GPLGAGQPLF LHPGQFTMGP GAFSAMGMGH LLASVAGGGN GGGGGPGTAA GLDAGGLGPA  540
ASAASTAAPF PFHLSQHMLA SQGIPMPTFG GLFPYPYTYM AAAAAAASAL PATSAAAAAA  600
AAAGSLSRSP FLGSARPRLR FSPYQIPVTI PPSTSLLTTG LASEGSKAAG GNSREPSPLP  660
ELALRKVGAP SRGALSPSGS AKEAANELQS IQRLVSGLES QRALSPGRES PK          712

SEQ ID NO: 7           moltype = DNA  length = 38
FEATURE                Location/Qualifiers
source                 1..38
                       mol_type = other DNA
                       organism = synthetic construct
```

```
SEQUENCE: 7
taagcattaa ttaagccacc atggtcatgg tggcccgg                          38

SEQ ID NO: 8            moltype = DNA  length = 31
FEATURE                 Location/Qualifiers
source                  1..31
                        mol_type = other DNA
                        organism = synthetic construct
SEQUENCE: 8
tgcttattaa ttaatcaggc caacacttgc c                                 31

SEQ ID NO: 9            moltype = DNA  length = 43
FEATURE                 Location/Qualifiers
source                  1..43
                        mol_type = other DNA
                        organism = synthetic construct
SEQUENCE: 9
taagcattaa ttaagccacc atggtgctgc tgtcccgcaa gcg                    43

SEQ ID NO: 10           moltype = DNA  length = 34
FEATURE                 Location/Qualifiers
source                  1..34
                        mol_type = other DNA
                        organism = synthetic construct
SEQUENCE: 10
tgcttattaa ttaattactt gaaggcctcc ggaa                              34

SEQ ID NO: 11           moltype = DNA  length = 36
FEATURE                 Location/Qualifiers
source                  1..36
                        mol_type = other DNA
                        organism = synthetic construct
SEQUENCE: 11
taagcattaa ttaagccacc atgagagagc cggcgc                            36

SEQ ID NO: 12           moltype = DNA  length = 31
FEATURE                 Location/Qualifiers
source                  1..31
                        mol_type = other DNA
                        organism = synthetic construct
SEQUENCE: 12
tgcttattaa ttaatcactt gggcgactcc c                                 31

SEQ ID NO: 13           moltype = DNA  length = 21
FEATURE                 Location/Qualifiers
source                  1..21
                        mol_type = other DNA
                        organism = synthetic construct
SEQUENCE: 13
tcaagcctca gacagtggtt c                                            21

SEQ ID NO: 14           moltype = DNA  length = 20
FEATURE                 Location/Qualifiers
source                  1..20
                        mol_type = other DNA
                        organism = synthetic construct
SEQUENCE: 14
cctcacattg ccaaaagacg                                              20

SEQ ID NO: 15           moltype = DNA  length = 18
FEATURE                 Location/Qualifiers
source                  1..18
                        mol_type = other DNA
                        organism = synthetic construct
SEQUENCE: 15
gaaccgcatc gagctgaa                                                18

SEQ ID NO: 16           moltype = DNA  length = 21
FEATURE                 Location/Qualifiers
source                  1..21
                        mol_type = other DNA
                        organism = synthetic construct
SEQUENCE: 16
tgcttgtcgg ccatgatata g                                            21

SEQ ID NO: 17           moltype = DNA  length = 20
FEATURE                 Location/Qualifiers
source                  1..20
                        mol_type = other DNA
```

```
                       organism = synthetic construct
SEQUENCE: 17
gtgggacaga gtctgggtgt                                              20

SEQ ID NO: 18          moltype = DNA  length = 20
FEATURE                Location/Qualifiers
source                 1..20
                       mol_type = other DNA
                       organism = synthetic construct
SEQUENCE: 18
aaggagggga ggtgatagga                                              20

SEQ ID NO: 19          moltype = DNA  length = 22
FEATURE                Location/Qualifiers
source                 1..22
                       mol_type = other DNA
                       organism = synthetic construct
SEQUENCE: 19
gctcaccatc atctccctta tc                                           22

SEQ ID NO: 20          moltype = DNA  length = 22
FEATURE                Location/Qualifiers
source                 1..22
                       mol_type = other DNA
                       organism = synthetic construct
SEQUENCE: 20
ctcacagact caatcacctt cc                                           22

SEQ ID NO: 21          moltype = DNA  length = 23
FEATURE                Location/Qualifiers
source                 1..23
                       mol_type = other DNA
                       organism = synthetic construct
SEQUENCE: 21
ggaggctcct aaagaggtga ata                                          23

SEQ ID NO: 22          moltype = DNA  length = 21
FEATURE                Location/Qualifiers
source                 1..21
                       mol_type = other DNA
                       organism = synthetic construct
SEQUENCE: 22
ccatcagggc atggattctt t                                            21

SEQ ID NO: 23          moltype = DNA  length = 21
FEATURE                Location/Qualifiers
source                 1..21
                       mol_type = other DNA
                       organism = synthetic construct
SEQUENCE: 23
aacctggcgc ataagaacat c                                            21

SEQ ID NO: 24          moltype = DNA  length = 21
FEATURE                Location/Qualifiers
source                 1..21
                       mol_type = other DNA
                       organism = synthetic construct
SEQUENCE: 24
ccacatgata gcgaagagca g                                            21

SEQ ID NO: 25          moltype = DNA  length = 21
FEATURE                Location/Qualifiers
source                 1..21
                       mol_type = other DNA
                       organism = synthetic construct
SEQUENCE: 25
gagacgctcg tcagttctta g                                            21

SEQ ID NO: 26          moltype = DNA  length = 22
FEATURE                Location/Qualifiers
source                 1..22
                       mol_type = other DNA
                       organism = synthetic construct
SEQUENCE: 26
ggtggaaaga gaagaggatg aa                                           22

SEQ ID NO: 27          moltype = DNA  length = 20
FEATURE                Location/Qualifiers
source                 1..20
```

```
                         mol_type = other DNA
                         organism = synthetic construct
SEQUENCE: 27
acatcctgaa gctgccttac                                              20

SEQ ID NO: 28            moltype = DNA  length = 22
FEATURE                  Location/Qualifiers
source                   1..22
                         mol_type = other DNA
                         organism = synthetic construct
SEQUENCE: 28
agctgtgtga tcttgtcatt ct                                           22

SEQ ID NO: 29            moltype = DNA  length = 20
FEATURE                  Location/Qualifiers
source                   1..20
                         mol_type = other DNA
                         organism = synthetic construct
SEQUENCE: 29
cagatgcaag ccaggaagaa                                              20

SEQ ID NO: 30            moltype = DNA  length = 21
FEATURE                  Location/Qualifiers
source                   1..21
                         mol_type = other DNA
                         organism = synthetic construct
SEQUENCE: 30
ggaagagccc tgtttctcaa a                                            21

SEQ ID NO: 31            moltype = DNA  length = 20
FEATURE                  Location/Qualifiers
source                   1..20
                         mol_type = other DNA
                         organism = synthetic construct
SEQUENCE: 31
ccaaggacaa ccacacagaa                                              20

SEQ ID NO: 32            moltype = DNA  length = 22
FEATURE                  Location/Qualifiers
source                   1..22
                         mol_type = other DNA
                         organism = synthetic construct
SEQUENCE: 32
gccacagagt aaatcccaag ag                                           22

SEQ ID NO: 33            moltype = DNA  length = 20
FEATURE                  Location/Qualifiers
source                   1..20
                         mol_type = other DNA
                         organism = synthetic construct
SEQUENCE: 33
cccaggactc cctcctatgt                                              20

SEQ ID NO: 34            moltype = DNA  length = 20
FEATURE                  Location/Qualifiers
source                   1..20
                         mol_type = other DNA
                         organism = synthetic construct
SEQUENCE: 34
taggaaccct gatgggtctg                                              20

SEQ ID NO: 35            moltype = DNA  length = 23
FEATURE                  Location/Qualifiers
source                   1..23
                         mol_type = other DNA
                         organism = synthetic construct
SEQUENCE: 35
accagagcgt ctgtcaggat att                                          23

SEQ ID NO: 36            moltype = DNA  length = 24
FEATURE                  Location/Qualifiers
source                   1..24
                         mol_type = other DNA
                         organism = synthetic construct
SEQUENCE: 36
gtgacttgaa tccgtcccag tttc                                         24

SEQ ID NO: 37            moltype = DNA  length = 22
FEATURE                  Location/Qualifiers
```

-continued

```
source                 1..22
                       mol_type = other DNA
                       organism = synthetic construct
SEQUENCE: 37
gtcccagatc caggagttta ag                                              22

SEQ ID NO: 38          moltype = DNA  length = 20
FEATURE                Location/Qualifiers
source                 1..20
                       mol_type = other DNA
                       organism = synthetic construct
SEQUENCE: 38
catcatgccc tccaggtatt                                                 20

SEQ ID NO: 39          moltype = DNA  length = 19
FEATURE                Location/Qualifiers
source                 1..19
                       mol_type = other DNA
                       organism = synthetic construct
SEQUENCE: 39
agaggaccag actgggaaa                                                  19

SEQ ID NO: 40          moltype = DNA  length = 20
FEATURE                Location/Qualifiers
source                 1..20
                       mol_type = other DNA
                       organism = synthetic construct
SEQUENCE: 40
caggcagatt aagccgatca                                                 20

SEQ ID NO: 41          moltype = DNA  length = 22
FEATURE                Location/Qualifiers
source                 1..22
                       mol_type = other DNA
                       organism = synthetic construct
SEQUENCE: 41
cgaagactgt gtgtctgaga ag                                              22

SEQ ID NO: 42          moltype = DNA  length = 22
FEATURE                Location/Qualifiers
source                 1..22
                       mol_type = other DNA
                       organism = synthetic construct
SEQUENCE: 42
ctcagccggt aaatcctgta tg                                              22

SEQ ID NO: 43          moltype = DNA  length = 20
FEATURE                Location/Qualifiers
source                 1..20
                       mol_type = other DNA
                       organism = synthetic construct
SEQUENCE: 43
tgttccagcc atccttcatc                                                 20

SEQ ID NO: 44          moltype = DNA  length = 20
FEATURE                Location/Qualifiers
source                 1..20
                       mol_type = other DNA
                       organism = synthetic construct
SEQUENCE: 44
gcaatgccag ggtacatagt                                                 20
```

METHOD FOR DIFFERENTIATION OF BRAIN MURAL CELLS FROM HUMAN PLURIPOTENT STEM CELLS

CROSS REFERENCED TO RELATED APPLICATIONS

This patent application claims the benefit of priority of United States Provisional Patent Application No. 63/246,238 filed on Sep. 20, 2021, which is incorporated herein by reference in its entirety.

STATEMENT REGARDING FEDERALLY SPONSORED RESEARCH

This invention was made with government support under NS103844 awarded by the National Institutes of Health. The government has certain rights in the invention.

REFERENCE TO AN ELECTRONIC SEQUENCE LISTING

The contents of the electronic sequence listing (960296.04319.xml; Size: 48,340 bytes; and Date of Creation: Sep. 14, 2022) is herein incorporated by reference in its entirety.

BACKGROUND

Vascular mural cells, which encompass microvessel-associated pericytes and large vessel-associated vascular smooth muscle cells (VSMCs), regulate blood vessel development, stability, and vascular tone. In the brain, mural cells regulate resting cerebral blood flow, neurovascular coupling, blood-brain barrier development and maintenance, and neuron survival. Brain mural cells are also implicated in the pathogenesis of neurological disorders including Alzheimer's disease and cerebral autosomal dominant arteriopathy with subcortical infarcts and leukoencephalopathy (CADASIL).

In contrast to the mesodermal origin of most mural cells, those in the face and forebrain are derived from the neural crest. During embryogenesis, cranial neural crest-derived mesenchyme (mesectoderm) surrounds the anterior neural tube, and mural cells are specified and invade the developing prosencephalon alongside mesoderm-derived endothelial cells from the perineural vascular plexus. This neural crest-derived mesenchyme also forms the meninges, facial bone, cartilage, and connective tissue, and portions of the skull. Molecular signals controlling specification of neural crest-derived mesenchyme to these diverse fates are poorly understood; however, endothelium-derived signals likely direct mural cell differentiation. In vivo loss of function experiments have suggested roles for TGF-β, PDGF, and Notch signaling in this process. Notably, NOTCH3 mutations form the genetic basis of CADASIL, and studies in Zebrafish have implicated Notch signaling in brain pericyte proliferation and specification of pericytes from naïve neural crest-derived mesenchyme. It is difficult, however, to discriminate between deficits in specification/differentiation and recruitment of mural cells to nascent vessels in most in vivo studies. Thus, in vitro models are complementary and can provide mechanistic insight into the effects of molecular factors on neural crest differentiation.

Human pluripotent stem cells (hPSCs) are a promising in vitro model system for such studies, as they can generate naïve, multipotent neural crest cells, potentially account for species differences in mural cell phenotype, and the resulting cells could be employed in diverse in vitro modeling applications. We recently demonstrated that brain pericyte-like cells could be differentiated from hPSC-derived neural crest via treatment with serum-supplemented E6 medium. Other protocols for generating hPSC-derived brain pericyte-like cells via a neural crest intermediate use PDGF-BB and/or FGF2 but each protocol adds these factors to serum-containing media. The sufficiency of serum to cause differentiation of neural crest cells makes interrogation of specific molecular factors difficult, motivating development of a serum-free differentiation scheme. Furthermore, while existing hPSC-derived pericyte-like cells have many molecular and functional attributes of pericytes in vivo, they lack expression of some key brain mural cell genes and have aberrant expression of some fibroblast-associated genes, features also observed in cultured primary brain pericytes. This further motivates development of a new protocol for hPSC differentiation to brain mural cells with an improved molecular phenotype.

Needed in the art is an improved method of creating hPSC-derived mural cells that can be used in models and for drug discovery and testing purposes.

SUMMARY OF INVENTION

In one aspect, the present disclosure provides a method of producing a population of mural cells comprising the steps of: a) increasing Notch expression and/or signaling in a population of p75-NGFR$^+$HNK-1$^+$ neural crest (NC) cells; and b) culturing the Notch-activated NC cells in serum-free medium for a sufficient time to differentiate the NC cells into NOTCH3$^+$PDGFRβ$^+$RGS5$^+$ brain mural cells.

In another aspect, the present disclosure provides a method of creating a population of NOTCH3$^+$PDGFRβ$^+$RGS5$^+$ brain mural cells comprising: a) culturing hPSCs in E6-CSFD medium for about 15 days to produce p75-NGFR$^+$ HNK-1$^+$ NCSCs, b) sorting p75-NGFR$^+$ cells and re-plating the p75-NGFR$^+$ cells of step (a) to produce a population of p75-NGFR$^+$ NCSCs; c) activating notch signaling in the sorted p75-NGFR$^+$HNK-1$^+$ NCSCs of step b), and d) culturing the cells of step (c) in serum free medium for a sufficient time to differentiate NOTCH3$^+$PDGFRβ$^+$RGS5$^+$ brain mural cells.

In another aspect, the disclosure provides a population of NOTCH3$^+$PDGFRβ$^+$RGS5$^+$ brain mural cells produced by the methods described herein.

In a further aspect, the disclosure provides a BBB model, wherein the model comprises the population of NOTCH3$^+$PDGFRβ$^+$RGS5$^+$ brain mural cells described herein and brain microvascular endothelial cells (BMECs), wherein the BBB model is capable of forming tight junctions. The BBB model may be an isogenic BBB model. The BBB model may also include a permeable membrane.

In a still further aspect, methods of using the NOTCH3$^+$PDGFRβ$^+$RGS5$^+$ brain mural cells in in vitro assays are also provided. The cells may be used for drug screening and tissue development or assays.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
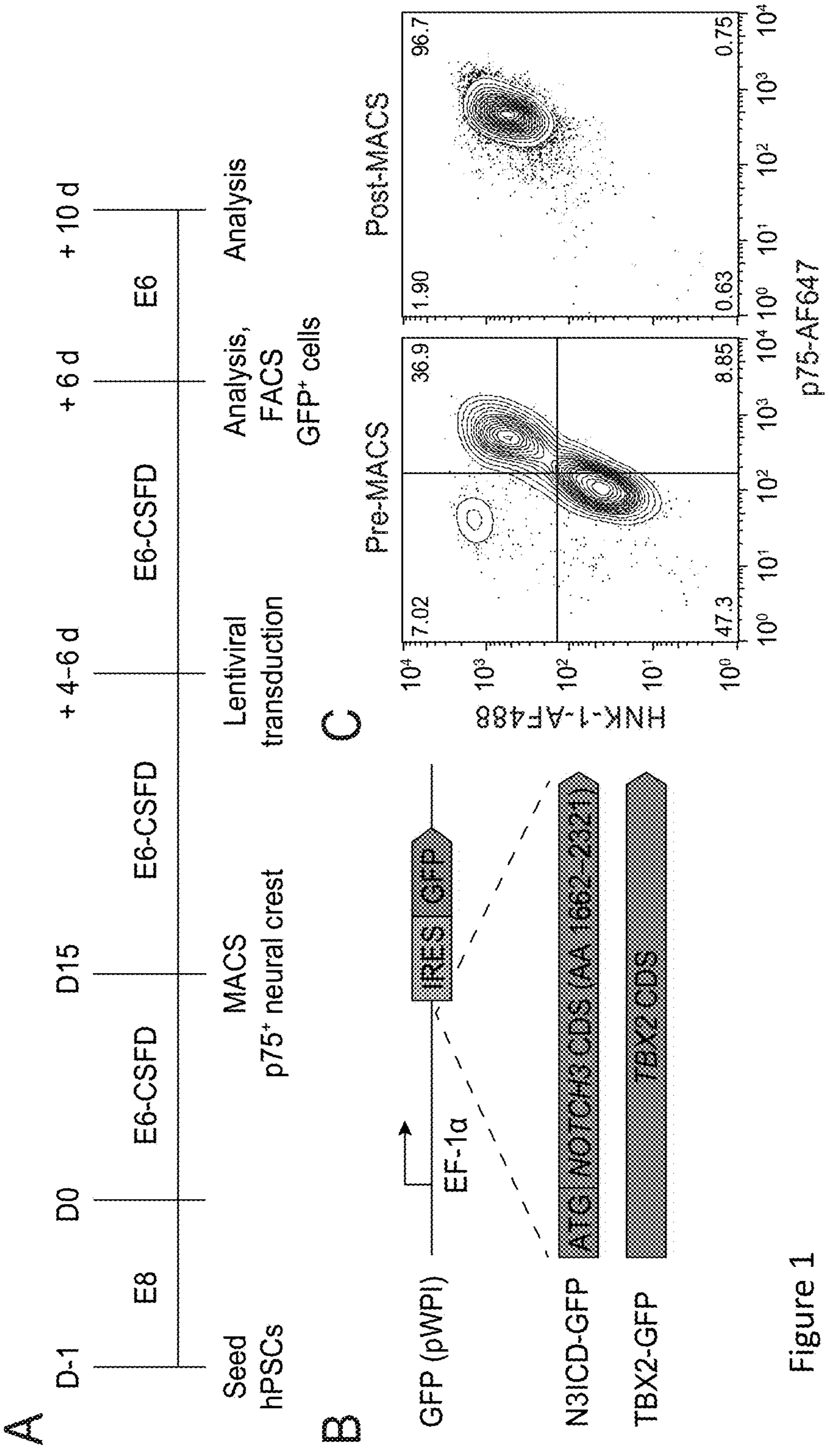
FIG. 1. Overview of differentiation strategy. (A) Timeline of the differentiation protocol. (B) Schematic of lentiviral overexpression constructs. A fragment of the human NOTCH3 coding sequence (CDS) encoding the intracellular domain of Notch3, and the human TBX2 CDS, were cloned into the bicistronic lentiviral vector pWPI. The parental pWPI vector was used as a GFP-only control. IRES: internal ribosome entry site; AA: amino acids. (C) Flow cytometry analysis of p75 and HNK-1 expression in D15 neural crest cells before and after p75 MACS. (D) RT-qPCR analysis of mural cell gene expression 6 days after transduction with GFP, N3ICD-GFP, or TBX2-GFP lentiviruses. Expression of each gene is shown relative to ACTB expression and normalized to expression in GFP-transduced cells. Points represent replicate wells from a differentiation of the H9 hPSC line and bars indicate mean values. P-values: ANOVA followed by Dunnett's test versus GFP-transduced cells.
Figure 1:
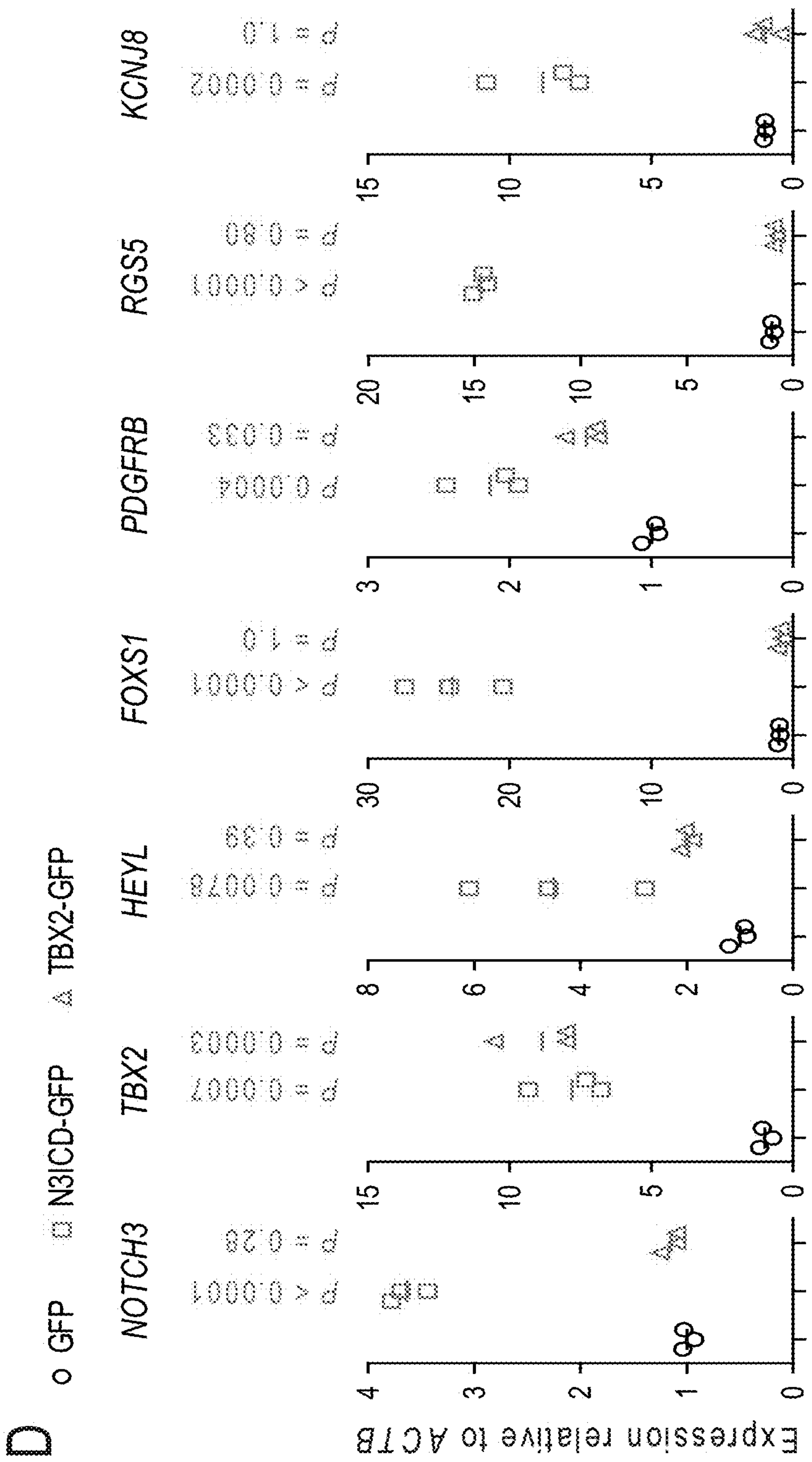

The present invention is based in part on the surprising finding that activation of Notch3 or Notch1 signaling directed the differentiation of hPSC-derived neural crest to brain mural cells. Further, overexpression of Tbx2 (SEQ ID NO:5 and 6), another mural cell-enriched transcription factor similar to Notch3 and Notch1, did not similarly induce brain mural cells. Because ligand-induced activation of Notch signaling requires complex cell-cell interactions and ligand endocytosis, the inventors activated Notch signaling by lentiviral overexpression of the human Notch3 or Notch1 intracellular domain in neural crest cells maintained in serum-free medium. The resulting cells were PDGFRβ$^+$ and displayed robust upregulation of the mural cell genes HEYL, RGS5, TBX2, and FOXS1. Supplementation of additional molecular factors did not substantially improve the transcriptional profile of the resulting cells. Thus, Notch3 or Notch1 signaling is sufficient to direct differentiation of neural crest to brain mural cells under serum-free conditions, and thus establishes a new, serum-free protocol for generation of brain mural cells from hPSCs. These in vitro derived brain mural cells can be used in CNS drug screening, BBB models and development studies and disease modeling applications.

Abbreviations used in the present disclosure include, blood-brain barrier, BBB; brain microvascular endothelial cells, BMECs; central nervous system, CNS; E6 medium supplemented with CHIR99021, SB431542, FGF2, and dorsomorphin, E6-CSFD; endothelial cells, ECs; endothelial growth factor medium 2, EGM-2; green fluorescent protein, GFP; human embryonic stem cells, hESCs; human pluripotent stem cells, hPSCs; human umbilical vein endothelial cells, HUVECs; induced pluripotent stem cells, iPSCs; Notch1 intracellular domain, N1ICD; Notch3 intracellular domain, N3ICD; neural crest stem cells, NCSC; neurovascular unit, NVU; vascular smooth muscle cells, VSMCs.

Brain pericytes and vascular smooth muscle cells (VSMCs), collectively termed mural cells, regulate development and function of the blood-brain barrier (BBB) and control brain blood flow. Unlike the mesoderm-derived mural cells of other organs, forebrain mural cells (also called brain mural cells or vascular mural cells) are derived from the neural crest. Molecular signals controlling mural cell differentiation are poorly understood, with loss of function experiments suggesting roles for TGF-β, PDGF, and Notch signaling. Existing in vitro models of human brain mural cells derived both from primary cultures and human pluripotent stem cells (hPSCs) have markedly reduced expression of key mural cell genes, including NOTCH3, compared to in vivo samples, and require serum-supplemented culture media. The present invention fulfills a need for in vitro derived mural cells that have key aspects of the mural cells and proper gene expression that can be used in vitro for creating BBB models and development and drug discovery applications.

The present invention provides populations of in vitro derived brain mural cells and methods of producing brain mural cells under serum free conditions, allowing for their use in studies allowing for standardization of conditions and reproducibility of the components in the culture media, which is ideal for analysis. These brain mural cells can be used for in vitro BBB models, 3D models of blood brain barrier and other tissue and chip technology that can be used to study blood brain barrier properties, development and therapeutics. As demonstrated in the Examples, the overexpression of the human Notch3 intracellular domain (N3ICD) or human Notch1 (N1ICD) in neural crest cells directed mural cell differentiation under serum free conditions. Unexpectedly, while other factors are thought to play a role (e.g., TGFβ, TBX2), these factors did not result in the differentiation of mural cells from neural crest stem cells as described in the Examples. Thus, the present invention provides a novel serum-free method of in vitro deriving brain mural cells for study and down-stream applications.

The in vitro derived brain mural cells of the present invention are NOTCH3$^+$PDGFRβ$^+$RGS5$^+$ brain mural cells. These mural cells of the present invention can form both smooth muscle cells, which line arterioles and venules, and pericytes, which are associated with smaller microvessels and capillaries. Preferably, the methods produce a cell population that is at least 90% NOTCH3$^+$PDGFRβ$^+$RGS5$^+$ brain mural cells, preferably at least 95% NOTCH3$^+$PDGFRβ$^+$RGS5$^+$ brain mural cells. The NOTCH3$^+$PDGFRβ$^+$RGS5$^+$ brain mural cells may also express one or more additional marker associated with mural cells, e.g., FOXS1, TBX2, and HEYL. Additionally, the mural cells express pericyte-specific markers (e.g., KCNJ8) at certain timepoints, but additional factors may need to be used for maintenance of this phenotype or further differentiation.

In one aspect, the present disclosure provides a method of producing a population of mural cells. The method comprises (a) increasing Notch expression and/or activation in a population of p75-NGFR$^+$HNK-1$^+$ neural crest (NC) cells; and (b) culturing the Notch-activated NC cells in serum-free medium for a sufficient time to differentiate the NC cells into NOTCH3$^+$PDGFRβ$^+$RGS5$^+$ brain mural cells. Suitably, in some embodiments, the culturing step of Notch-activated NC cells in serum free medium to obtain NOTCH3$^+$PDGFRβ$^+$RGS5$^+$ brain mural cells is at least 6 days. The brain mural cells may be cultured and split for additional passages for up to 60 days.

It is contemplated that a number of different methods and strategies may be used for increasing the Notch expression and/or signaling within the NC cells to promote differentiation into mural cells. For example, Notch expression or Notch signaling within the NC cell may be accomplished by methods known in the art to activate the Notch signaling pathway. Some examples, include, for example, (i) introducing a exogenous construct encoding at least an intracellular domain of Notch receptor and capable of expressing at least the intracellular domain within the NC cell, although additional Notch receptor and/or ligand sequences may also be included; (ii) culturing the NC cells in serum free medium in the presence of Notch ligands (e.g., DLL4, JAG2, etc.); (iii) co-culturing the NC cells with cells overexpressing Notch ligands (e.g., feeder cell line, etc.) or (iv) activating Notch pathway using a Notch activation factor. Suitable methods of activating the Notch pathway are known and understood in the art. In one aspect, an exogenous construct comprises a Notch receptor, Notch ligand, or a Notch activating factor or active fragments thereof. In one example, the Notch receptor comprises at least a Notch intracellular domain (e.g., Notch 3 or Notch 1 intracellular domain) and capable of expressing the Notch intracellular domain.

In some embodiments, the construct encoding a Notch receptor, Notch ligand, or fragment thereof or Notch activating factor may suitably be a vector. In a preferred embodiment, the construct may be a viral vector, for example, a lentiviral vector that allows for integration and stable expression of the Notch intracellular domain encoded within the cell. In other embodiments, expression vectors may be used that allow for transient expression of the Notch intracellular domain within the cell. In other aspects, other methods may be used to overexpress Notch within the NC cells, for example, either the NC cells or the hPSCs used to derive the NC can be genetically modified with a construct (e.g. by viral, transposon, CRISPR-based strategies) that has a inducible construct for notch intracellular domain expression (e.g., doxycycline-inducible). Suitable doxycycline vectors and constructs are known in the art, and expression is then inducible by the addition of doxycycline or other suitable inductor into the culture medium.

In some embodiments the vector may comprise a polynucleotide encoding the intracellular domain of Notch3, for example, SEQ ID NO:1 or another polynucleotide capable of encoding SEQ ID NO: 2. Alternatively, the vector may comprise a polynucleotide encoding the intracellular domain of Notch1, for example SEQ ID NO: 3 or another polynucleotide capable of encoding SEQ ID NO: 4. Due to the degeneracy of the genetic code those of skill in the art will appreciate that the polypeptides of SEQ ID NO: 2 and 4 may be encoded for by many distinct polynucleotides. In addition, the polypeptides can also maintain function with a small number of amino acid changes. Thus also encompassed herein are polynucleotides and polypeptides having at least 90%, 92%, 94%, 95%, 97% 98% or 99% identity to the sequences provided in SEQ ID NO: 1-4. The vector may comprise additional sequences, including promoter sequences. Heterologous promoters useful in the practice of the present invention include, but are not limited to, constitutive, inducible, temporally-regulated, developmentally regulated, chemically regulated, tissue-preferred, tissue-specific promoters and cell-type specific. The heterologous promoter may be a plant, animal, bacterial, fungal, or synthetic promoter. Suitable promoters are known and described in the art. Promoters may include the EF-1alpha, SV40, CMV, UBC, PGK or CAGG. The vector may additionally comprise one or more IRES element, enhancer element, translation initiation sequence, ribosomal binding site, start codon, termination codon, transcriptional termination sequence, targeting sequence and/or tag.

In another aspect, the NC cells may be cultured in the presence of excess Notch ligands. Suitable means of culturing cells with notch ligands include, for example, culturing the NC cells in the presence of beads coated with Notch ligands (e.g. DLL4 or JAG2). Other suitable notch ligands may also be used (e.g., DSL ligands, Delta and Serrate, three of which belong to the Delta-like family (DLL1, DLL3 and DLL4) and two belong to the Jagged family of Serrate homologs, Jagged 1 and 2 (also known as JAG1 and JAG2, respectively) and their use can be determined by one skilled in the art). Suitable beads are known in the art and comprise, for example, agarose, polymer or magnetic beads. Suitable methods of deriving beads coated with notch ligands are known in the art, for example, surfaces of microbeads are coated with Streptavidin which then binds the biotin attached to the anti-HIS antibody in which recombinant DLL4 with a HIS tag can be attached to the antibody. This method allows for the DLL4 to be immobilized and presented in a highly directional manner on the surface of the beads. Alternatively, for example, recombinant DLL4-Fc or JAG2-Fc fusion proteins can be attached to agarose beads coated with Protein A or Protein G, in which the Fc domain binds to Protein A or Protein G.

In another aspect, the NC cells may be cultured on culture plates coated with Notch ligands (e.g., DLL4 or JAG2). In some embodiments, the plates may be coated with collagen or Matrigel prior to incubation with Notch ligand. Methods of coating plates with proteins including notch are readily understood and known in the art.

In another aspect, the NC cells can be co-cultured with a second cell type that has been genetically altered to overexpress Notch ligands. Suitable co-culture cells are readily known and available in the art.

As used herein, the term "construct", "nucleic acid construct" or "DNA construct" refers to an artificially constructed (i.e., not naturally occurring) DNA molecule that is capable of expressing the polypeptide. Nucleic acid constructs may be part of a vector that is used, for example, to transform a cell. The term "vector" refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors". Vectors suitable for use with the present invention comprise the constructs described herein and heterogeneous sequence necessary for proper propagation of the vector and expression of the encoded polypeptide. Preferably, the constructs are packaged in a vector suitable for delivery into a mammalian cell including but not limited to, an adeno-associated viral (AAV) vector, a lentiviral vector, or a vector suitable for transient transfection. As used herein, the term "vector," "virus vector," "delivery vector" (and similar terms) generally refers to a virus particle that functions as a nucleic acid delivery vehicle, and which comprises the viral nucleic acid (i.e., the vector genome) packaged within the virion. Suitable vectors are known and commercially available in the art. A skilled artisan will be familiar with the elements and configurations necessary for vector construction to encode the constructs described herein.

The term "neural crest (NC) cells" or "neural crest stem cells (NCSC)" are used herein interchangeably to refer to a multipotent stem cell or progenitor population capable of forming peripheral neurons and mesenchymal derivatives including adipocytes, osteocytes, and chondrocytes, among other cell types. NCSCs are the embryonic precursor to forebrain pericytes. As described in the Examples, the neural crest cells used in the methods described herein are differentiated from human pluripotent stem cells, including induced pluripotent stem cells. Suitable methods of deriving neural crest cells are described in US Patent Publication No. US2020/0017827 and Stebbins et al., 2019, both of which are incorporated by reference in their entirety. Neural crest cells are identified by expression of key neural crest markers, including, for example, at least p75-NGFR and HNK-1 (B3GAT1), and can express one or more additional neural crest markers. Cells can be sorted during differentiation as p75-NGFR$^+$ to obtain a homogenous population of p75-NGFR$^+$ neural crest stem cells (NCSC). Such NCSCs can be expanded in culture before use as the starting population for deriving the mural cells of the present invention. The neural crest cells can be denoted as p75-NGFR$^+$HNK-1$^+$ neural crest (NC) cells, and the starting population of p75-NGFR$^+$ HNK-1$^+$ NC cells can be at least 90% pure, alternatively at least 95% pure, alternatively at least 98% p75-NGFR$^+$HNK-1$^+$ NC cells.

The present methods provide advantages of deriving mural cells from those in the art in that the mural cells are derived from NCSCs in serum free medium wherein the medium is defined. The term "defined culture medium" is used herein to indicate that the identity and quantity of each medium ingredient is known. As used herein, the terms "chemically-defined culture conditions," "fully defined, growth factor free culture conditions," and "fully-defined conditions" indicate that the identity and quantity of each medium ingredient is known and the identity and quantity of supportive surface is known. As used herein the term "xenogen-free" refers to medium that does not contain any products obtained from a non-human animal source. As used herein, the term "serum albumin-free" indicates that the culture medium used contains no added serum albumin in any form, including without limitation bovine serum albumin (BSA) or any form of recombinant albumin. Standardizing culture conditions by using a chemically defined culture medium minimizes the potential for lot-to-lot or batch-to-batch variations in materials to which the cells are exposed during cell culture. Accordingly, the effects of various differentiation factors are more predictable when added to cells and tissues cultured under chemically defined conditions. As used herein, the term "serum-free" refers to cell culture materials that do not contain serum or serum replacement, or that contain essentially no serum or serum replacement. For example, an essentially serum-free medium can contain less than about 1%, 0.9%, 0.8%, 0.7%, 0.6%, 0.5%, 0.4%, 0.3%, 0.2%, or 0.1% serum. "Serum free" also refers to culture components free of serum obtained from animal blood and of animal-derived materials, which reduces or eliminates the potential for cross-species viral or prion transmission. Further, serum-containing medium is not chemically defined, producing a degree of variability in the culture conditions. Suitable defined media include, but are not limited to, E8 medium and E6 medium.

Any appropriate method can be used to detect expression of biological markers characteristic of cell types described herein. For example, the presence or absence of one or more biological markers can be detected using, for example, RNA sequencing, immunohistochemistry, polymerase chain reaction, qRT-PCR, or other technique that detects or measures gene expression. Suitable methods for evaluating the above-markers are well known in the art and include, e.g., qRT-PCR, RNA-sequencing, and the like for evaluating gene expression at the RNA level. Quantitative methods for evaluating expression of markers at the protein level in cell populations are also known in the art. For example, flow cytometry is typically used to determine the fraction of cells in a given cell population that express (or do not express) a protein marker of interest (e.g., NOTCH3, GFP, PDGFRβ). In some cases, cell populations obtained by the differentiation methods of this disclosure comprise at least 80%, 85%, 90%, 95% and preferably at least 98% NOTCH3$^+$PDGFRβ$^+$ RGS5$^+$ brain mural cells.

As discussed above, in some embodiments, the p75-NGFR$^+$HNK-1$^+$ neural crest (NC) cells are derived from pluripotent stem cells, for example, induced pluripotent stem cells. In one embodiment, the method further comprises culturing human pluripotent cells in E6-CSFD medium for about 15 days to produced p75-NGFR$^+$HNK-1$^+$ NCSCs. NCSCs maintained in E6-CSFD retained neural crest marker expression and did not develop expression of pericyte or mural cell markers.

In general, the method comprises the steps described below in the Examples. Typically, the method begins with culturing or maintaining hPSCs in E8 medium. In some embodiments, this culture step is on coated plates, for example, Matrigel™ coated plates. The Examples below disclose a preferred method of singularizing the cells using Accutase and preferred seeding densities. As used herein, the terms "E8 culture medium" and "E8" are used interchangeably and refer to a chemically defined culture medium comprising or consisting essentially of DF3S supplemented by the addition of insulin (20 μg/mL), transferrin (10.67 ng/mL), human FGF2 (100 ng/mL), and human TGFβ1 (Transforming Growth Factor Beta 1) (1.75 ng/mL). The medium can be prepared based on the formula in previous publication (Chen et al., (2011) Nature Methods.

8(4), 424-429). As an alternative, the medium is also available from ThermoFisher/Life Technologies Inc. as Essential 8, or from Stem Cell Technologies as TeSR-E8.

Further differentiation steps include using E6 medium that is described herein and in U.S. Patent Publication No. 2014/0134732. Preferably, the chemically defined medium comprises DMEM/F-12. E6 medium contains DMEM/F12; L-ascorbic acid-2-phosphate magnesium (64 mg/1); sodium selenium (14 μg/1); insulin (20 mg/1); $NaHCO_3$ (543 mg/1); and transferrin (10.7 mg/1). E6-CSFD is E6 medium supplemented with CHIR99021, SB431542, FGF2, dorsomorphin, and heparin. Suitable ranges of the factors for inclusion in E6 medium to produce E6-CSFD media includes, for example, about 0.5-5 μM CHIR99021 (preferably 1 μM), a GSK3I3 inhibitor to promote WNT signaling; 5-20 μM SB431543 (preferably 10 μM), an ALK5 antagonist to inhibit Activin/Nodal/TGFβ signaling; 5-100 ng/ml FGF2 (preferably 10 ng/mL); about 0.5-2 μM dorsomorphin (preferable 1 μM), a BMP type I receptor inhibitor; and about 2-200 μg/ml heparin (preferably 22.5 μg/ml). One exemplary formulation of E6-CSFD is 1 μM CHIR99021; 10 μM SB431543; 10 ng/mL FGF2 (E6-CSF); and 1 μM CHIR99021, 1 μM dorsomorphin, and 22.5 μg/ml heparin.

One would then culture the in vitro hPSCs described above in E6-CSFD medium for about 15 days to produce a population comprising NCSCs. Suitable, the cells can be cultured for at least 15 days, and can be maintained in culture to about 60 days. One would then typically sort and re-plate the NCSC cells, which express HNK-1 and p75-NGFR (e.g., p75-$NGFR^+$$HNK$-$1^+$ NCSCs).

In one embodiment, the method further comprises differentiating the p75-$NGFR^+$$HNK$-$1^+$NSCs from human pluripotent stem cells. The method comprises culturing hPSC in E6-CSFD medium for about 15 days to produced p75-$NGFR^+$$HNK$-$1^+$ NCSC cells, subsequently sorting p75-$NGFR^+$ cells from the population and re-plating the p75-$NGFR^+$ cells of step to produce a population of p75-$NGFR^+$ NCSCs. Methods of sorting the p75-$NGFR^+$ cells are known to one skilled in the art and include, but are not limited to, fluorescence activated cell sorting (FACS) and magnetic-activated cell sorting (MACS), among others. A preferred method of sorting the cells is MACS.

The population of cells produced from hPSCs is a p75-$NGFR^+$$HNK$-$1^+$$AP$-$2^+$ NCSCs which are able to be maintained in culture, e.g., the cells are able to double at least 5 times in culture and still maintain expression p75-$NGFR^+$, HNK-$1^+$, and AP-$2^+$ within the cells. These NCSCs are able to be maintained in culture for at least five passages and maintain p75-$NGFR^+$$HNK$-$1^+$$AP$-$2^+$ marker expression and do not express pericyte or mural cell markers (e.g., $NG2^-$, $PDGFR\beta^-$, etc). These NCSCs produced by the method described herein are able to maintain the potential to differentiate into neurons and mesenchymal cells, as demonstrated in the Examples below.

The p75-$NGFR^+$$HNK$-$1^+$ NCSCs may be further cultured and passaged for at least 60 days. The Examples below describe suitable hPSC lines. The human pluripotent stem cells may be embryonic stem cells or induced pluripotent stem cells (iPSCs). The present invention is also meant to employ iPSC lines developed from individual patients or disease models.

As used herein, "pluripotent stem cells" appropriate for use according to a method of the invention are cells having the capacity to differentiate into cells of all three germ layers. Suitable pluripotent cells for use herein include human embryonic stem cells (hESCs) and human induced pluripotent stem cells (iPSCs). As used herein, "embryonic stem cells" or "ESCs" mean a pluripotent cell or population of pluripotent cells derived from an inner cell mass of a blastocyst. See Thomson et al., *Science* 282:1145-1147 (1998). These cells express Oct-4, SSEA-3, SSEA-4, TRA-1-60 and TRA-1-81 and appear as compact colonies having a high nucleus to cytoplasm ratio and prominent nucleolus. ESCs are commercially available from sources such as WiCell Research Institute (Madison, Wis.). As used herein, "induced pluripotent stem cells" or "iPSCs" mean a pluripotent cell or population of pluripotent cells that may vary with respect to their differentiated somatic cell of origin, that may vary with respect to a specific set of potency-determining factors and that may vary with respect to culture conditions used to isolate them, but nonetheless are substantially genetically identical to their respective differentiated somatic cell of origin and display characteristics similar to higher potency cells, such as ESCs. See, e.g., Yu et al., *Science* 318:1917-1920 (2007), incorporated by reference in its entirety. Induced pluripotent stem cells exhibit morphological properties (e.g., round shape, large nucleoli and scant cytoplasm) and growth properties (e.g., doubling time of about seventeen to eighteen hours) akin to ESCs. In addition, iPSCs express pluripotent cell-specific markers (e.g., Oct-4, SSEA-3, SSEA-4, Tra-1-60 or Tra-1-81, but not SSEA-1). Induced pluripotent stem cells, however, are not immediately derived from embryos. As used herein, "not immediately derived from embryos" means that the starting cell type for producing iPSCs is a non-pluripotent cell, such as a multipotent cell or terminally differentiated cell, such as somatic cells obtained from a post-natal individual.

In one embodiment, the disclosure provides a method of creating a population of $NOTCH3^+$$PDGFR\beta^+$$RGS5^+$ brain mural cells comprising: a) culturing hPSCs in E6-CSFD medium for about 15 days to produce p75-$NGFR^+$$HNK$-$1^+$ NCSCs, b) sorting p75-$NGFR^+$ cells and re-plating the p75-$NGFR^+$ cells of step (a) to produce a population of p75-$NGFR^+$ NCSCs; c) activating Notch signaling in the sorted p75-$NGFR^+$$HNK$-$1^+$ NCSCs of step (b), and d) culturing the Notch-activated NC cells in serum free medium for a sufficient time to differentiate $NOTCH3^+$ $PDGFR\beta^+$$RGS5^+$ brain mural cells. A sufficient amount of time is about six days, and optionally between two and ten days The present invention also provides an in vitro derived population of $NOTCH3^+$$PDGFR\beta^+$$RGS5^+$ brain mural cells. The $NOTCH3^+$$PDGFR\beta^+$$RGS5^+$ brain mural cells may be derived from any of the methods described herein. The mural cells may be capable of doubling at least 5 times in culture. The population of cells produced may also express one or more additional mural cell markers, for example, TBX2, endogenous Notch3, FOXS1 and HEYL. In some aspects, the $NOTCH3^+$$PDGFR\beta^+$$RGS5^+$ brain mural cells population also may be capable of differentiating further into brain pericytes and vascular smooth muscle cells. Such cells may express additional mural and/or pericyte gene markers including by way of example and not limitation HEYL, HES4, TBX2, FOXS1, FOXF2, and FOXC1, PDGFRB, RGS5, NDUFA4L2, KCNJ8, ABCC9, HIGD1B, IGFBP7, PLXDC1, CSPG4, ADAMTS1, FOXD1, GJA4, PTGIR, and MCAM (CD146).

In some aspects, the $NOTCH3^+$$PDGFR\beta^+$$RGS5^+$ brain mural cells population also may be capable of forming functional $K_{ATP}$ channels and expressing subunits of the $K_{ATP}$ channel including, but not limited to KCNJ8 and ABCC9.

In some aspects, the $NOTCH3^+$$PDGFR\beta^+$$RGS5^+$ brain mural cells population also may be capable of forming producing extracellular matrix and expressing extracellular matrix genes, including, but not limited to FN1, COL4A1, COL4A2, COL1A1, and LAMA4.

In some aspects, the NOTCH3$^+$PDGFRβ$^+$RGS5$^+$ brain mural cells population also may express human species-specific genes, including but not limited to SLC6A12; and lack expression of mouse species-specific genes, including but not limited to VTN.

The present disclosure also provides a blood brain barrier model comprising the population of NOTCH3$^+$PDGFRβ$^+$ RGS5$^+$ brain mural cells, a permeable membrane and brain microvascular endothelial cells (BMECs) (derived from hPSCs, or primary cultures or cell lines), wherein the BBB model is capable of forming tight junctions.

The NOTCH3$^+$PDGFRβ$^+$RGS5$^+$ brain mural cells can be used for making in vitro models of the BBB. For example, co-culture of BMECs with brain mural cells may improve the BMEC phenotype in co-culture systems, stabilize endothelial cell cord formation in vitro, and induce BMEC properties in primary and hematopoietic stem cell-derived endothelial cells. Thus, the mural cells described herein can be used for producing hPSC-derived BBB models. These BBB models offer the capability for screening of CNS-penetrant therapeutics and can be used to investigate BBB contributions to human disease using patient-derived induced pluripotent stem cells (iPSCs) to derive the cells. Further, for patient-specific modeling of the healthy and diseased BBB, it is paramount to generate mural cells from human iPSCs. The brain mural cells may be used to induce blood-brain barrier (BBB) properties in BMECs in a BBB model, including barrier enhancement and reduction of transcytosis. Incorporating these mural cells with iPSC-derived BMECs, astrocytes, and neurons, one can form an isogenic human NVU model useful for the study of the BBB in CNS health, disease, and therapy.

Use of the mural cells derived herein can be used in blood brain barrier models, for example, those that are described in the art, including, for example, U.S. Ser. No. 13/793,466 (Publication US2017/025935), Ser. No. 13/218,123 (U.S. Pat. No. 8,293,495) and Ser. No. 16/092,450 (Publication US2019/0093084) are drawn to related technology and should be incorporated by reference herein. U.S. Ser. No. 13/218,123 discloses a preferred method of creating an isogenic BBB model (i.e., all of the cell types present are derived for a single patient iPSC line), which comprises BMECs, neurons, and astrocytes, with the use of pericytes in the methods described being able to result in functional improvements to the models. U.S. Ser. No. 13/793,466 discloses an improved BBB model that incorporates retinoic acid (RA). Both of these disclosures provide context for the use of the mural cells of the present invention. Brain mural cells can thus be used to enhance BBB phenotypes in BMECs in these modeling systems.

Mural cells may be co-cultured in a Transwell system (e.g., polystyrene transwell filters with a 0.4 μm pore size) with iPSC-derived BMECs in endothelial cell (EC) medium without FGF2. The transwell coculture system has an upper compartment separated by a Transwell insert containing a microporous semi-permeable membrane that separates the cells in the upper compartment (e.g., CD31$^+$ iPSC-derived BMECs) from the cells in the lower compartment (e.g., the mural cells of the present invention). Suitable EC medium are known in the art and commercially available (e.g., available from Promocell, R&D Systems, Sigma-Aldrich, ScienCell Research Laboratories, Lonza, among others).

Alternatively, mural cells may be co-cultured in direct contact with other cell types, including, for example, endothelial cells, BMECs, astrocytes, and/or neurons. The resulting co-culture models may take the form of cords, networks, aggregates, or "spheroids". For example, mural cells may be co-cultured with HUVECs to form self-organized aggregates.

All references, patents and patent applications disclosed herein are incorporated by reference with respect to the subject matter for which each is cited, which in some cases may encompass the entirety of the document.

It should be apparent to those skilled in the art that many additional modifications beside those already described are possible without departing from the inventive concepts. In interpreting this disclosure, all terms should be interpreted in the broadest possible manner consistent with the context. Variations of the term "comprising" should be interpreted as referring to elements, components, or steps in a non-exclusive manner, so the referenced elements, components, or steps may be combined with other elements, components, or steps that are not expressly referenced. Embodiments referenced as "comprising" certain elements are also contemplated as "consisting essentially of" and "consisting of" those elements. The term "consisting essentially of" and "consisting of" should be interpreted in line with the MPEP and relevant Federal Circuit's interpretation. The transitional phrase "consisting essentially of" limits the scope of a claim to the specified materials or steps "and those that do not materially affect the basic and novel characteristic(s)" of the claimed invention. "Consisting of" is a closed term that excludes any element, step or ingredient not specified in the claim.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of" "Consisting essentially of," when used in the claims, shall have its ordinary meaning as used in the field of patent law.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviations, per practice in the art. Alternatively, "about" with respect to the compositions can mean plus or minus a range of up to 20%, preferably up to 10%, more preferably up to 5%.

The present invention has been described in terms of one or more preferred embodiments, and it should be appreciated that many equivalents, alternatives, variations, and modifications, aside from those expressly stated, are possible and within the scope of the invention.

EXAMPLES

Notch3 Directs Differentiation of Brain Mural Cells From Human Pluripotent Stem Cell-Derived Neural Crest Brain pericytes and vascular smooth muscle cells, collectively termed mural cells, regulate development and function of the blood-brain barrier (BBB) and control brain blood flow. Unlike the mesoderm-derived mural cells of other organs, forebrain mural cells are derived from the neural crest. Molecular signals controlling this differentiation process are poorly understood, with loss of function experiments suggesting roles for TGF-β, PDGF, and Notch signaling. Furthermore, existing in vitro models of human brain mural cells derived both from primary cultures and human pluripotent stem cells (hPSCs) have markedly reduced expression of key mural cell genes, including NOTCH3, compared to in vivo samples, and require serum-supplemented culture media. Thus, we sought to determine whether activation of Notch3 or Notch1 in hPSC-derived neural crest could direct the differentiation of brain mural cells with an improved transcriptional profile.

We generated a bicistronic lentiviral vector encoding the human Notch3 and Notch1 intracellular domain and green fluorescent protein (N3ICD-GFP and N1ICD-GFP respectively). We transduced p75-NGFR$^+$HNK-1$^+$ neural crest cells derived from hPSCs with N3ICD-GFP lentivirus or GFP-only lentivirus in serum-free E6 medium. Compared to GFP-transduced neural crest, N3ICD-GFP-transduced cells exhibited upregulated expression of the mural cell transcripts PDGFRB, RGS5, FOXS1, TBX2, and HEYL. Similar results were obtained with N1ICD-GFP. In contrast, transduction of TBX2-GFP did not produce such an effect. In N3ICD-GFP-transduced cells, we observed increased protein-level expression of PDGFRβ and both full-length and cleaved Notch3. We additionally evaluated the ability of the resulting cells to self-assemble with endothelial cells (ECs) in a cord-formation assay and to induce BBB properties in ECs.

In this Example, the inventors found that expression levels of NOTCH3 and canonical transcriptional targets of Notch signaling were very low in existing hPSC-derived brain pericyte-like cells compared to human brain pericytes in vivo. The inventors found that activation of Notch3 signaling directed the differentiation of hPSC-derived neural crest to brain mural cells under serum-free conditions. Because ligand-induced activation of Notch signaling requires complex cell-cell interactions and ligand endocytosis, the inventors activated Notch signaling by lentiviral overexpression of the human Notch3 intracellular domain in neural crest cells maintained in serum-free medium. The resulting cells were PDGFRβ$^+$ and displayed robust upregulation of the mural cell genes HEYL, RGS5, TBX2, and FOXS1. Supplementation of additional molecular factors did not substantially improve the transcriptional profile of the resulting cells. Thus, this work suggests that Notch3 signaling is sufficient to direct differentiation of neural crest to brain mural cells, and establishes a new, serum-free protocol for generation of brain mural cells from hPSCs.

This data suggests that activation of Notch3 signaling is sufficient to direct differentiation of neural crest to brain mural cells, and that multiple brain mural cell-associated transcription factors are downstream of Notch3 signaling. Established herein is a new, serum-free differentiation protocol for generation of hPSC-derived brain mural cells for downstream in vitro modeling applications.

Results

Transcriptome Analysis of hPSC-Derived Brain Pericyte-Like Cells

Figure 6:
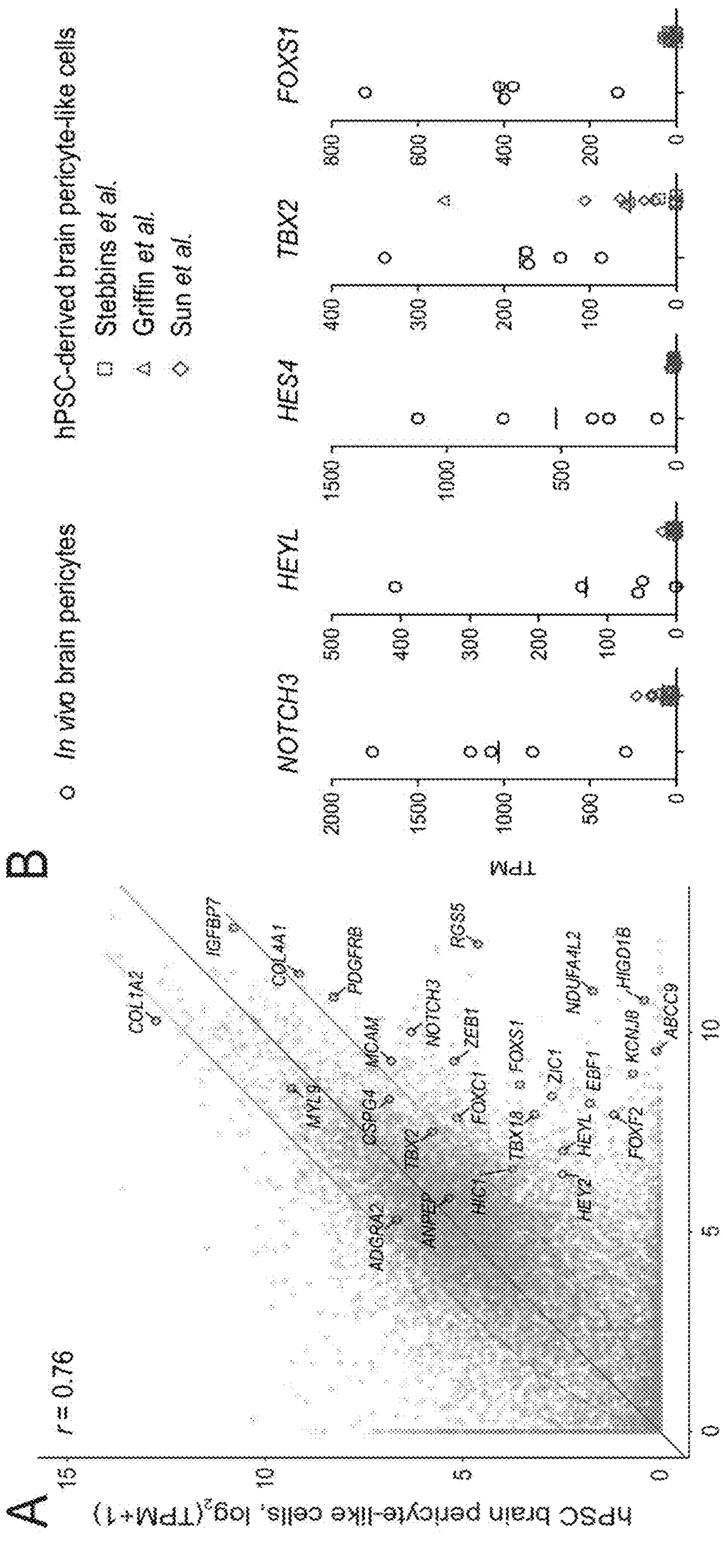
FIG. 6. Comparison of human brain pericytes in vivo and hPSC-derived brain pericyte-like cells. (A) Comparison of protein-coding transcript abundances in hPSC-derived brain pericyte-like cells versus in vivo human brain pericytes. Data for hPSC-derived brain pericyte like cells were generated by averaging transcripts per million (TPM) across 11 bulk RNA-seq datasets: 5 datasets from (38), 3 datasets from (40), and 4 datasets from (41) (Table 3). Data for in vivo human brain pericytes were obtained from a previous meta-analysis of 5 single cell RNA-seq datasets (36). The Pearson correlation coefficient r is shown. Genes of interest are annotated in red (transcription factors) or blue (others). Orange lines represent fold changes of ±2. (B) Transcript abundance of selected genes. Abundances for each of the five in vivo human brain pericyte datasets are indicated with black circles. Abundances for each of the hPSC-derived brain pericyte-like cell datasets are indicated with blue squares (38), green triangles (40), and red diamonds (41). Bars indicate mean values. TPM: transcripts per million.
Figure 7:
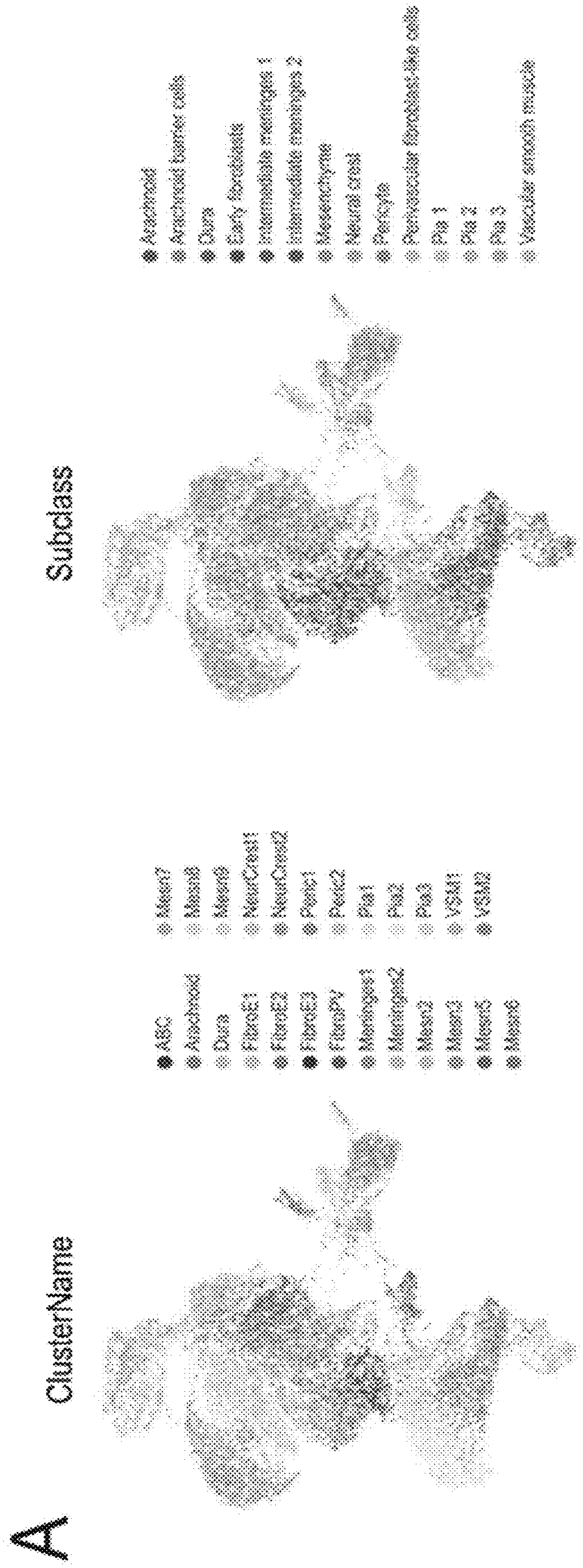
FIG. 7. Markers of murine neural crest, mural cells, and other mesenchymal derivatives. (A) UMAP plots of all single cells colored by authors' ClusterName, Subclass, Age, and PseudoAge annotations. (B) Dot plot of gene expression in cell Subclasses. Neural crest, pan-mesenchymal, fibroblast, pan-mural, pericyte, and VSMC marker genes are shown. Color indicates expression level and dot size indicates the percent of cells in the indicated Subclass that express a given gene. Data from ref. (93).
Figure 7:
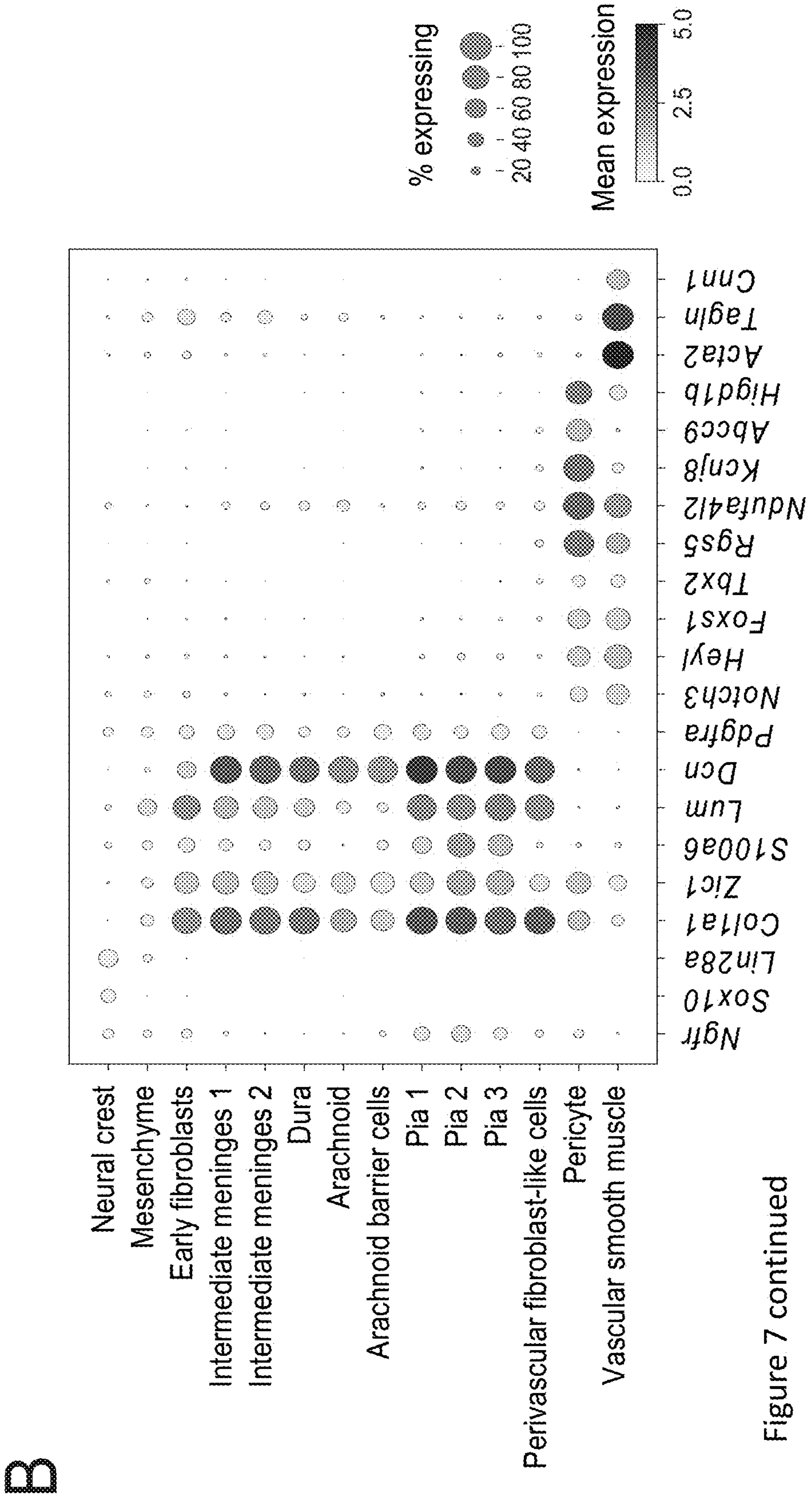

We analyzed RNA-sequencing (RNA-seq) gene expression profiles of brain pericyte-like cells differentiated from hPSCs from three independent studies (38, 40, 41). While methodologies differ slightly, all three protocols proceed through a neural crest intermediate and yield cells with molecular and functional characteristics similar to mural cells. We compared these cells to human brain pericytes in vivo, using single cell RNA-seq data from a previous meta-analysis (36). There was moderate correlation between the transcriptome of hPSC-derived pericyte-like cells and in vivo pericytes, and similar expression of some canonical markers such as PDGFRB, ANPEP, CSPG4, COL4A1, IGFBP7, and MYL9 (FIG. 6A). Compared to in vivo pericytes, however, hPSC-derived pericyte-like cells had markedly lower expression of several key mural cell signaling mediators and transcription factors, including RGS5, NOTCH3, HEYL, HEY2, HES4, TBX2, FOXS1, and FOXF2 (FIG. 6A-B). We previously demonstrated downregulation of many of these same genes in cultured primary human brain pericytes (36), and a murine developmental single cell RNA-seq study supports selective expression of many of these genes in mural cells compared to both neural crest and other mesenchymal derivatives (FIG. 7). These results therefore suggest that key molecular factors for induction and maintenance of the brain mural cell phenotype are absent under traditional culture conditions, and that augmentation of these factors during hPSC differentiation might yield mural cells with improved phenotype.

Overexpression of Notch3 Intracellular Domain as a Strategy to Derive Mural Cells Given low expression of NOTCH3 and Notch target genes (e.g., HEYL, HEY2, HES4) in existing hPSC-derived pericyte-like cells and the known roles of Notch signaling in mural cell development (29), we asked whether overexpression of the human Notch3 intracellular domain (N3ICD) in neural crest cells could direct mural cell differentiation. We also evaluated overexpression of Tbx2, a mural cell-enriched transcription factor with similarly low expression in existing hPSC models. We cloned the portion of the NOTCH3 coding sequence (CDS) corresponding to the intracellular domain, and the TBX2 CDS, into bicistronic lentiviral vectors for GFP coexpression (see Methods) (FIG. 1A-B). As a starting cell type, we used neural crest cells differentiated from hPSCs according to a previously-established protocol (38). After 15 days of differentiation in E6-CSFD medium, we selected p75$^+$ cells via magnetic-activated cell sorting (MACS), resulting in a homogenous population of p75$^+$HNK-1$^+$ neural crest cells that were briefly expanded prior to transduction (FIG. 1A, C). We transduced neural crest cells with GFP-only, N3ICD-GFP, or TBX2-GFP lentiviruses, and after 6 days, either analyzed the resulting populations or performed fluorescence-activated cell sorting (FACS) to isolate $GFP^+$ cells.

Figure 8:
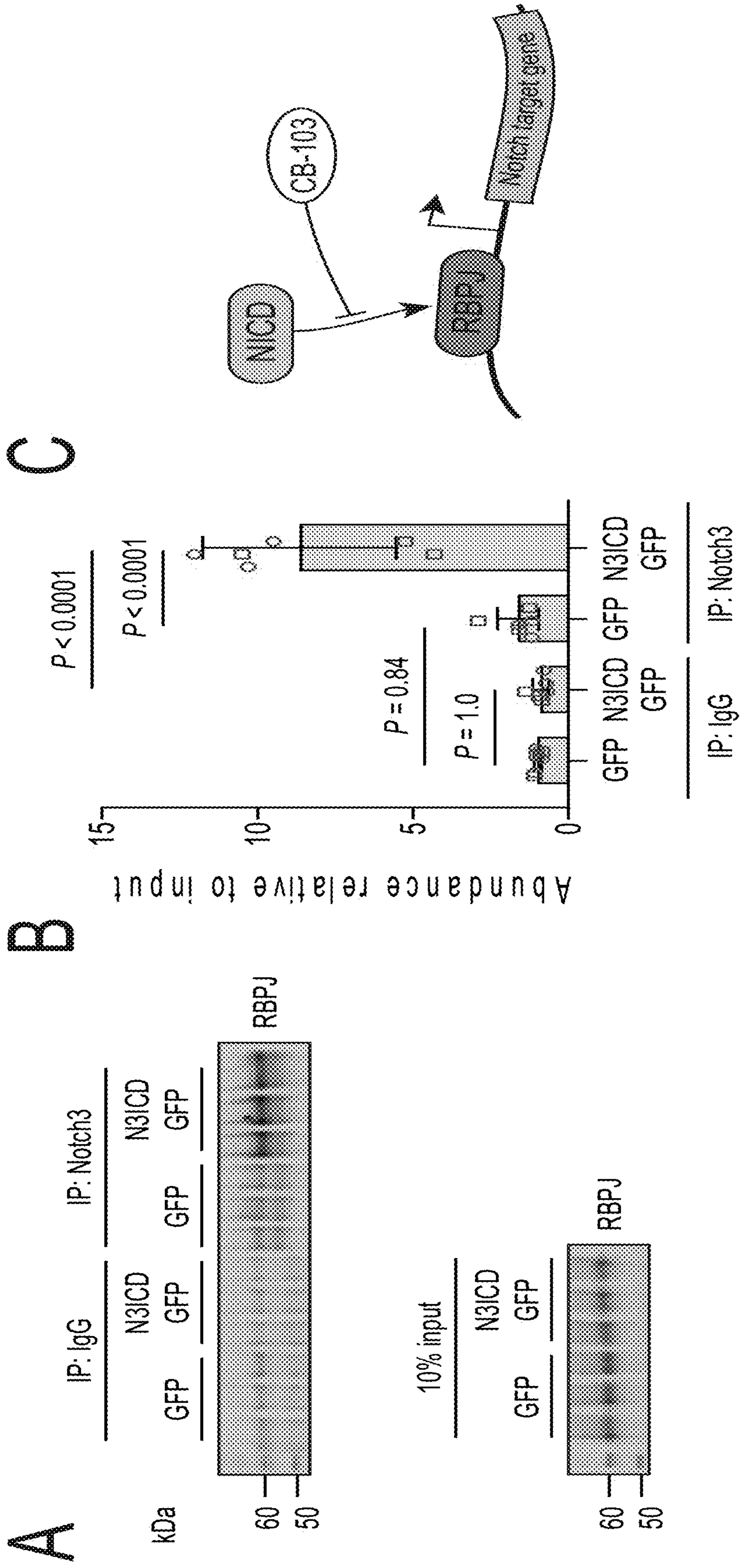
FIG. 8. Notch-dependence of observed transcriptional changes. (A) Western blots of isotype control IgG and Notch3 immunoprecipitates (top) and input controls (bottom) from cells 6 days after transduction with GFP or N3ICD-GFP lentiviruses. Membranes were probed with the RBPJ antibody. (B) Quantification of Western blots from coimmunoprecipitation assay described in (A). Band intensities from immunoprecipitates were normalized to respective input control band intensities. Points represent replicate wells from two differentiations of the H9 hPSC line, each differentiation indicated with a different color. Bars indicate mean values±SD, with values normalized within each differentiation such that the mean of the GFP, IP: IgG condition equals 1. P-values: two-way ANOVA on unnormalized data followed by Tukey's HSD test. (C) Schematic of the mechanism of action of CB-103, a small molecule inhibitor of the Notch transcriptional activation complex (43). NICD: Notch intracellular domain. (D) RT-qPCR analysis of mural cell gene expression 6 days after transduction of neural crest cells with GFP or N3ICD-GFP lentiviruses. Expression of each gene is shown relative to ACTB expression and normalized to expression in GFP-transduced cells. Points represent replicate wells from a differentiation of the H9 hPSC line and bars indicate mean±SD. P-values: ANOVA followed by Tukey's HSD test.
Figure 8:
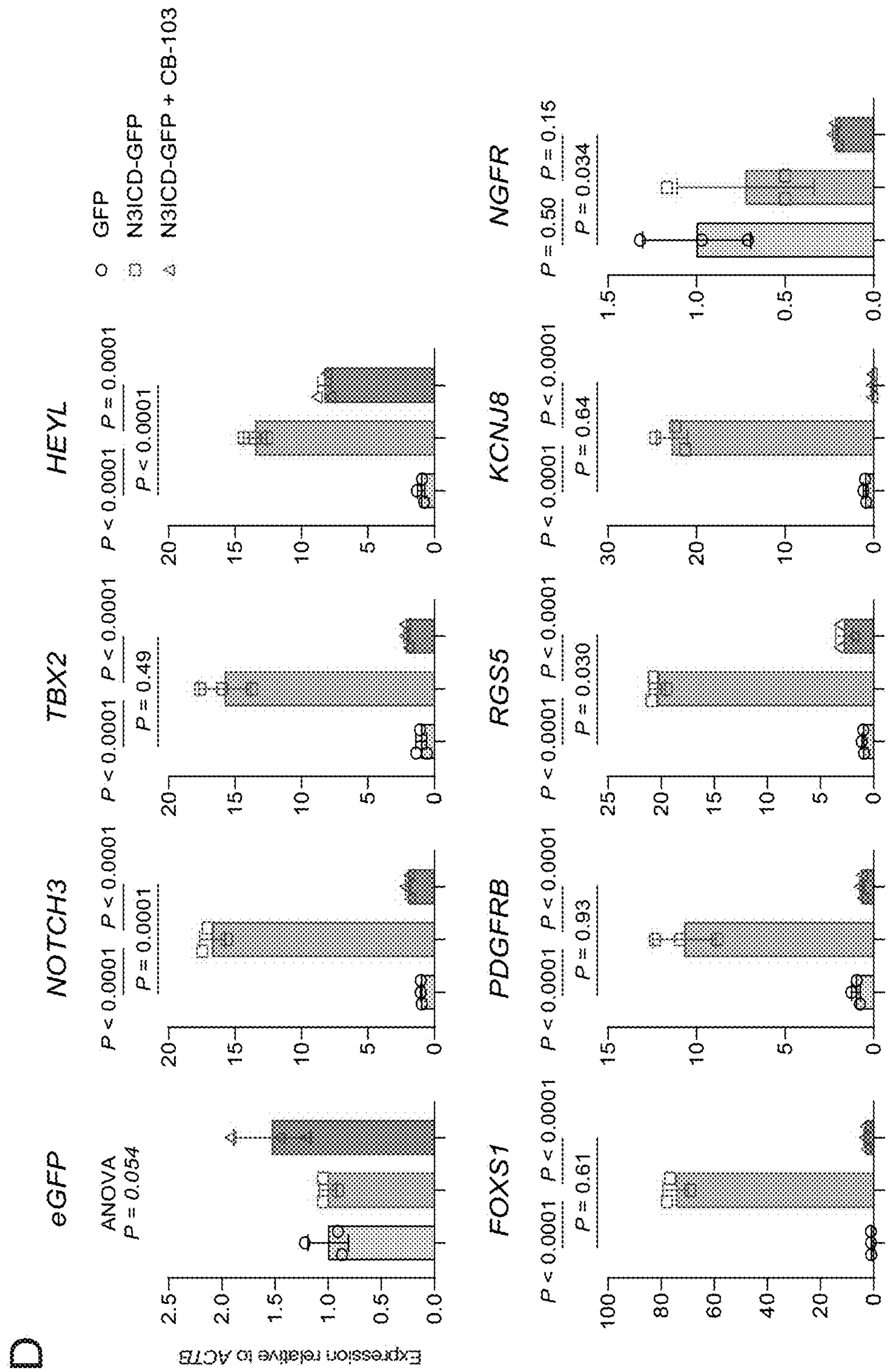
Figure 9:
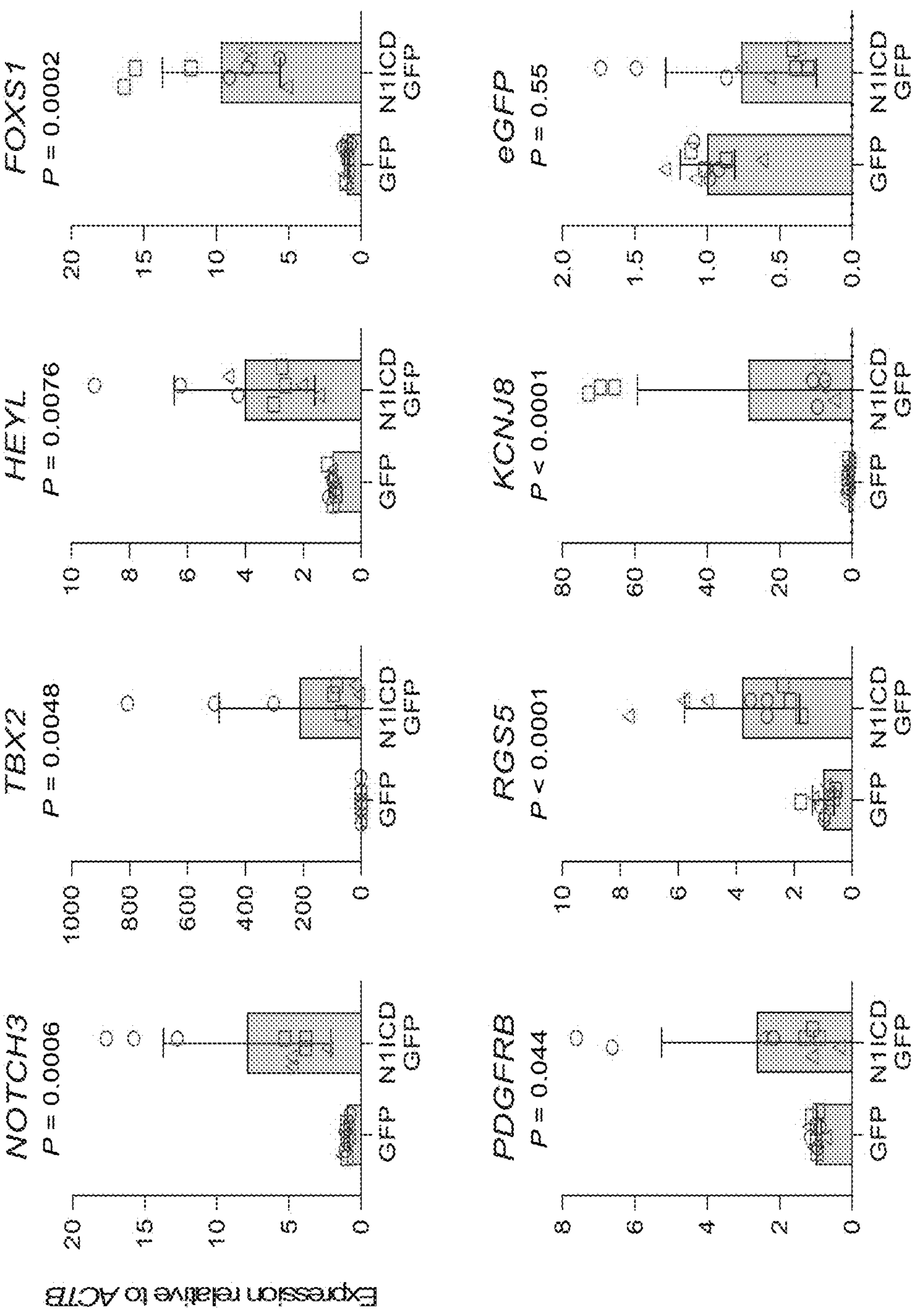
FIG. 9. Transcriptional effects of N1ICD overexpression. RT-qPCR analysis of mural cell gene expression 6 days after transduction of neural crest cells with GFP or N1ICD-GFP lentiviruses. Expression of each gene is shown relative to ACTB expression. Points represent replicate wells from three independent differentiations, two in the H9 hPSC line (circles, triangles) and one in the IMR90-4 hPSC line (squares). Bars indicate mean values±SD, with values normalized within each differentiation such that the mean of the GFP condition equals 1. P-values: two-way ANOVA on unnormalized data.

6 days after lentiviral transduction, N3ICD-GFP-transduced cells had significantly elevated expression of HEYL and endogenous NOTCH3 (using primers targeting the 3' untranslated region, which is not present in transgene-derived transcripts) compared to GFP controls (FIG. 1D). Notably, these cells also had increased expression of other mural cell transcription factors (TBX2, FOXS1) and canonical markers (PDGFRB, RGS5, KCNJ8), suggesting that Notch3 signaling may be sufficient activate a genetic program for mural cell differentiation (FIG. 1D). In contrast, while TBX2-GFP-transduced cells had elevated expression of TBX2, suggesting successful overexpression, and a slight increase in PDGFRB expression, all other mural cell genes evaluated were unchanged versus GFP controls (FIG. 1D). We confirmed that N3ICD-GFP-mediated transcriptional changes occurred via a canonical Notch transactivation mechanism using Notch3-RBPJ coimmunoprecipitation and a loss-of-function experiment with CB-103, a small molecule inhibitor of Notch intracellular domain-RBPJ assembly (43) (FIG. 8). We also asked whether overexpression of an alternative Notch would achieve a similar effect; indeed, N1ICD-GFP-transduced neural crest cells underwent similar transcriptional changes to N3ICD-GFP-transduced cells (FIG. 9). We elected, however, to conduct further experiments using cells derived via N3ICD overexpression, given enrichment of Notch3 compared to other Notch receptors in brain mural cells, and existing loss-of-function studies establishing the necessity of Notch3 for mural cell development (29, 30).

Figure 2:
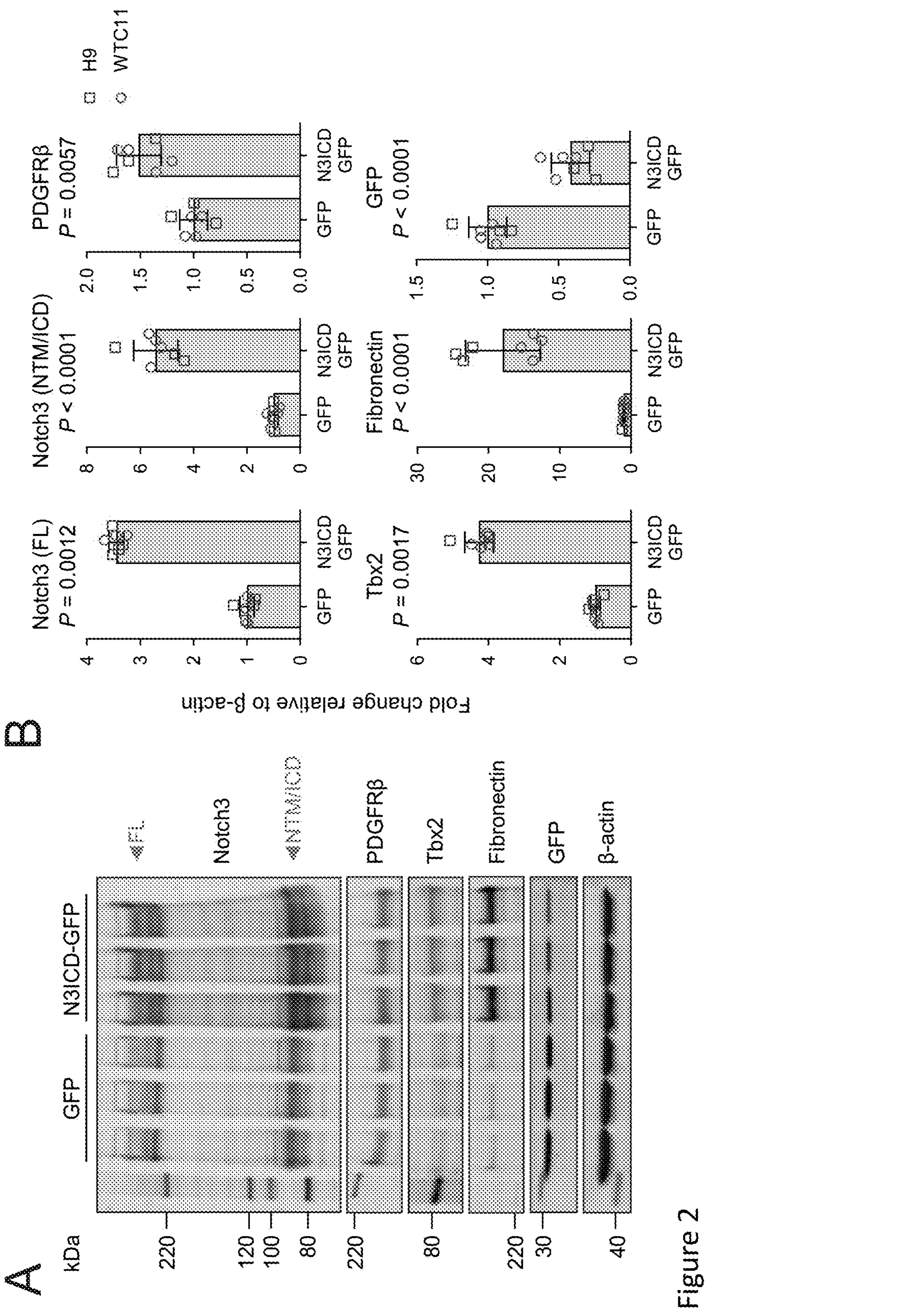
FIG. 2. Results of Notch3 intracellular domain overexpression in neural crest cells. (A) Western blots of cells 6 days after transduction with GFP or N3ICD-GFP lentiviruses. Membranes were probed with Notch3, PDGFRβ, Tbx2, fibronectin, GFP, and β-actin antibodies. On the Notch3 Western blot, arrows indicate the full-length (FL) and Notch transmembrane/intracellular domain (NTM/ICD) bands. (B) Quantification of Western blots. Band intensities were normalized to β-actin band intensities. Points represent replicate wells from two independent differentiations, one in the H9 hPSC line (squares) and one in the WTC11 hPSC line (circles). Bars indicate mean values±SD, with values normalized within each differentiation such that the mean of the GFP condition equals 1. P-values: two-way ANOVA on unnormalized data. (C) Immunocytochemistry analysis of Notch3, PDGFRβ, Tbx2, and fibronectin expression in cells 6 days after transduction with GFP or N3ICD-GFP lentiviruses. Hoechst nuclear counterstain overlaid in all images. Scale bars: 50 (D) Flow cytometry analysis of GFP expression 6 days after transduction of neural crest cells with N3ICD-GFP lentivirus. $GFP^+$ and $GFP^-$ gates are representative of those used to isolate populations via FACS. (E) Immunocytochemistry analysis of GFP and Tbx2 expression in cells expanded in E6 medium for 4 days after FACS. Hoechst nuclear counterstain is overlaid in the GFP images. Scale bars: 100 μm.
Figure 2:
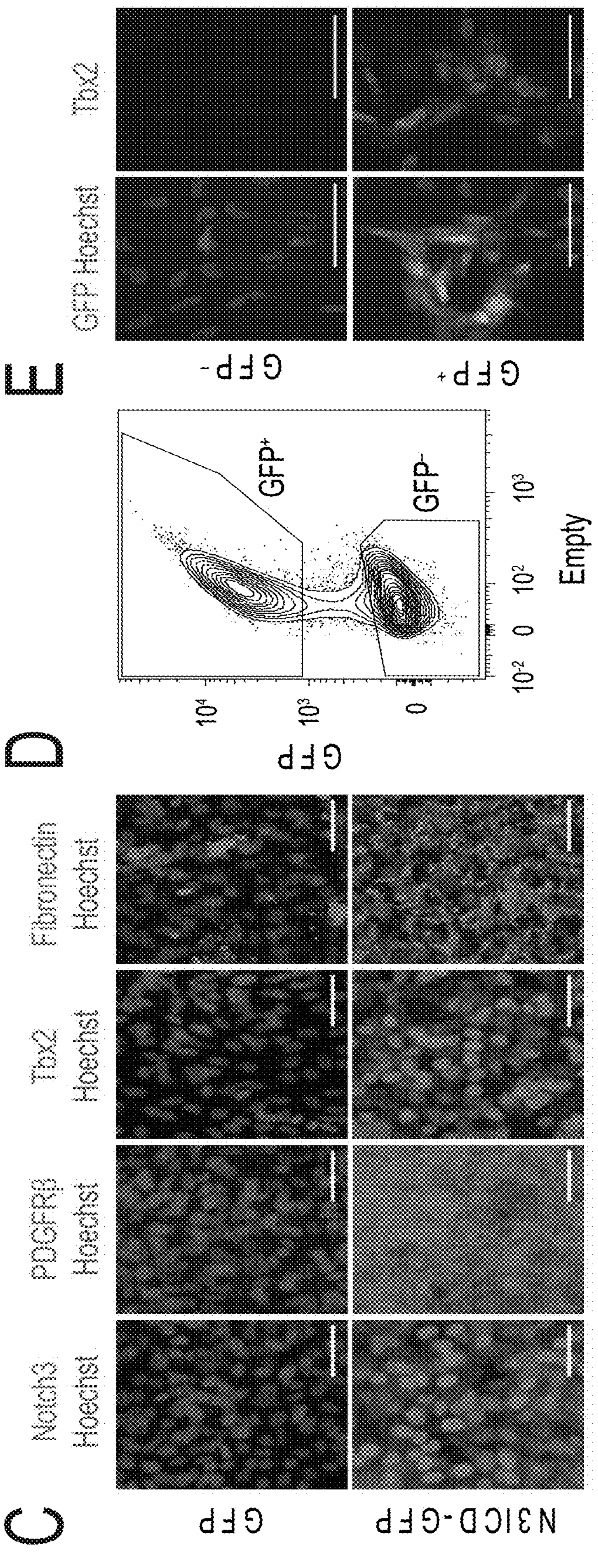
Figure 10:
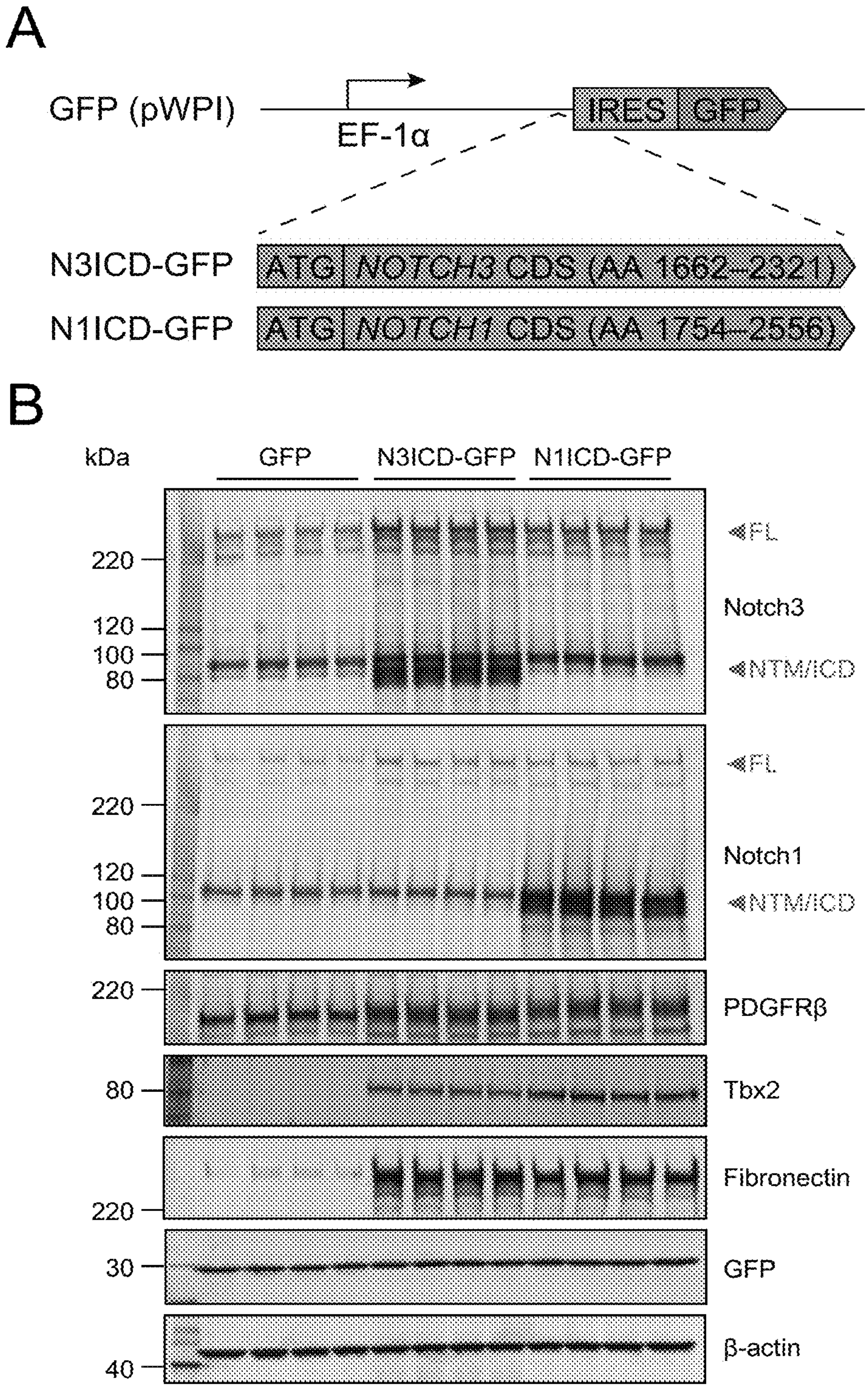
FIG. 10. Comparison of N1ICD and N3ICD overexpression. (A) Schematic of lentiviral overexpression constructs. The parental pWPI vector and N3ICD-GFP are as described in FIG. 1. To generate N1ICD-GFP, a fragment of the human NOTCH1 coding sequence (CDS) encoding the intracellular domain of Notch1 was cloned into pWPI. IRES: internal ribosome entry site; AA: amino acids. (B) Western blots of cells 6 days after transduction with GFP, N3ICD-GFP, or N1ICD-GFP lentiviruses. Membranes were probed with Notch3, Notch1, PDGFRβ, Tbx2, fibronectin, GFP, and β-actin antibodies. On the Notch3 and Notch1 Western blots, arrows indicate the full-length (FL) and Notch transmembrane/intracellular domain (NTM/ICD) bands. (C) Quantification of Western blots. Band intensities were normalized to β-actin band intensities. Points represent replicate wells from a differentiation of the H9 hPSC line. Bars indicate mean values±SD, with values normalized such that the mean of the DMSO condition equals 1. P-values: ANOVA followed by Tukey's HSD test.
Figure 10:
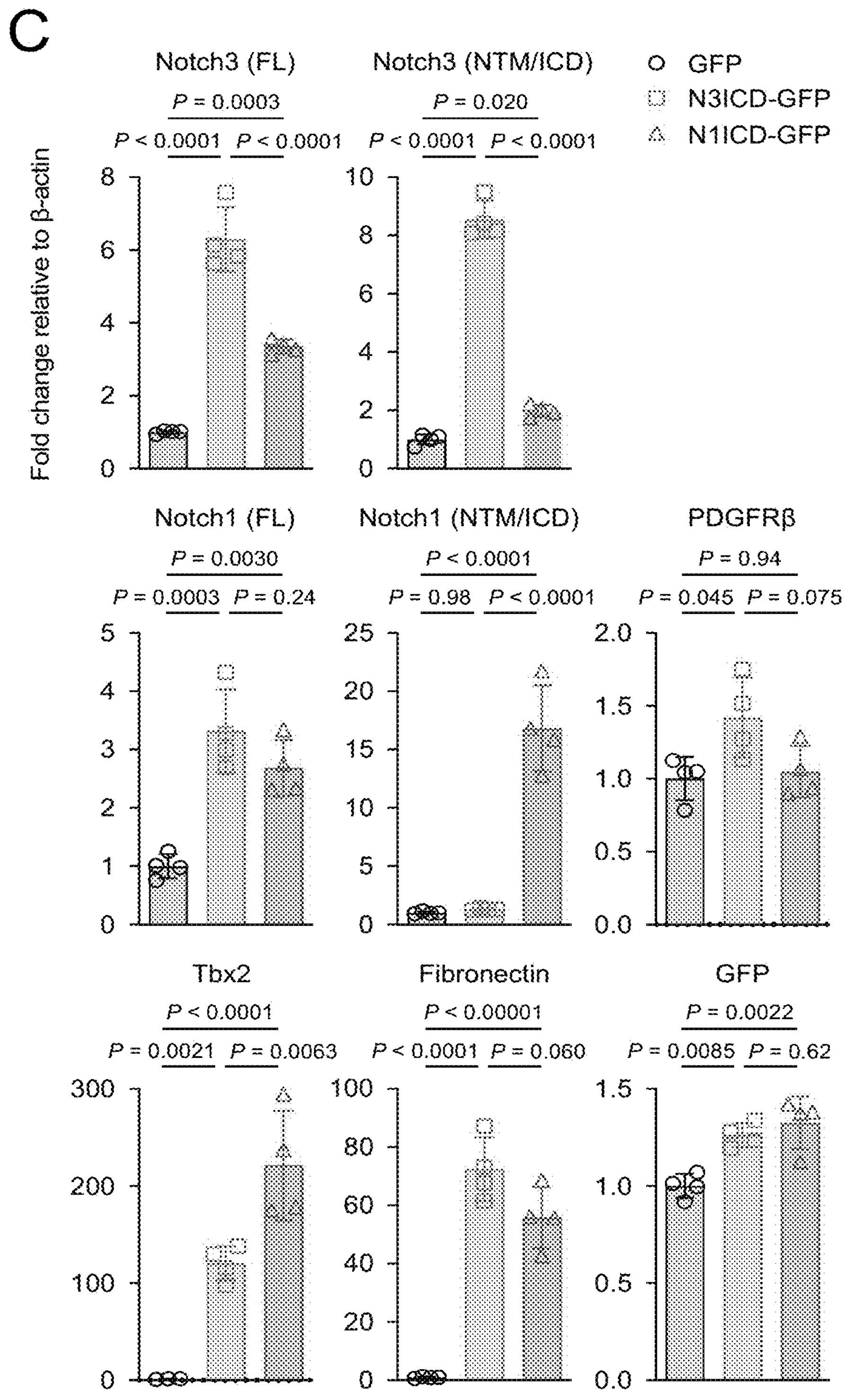

We validated protein-level overexpression of N3ICD via Western blotting with a Notch3 antibody detecting a C-terminal (intracellular domain) epitope. As expected, we observed a significant increase in the intensity of a low molecular weight band corresponding to the Notch transmembrane fragment and intracellular domain in N3ICD-GFP-transduced cultures compared to GFP-transduced cultures (FIG. 2A-B). A high molecular weight band corresponding to full-length Notch3 also had increased abundance in N3ICD-GFP-transduced cultures, suggestive of positive feedback and consistent with enrichment of Notch3 in brain mural cells compared to neural crest in vivo (44-46). The canonical mural cell marker PDGFRβ and transcription factor Tbx2 were also upregulated in N3ICD-GFP-transduced cultures, despite lower GFP abundance, reflective of slightly lower transduction efficiency by N3ICD-GFP lentivirus compared to GFP lentivirus (FIG. 2A-B). We also observed a marked increase in fibronectin abundance in N3ICD-GFP-transduced cultures (FIG. 2A-B), consistent with human brain mural cell expression of FN1 in vivo (36). Immunocytochemistry corroborated these findings and revealed clear nuclear localization of Notch3 and Tbx2 in N3ICD-GFP-transduced cells (FIG. 2C). Consistent with transcript-level observations, N1ICD overexpression also achieved similar effects to N3ICD on the protein level (FIG. 10). Together, these results suggest that activation of Notch signaling in neural crest cells is sufficient to drive mural cell differentiation.

Molecular Properties of Cells Derived Via N3ICD Overexpression

Figure 11:
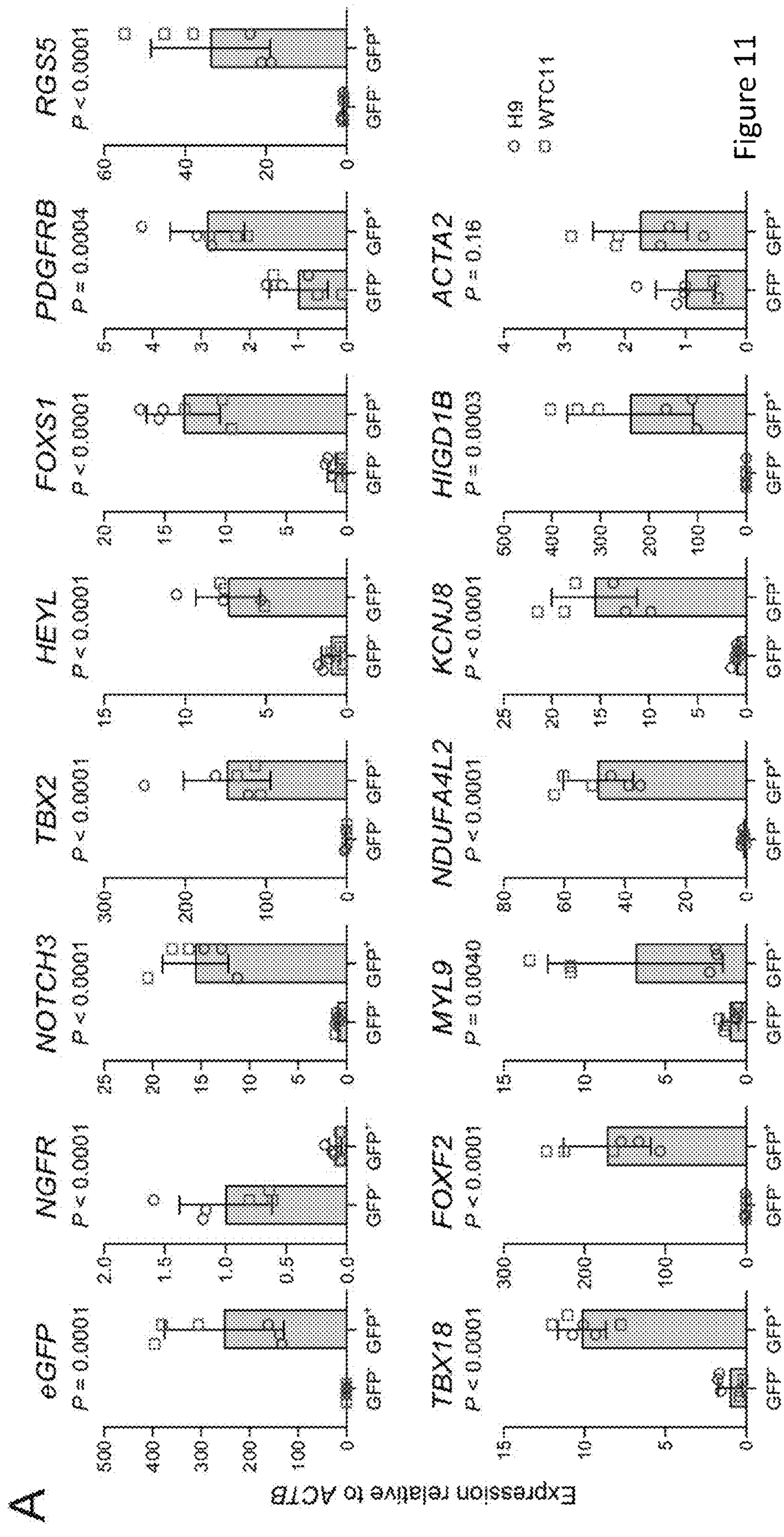
FIG. 11. Cell-autonomous and time-dependent effects of N3ICD overexpression. (A) RT-qPCR analysis of $GFP^-$ and $GFP^+$ cells isolated via FACS 6 days after transduction of neural crest cultures with N3ICD-GFP lentivirus. Expression of each gene is shown relative to ACTB expression and normalized to expression in $GFP^-$ cells. NOTCH3 primers target the 3'UTR and thus amplify only endogenous NOTCH3 transcripts. Points represent replicate wells from two independent differentiations, one in the H9 hPSC line (circles) and one in the WTC11 hPSC line (squares). Bars indicate mean values±SD. P-values: Two-way ANOVA. (B) RT-qPCR analysis of $GFP^+$ and $GFP^-$ cells 2, 5, and 10 days after isolation via FACS as described above. Points represent replicate wells from a differentiation of the H9 hPSC line. (C) Immunocytochemistry analysis of GFP, Notch3, Tbx2, PDGFRβ, calponin, SM22α, and α-SMA expression in $GFP^-$ and $GFP^+$ cells 4 days after isolation via FACS as described above. Hoechst nuclear counterstain overlaid in all images. Scale bars: 50 μm.
Figure 11:
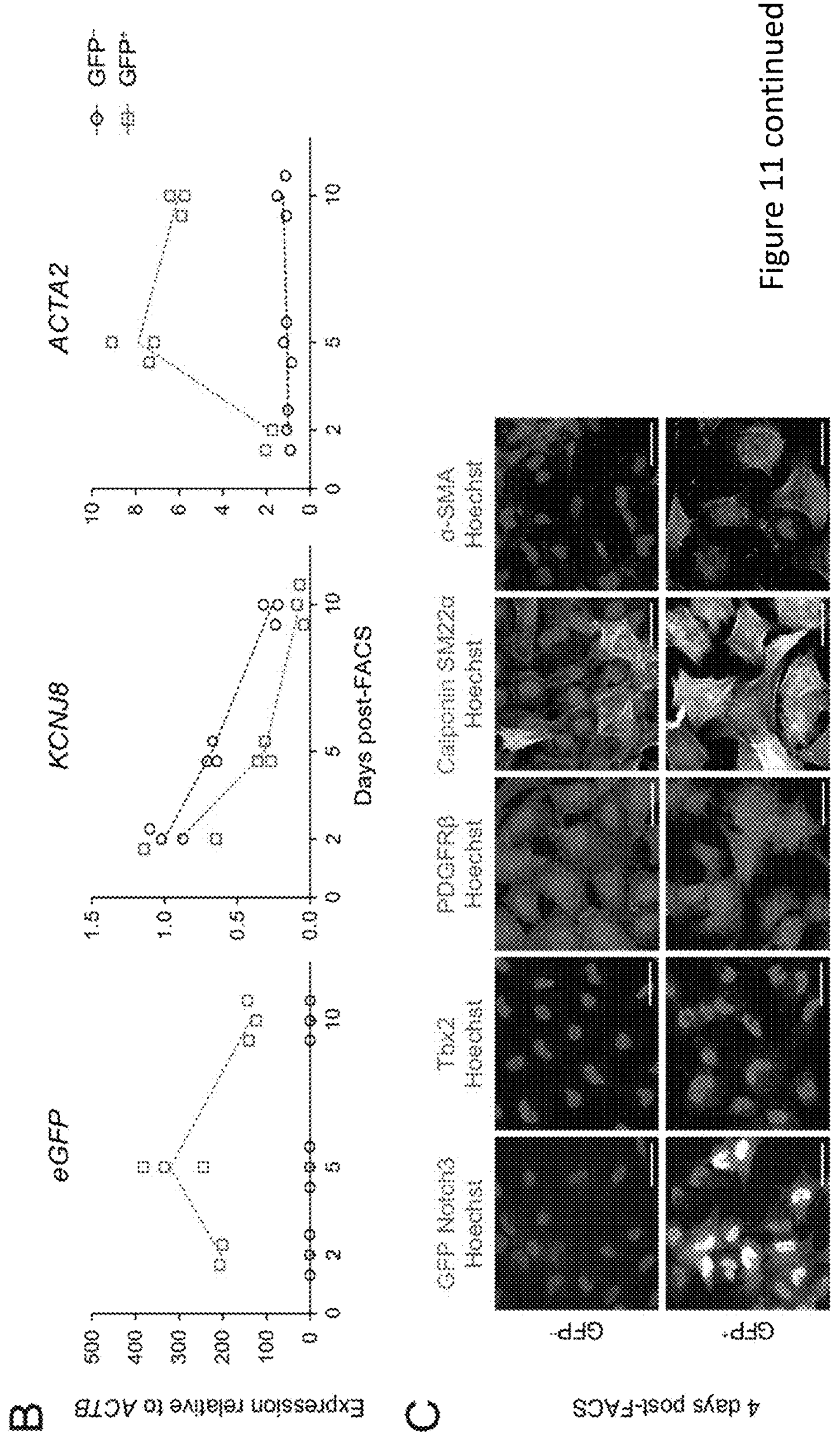

We used FACS to isolate $GFP^+$ and $GFP^-$ cells from cultures 6 days after N3ICD-GFP lentiviral transduction (FIG. 2D). We compared acutely isolated $GFP^+$ and $GFP^-$ cells by RT-qPCR; $GFP^+$ cells had significantly reduced expression of NGFR, consistent with loss of neural crest identity, and significantly higher expression of markers of mesenchyme (e.g., TBX18), mural cells (e.g., NOTCH3, TBX2, HEYL, FOXS1), and pericytes (e.g., KCNJ8), while the VSMC-enriched gene ACTA2 was not differentially expressed (FIG. 11A). Immunostaining conducted 4 days after FACS confirmed that Tbx2 was selectively expressed $GFP^+$ cells (FIG. 2D). Importantly, these results suggest that N3ICD-GFP functions cell-autonomously to direct neural crest-to-mural cell differentiation, and that the resulting cells have molecular hallmarks of pericytes. After briefly expanding the resulting cells in minimal E6 medium, however, we observed marked downregulation of KCNJ8 and upregulation of ACTA2 despite maintained expression of the N3ICD-GFP transgene; at 4 days post-FACS, cells expressed the VSMC-enriched proteins α-SMA, calponin, and SM22α (FIG. 11B-C). Loss of KCNJ8 and induction of these contractile proteins is a phenomenon also observed upon in vitro culture of primary brain pericytes, and suggests that while Notch3 is sufficient to direct initial specification and differentiation of mural cells with pericyte-like marker expression, additional yet-unidentified factors are required for maintenance of pericyte phenotype. Therefore, to further characterize the initial Notch-mediated specification and differentiation process, we focused on acutely isolated $GFP^+$ cells.

Figure 3:
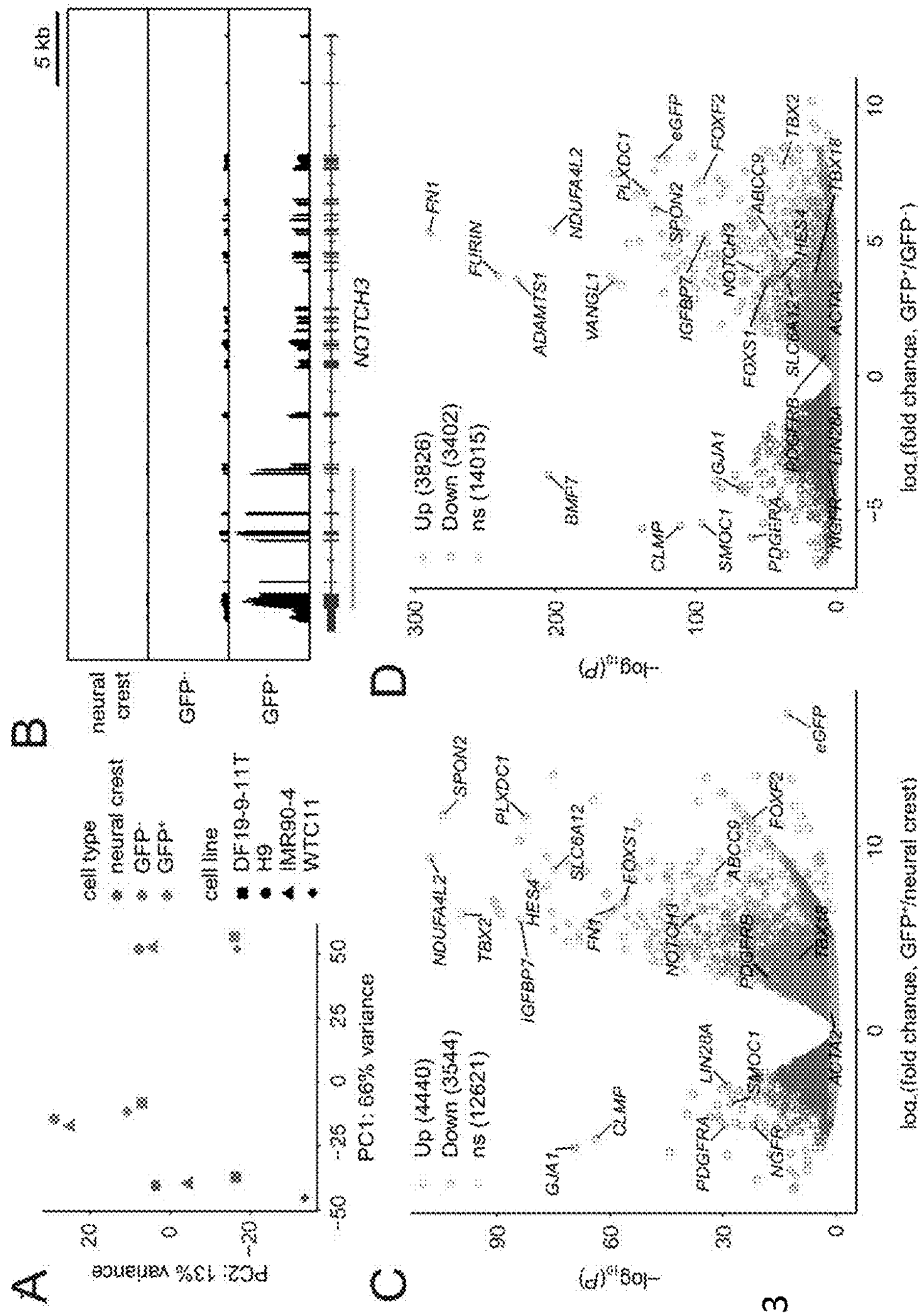
FIG. 3. RNA-seq of neural crest, $GFP^-$, and $GFP^+$ cells. (A) Principal component analysis of whole-transcriptome data after the DESeq2 variance stabilizing transformation. Points are colored by cell type: neural crest (magenta), $GFP^-$ cells (gray), $GFP^+$ cells (green). Data are from four independent differentiations, one each from the DF19-9-11T (squares), H9 (circles), IMR90-4 (triangles), and WTC11 (diamonds) hPSC lines. (B) Representative genome browser plots (from DF19-9-11T-derived neural crest, $GFP^-$, and $GFP^+$ cells) of RNA-seq read alignment to the NOTCH3 gene. The line at bottom indicates the region of NOTCH3 encoding the intracellular domain. (C, D) Differential expression analysis of $GFP^+$ cells compared to neural crest (C) and $GFP^+$ cells compared to $GFP^-$ cells (D). Data are displayed in volcano plots; MA plots are shown in FIG. 13A-B. Differentially expressed genes (adjusted P-values <0.05, DESeq2 Wald test with Benjamini-Hochberg correction) are highlighted, and the numbers of upregulated and downregulated genes are shown in the legends. (E) Transcript abundance (TPM) of selected transcripts. The top row displays expression of transgene (eGFP), total NOTCH3 (encompassing endogenous and transgene-derived transcripts), neural crest markers, the non-mural transcript PDGFRA, and the VSMC-enriched transcript (ACTA2). The second row displays mesenchymal and mural cell transcription factors; the third row displays mural and pericyte markers; the fourth row displays genes encoding components of extracellular matrix. Additional genes are shown in FIG. 13D. (F) Results of Gene Set Enrichment Analysis (GSEA). Gene sets from the KEGG and GO-BP databases enriched in $GFP^+$ cells compared to neural crest (FDR <0.05) are shown. NES: normalized enrichment score. Additional results of GSEA are shown in FIG. 13. (G) Comparison of protein-coding transcript abundances in $GFP^+$ cells versus in vivo human brain pericytes. Data for hPSC-derived brain pericyte like cells were generated by averaging transcripts per million (TPM) across 11 bulk RNA-seq datasets: 5 datasets from (38), 3 datasets from (40), and 4 datasets from (41) (Table 3). Data for in vivo human brain pericytes were obtained from a previous meta-analysis of 5 single cell RNA-seq datasets (36). The Pearson correlation coefficient r is shown. Genes of interest are annotated in red (transcription factors) or blue (others). Orange lines represent fold changes of ±2.
Figure 3:
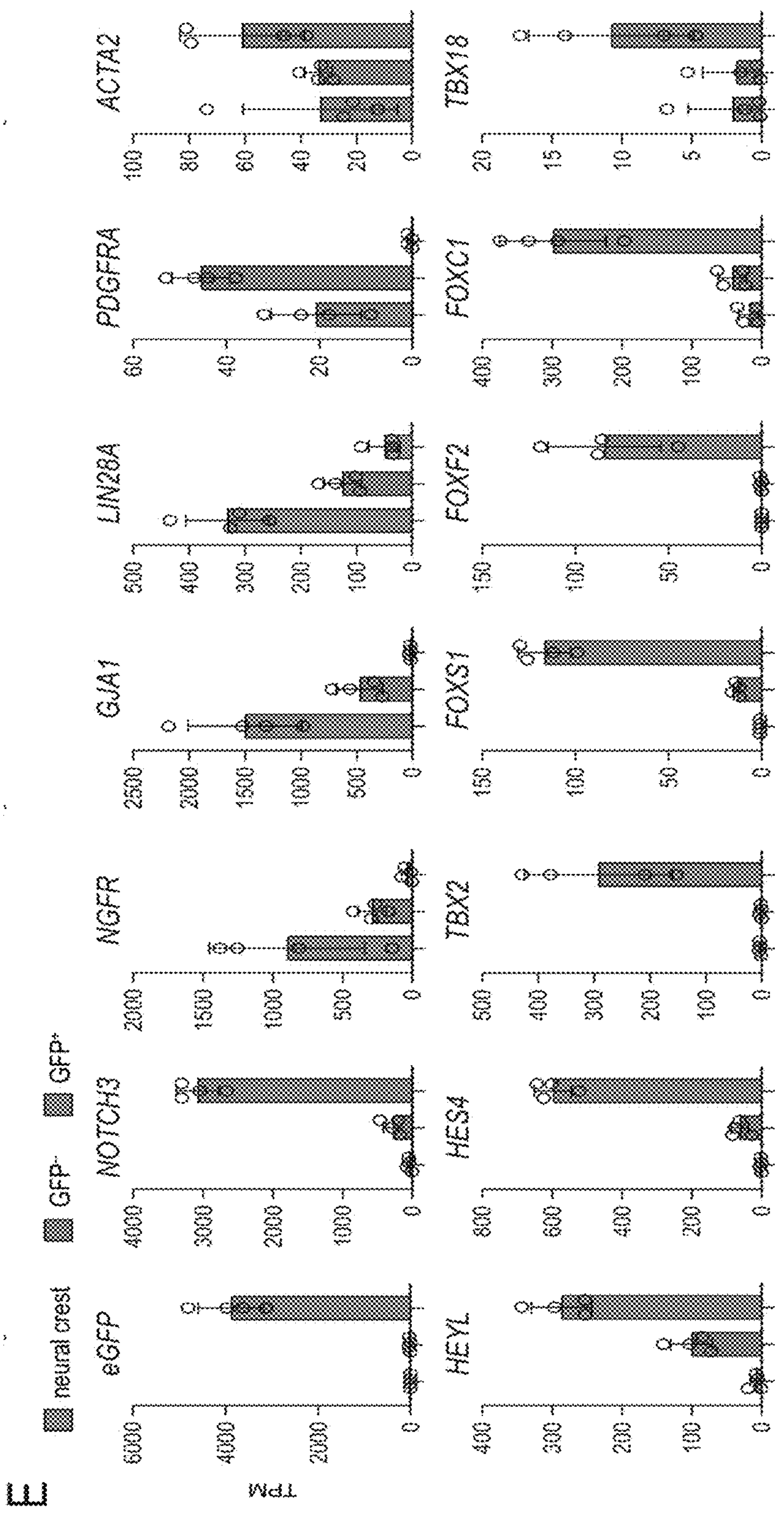
Figure 3:
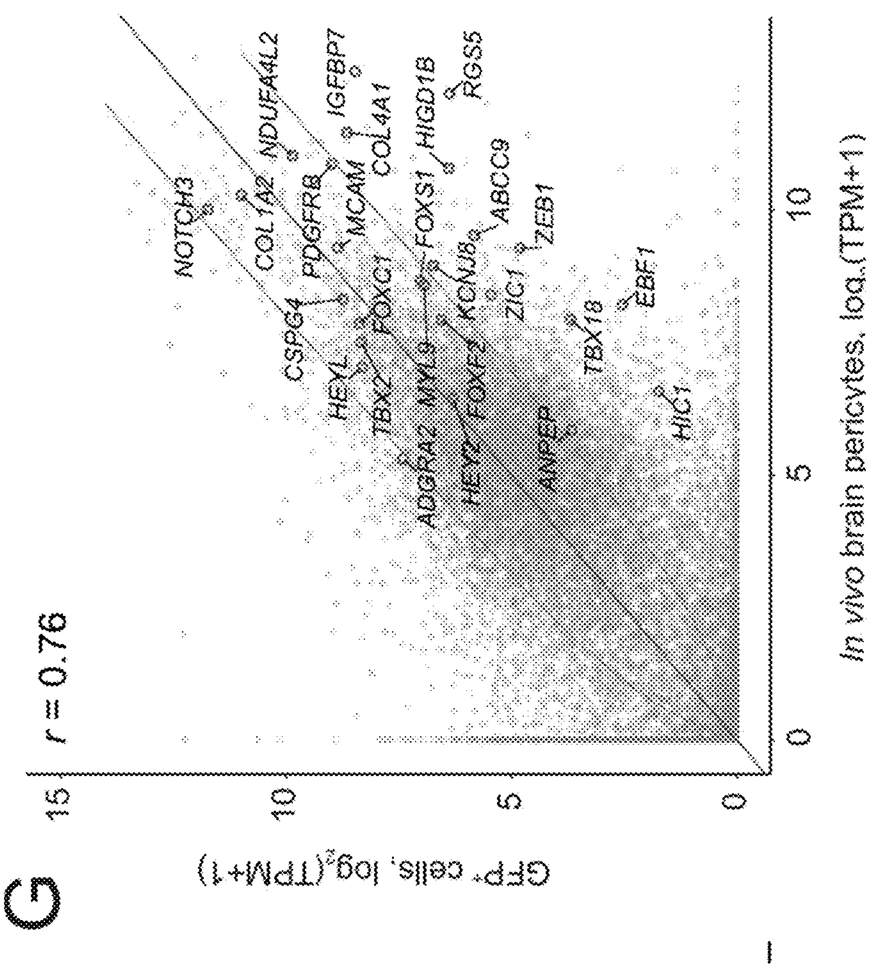
Figure 3:
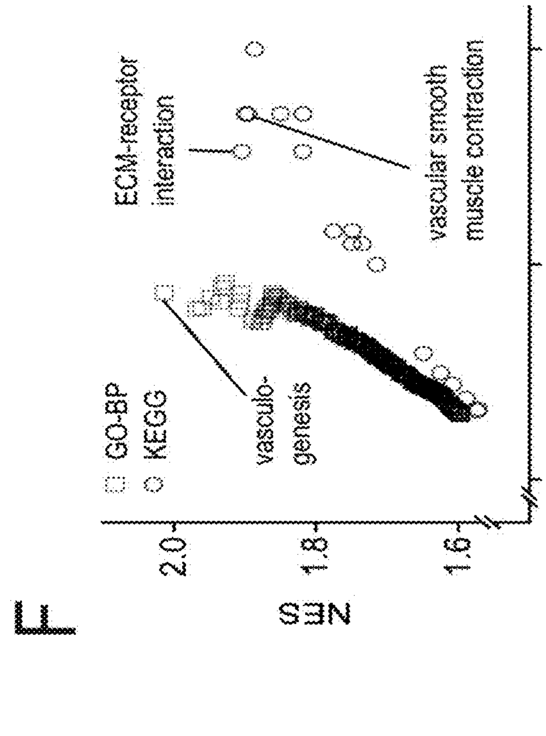
Figure 12:
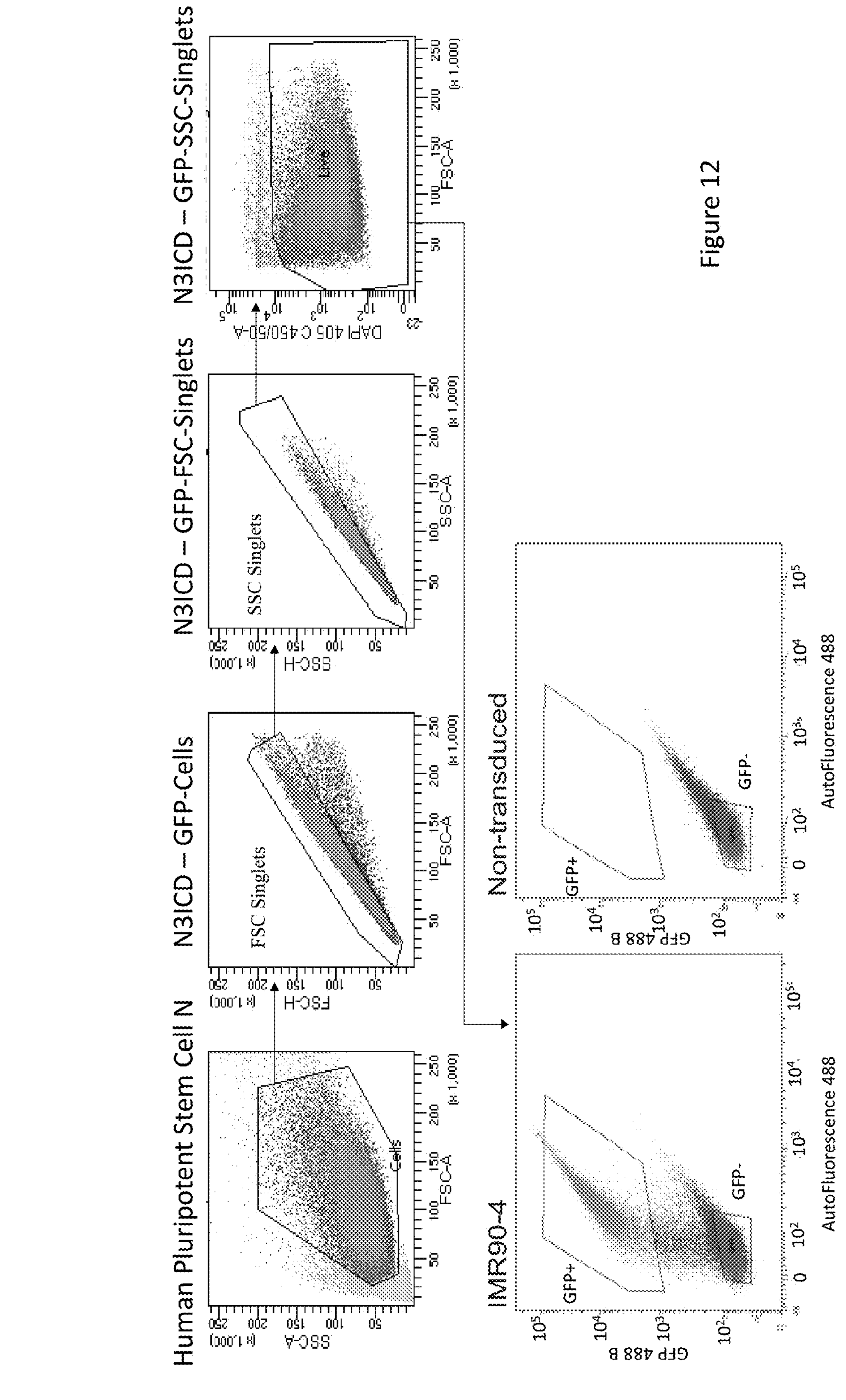
FIG. 12. FACS gating strategy for RNA-seq samples. Examples of initial gating strategies for single cells based on forward and side scatter, followed by gating strategy for live ($DAPI^-$) cells, are shown at top. Gates for $GFP^+$ and $GFP^-$ cells are shown below for each of the four hPSC lines evaluated (IMR90-4, H9, WTC11, and DF19-9-11T). An example of a non-transduced culture from the IMR90-4 hPSC line is also shown.
Figure 12:
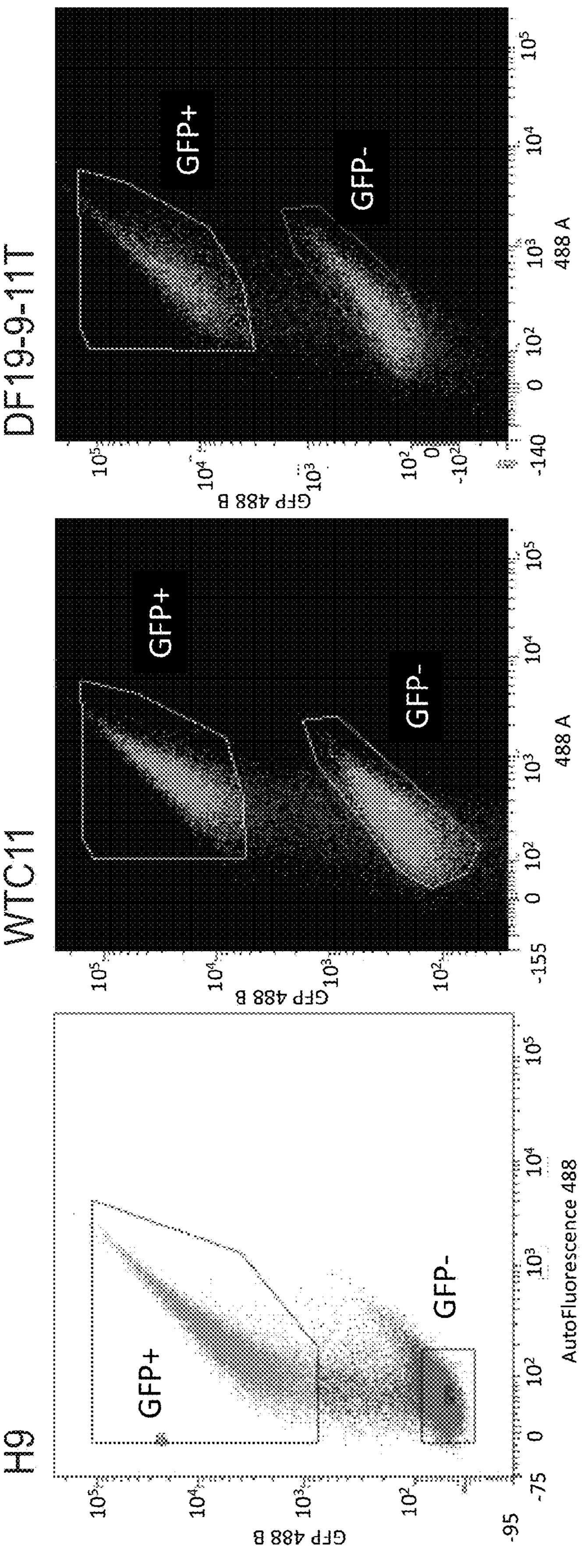
Figure 13:
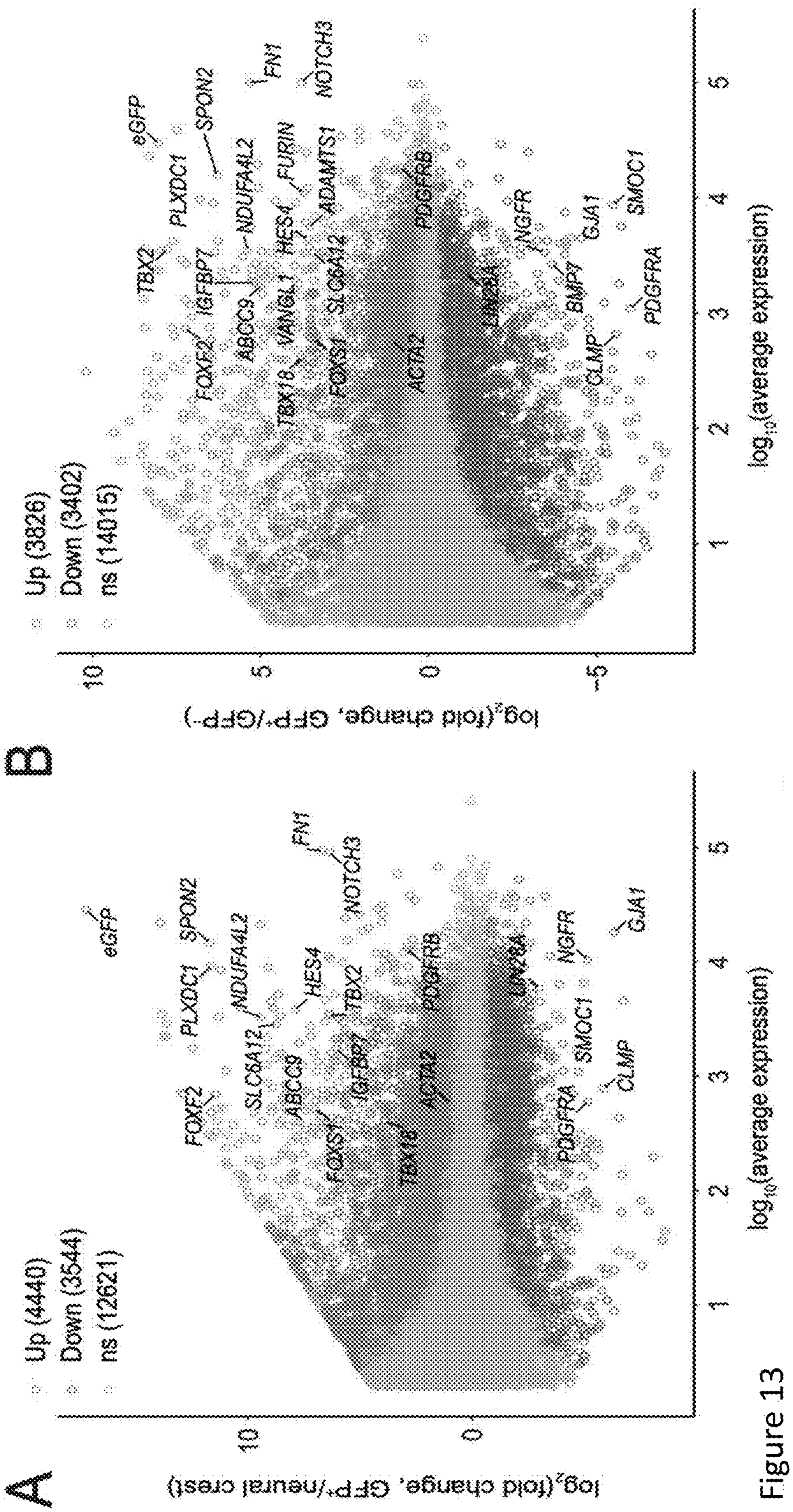
FIG. 13. RNA-seq differential expression analysis and clustering. (A, B) Differential expression analysis of $GFP^+$ cells compared to neural crest (A) and $GFP^+$ cells compared to $GFP^-$ cells (B). Data are displayed in MA plots; volcano plots are shown in FIG. 3C-D. Differentially expressed genes (adjusted P-values <0.05, DESeq2 Wald test with Benjamini-Hochberg correction) are highlighted, and the numbers of upregulated and downregulated genes are shown in the legends. (C) Hierarchical clustering of samples and genes. The red-colored portion of the dendrogram at left indicates a 1110-gene module exhibiting selective expression in $GFP^+$ cells compared to both $GFP^-$ cells and neural crest. Selected genes from this module are displayed at right. (D) Transcript abundance (TPM) of selected mural cell-enriched transcripts.
Figure 13:
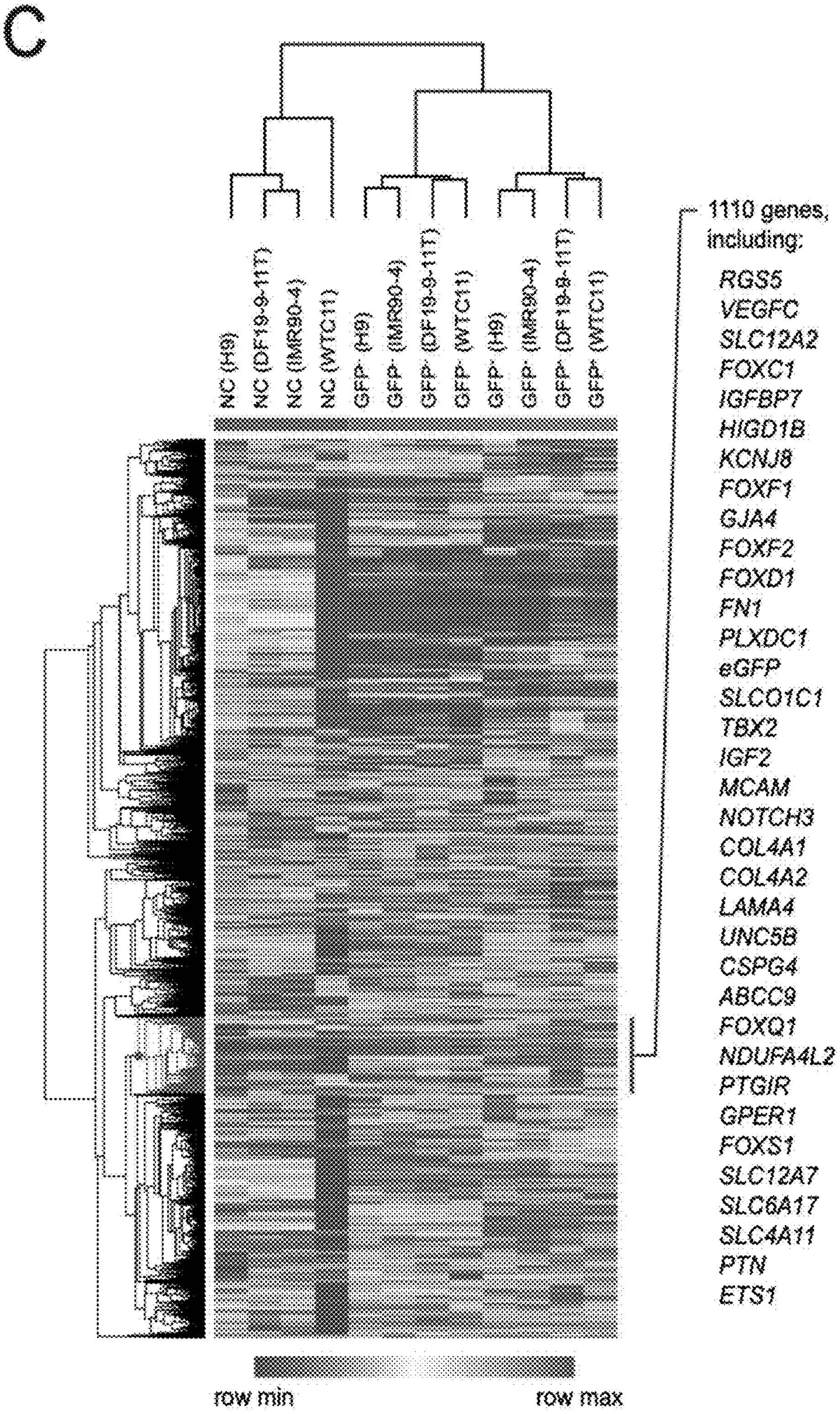
Figure 13:
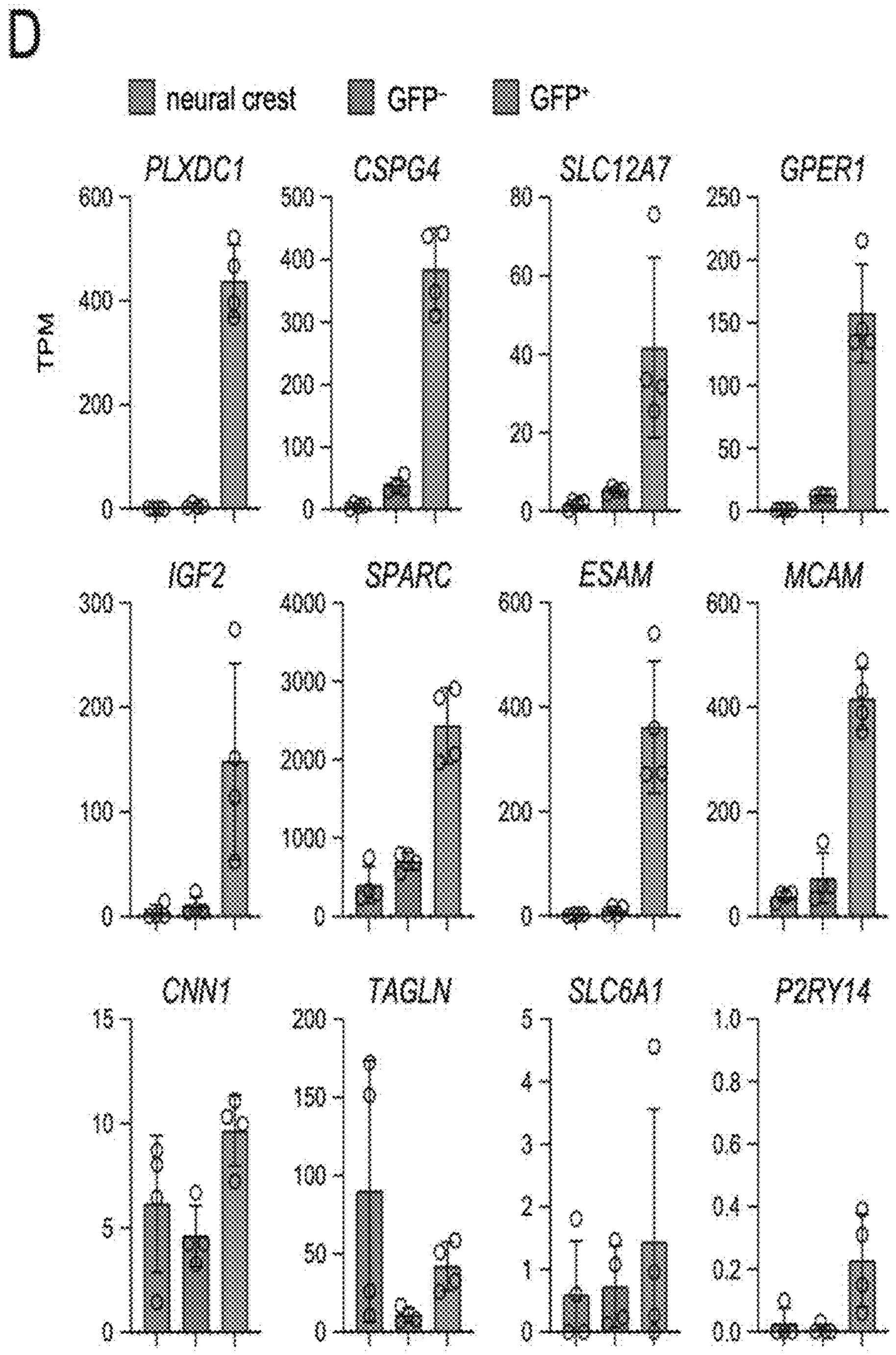

We used RNA-seq to obtain transcriptomic profiles of neural crest cells and FACS-isolated $GFP^-$ and $GFP^+$ cells from N3ICD-GFP-transduced cultures from four hPSC lines (FIG. 12). In principal component analysis, the three cell types segregated along principal component 1, which explained 66% of the variance (FIG. 3A). Visualization of RNA-seq reads confirmed that in addition to transgene-derived NOTCH3 transcripts, endogenous NOTCH3 was also upregulated in $GFP^+$ cells (FIG. 3B). We identified differentially expressed genes in $GFP^+$ cells compared to neural crest (FIG. 3C; FIG. 13A) and in $GFP^+$ cells compared to $GFP^-$ cells (FIG. 3D; FIG. 13B). In both comparisons, $GFP^+$ cells were enriched for mural cell and pericyte marker genes, including the key transcription factors HEYL, HES4, TBX2, FOXS1, FOXF2, and FOXC1, some of which have established functional roles in brain pericyte development and function (47, 48) (FIG. 3C-E; FIG. 13). PDGFRB, RGS5, NDUFA4L2, KCNJ8, ABCC9, HIGD1B, IGFBP7, PLXDC1, CSPG4, and ADAMTS1 were similarly enriched in $GFP^+$ cells (FIG. 3C-E; FIG. 13). Consistent with results of RT-qPCR, ACTA2 was expressed at moderate levels (~40-60 TPM) in all cell types and was not differentially expressed (FIG. 3C-E).

The canonical neural crest marker NGFR was downregulated in $GFP^+$ cells compared to both neural crest and $GFP^-$ cells, as was LIN28A, which plays a role in neural crest multipotency (49). PDGFRA, which is enriched in fibroblasts compared to mural cells in vivo (45, 50), was nearly absent in $GFP^+$ cells, but expressed by $GFP^-$ cells (FIG. 3E). Although $GFP^-$ cells also expressed PDGFRB, they lacked several other mural cell markers and retained some expression of neural crest genes (FIG. 3E), suggesting that interactions with N3ICD-overexpressing $GFP^+$ cells cause partial differentiation of these cells to a non-mural fate. Hierarchical clustering revealed a gene module with highly enriched expression in $GFP^+$ cells compared to both $GFP^-$ cells and neural crest; this module contained known mural/pericyte transcripts, including FOXD1, GJA4, PTGIR, and MCAM (CD146) in addition to many of those mentioned above (FIG. 13C-D), further supporting the mural/pericyte identity of cells derived via Notch3 activation. Genes with known enrichment in brain mural cells compared to those of other organs, including PTN, GPER1, and SLC6A17 (36, 45), were also enriched in GFP$^+$ cells (FIG. 13C-D), supporting the notion that brain-enriched expression is at least partially attributable to the neural crest origin Furthermore, the GABA transporter gene SLC6A12, which we and others recently identified as enriched in human compared to mouse brain pericytes (35, 36, 50), was robustly upregulated in GFP$^+$ cells compared to neural crest and GFP$^-$ cells (FIG. 3C-E). SLC6A1, another human-enriched pericyte gene (36, 50), however, was not expressed (FIG. 13D), highlighting that while Notch signaling activates a mural cell transcriptional program, other factors are likely required for complete acquisition of mural cell phenotype. We also observed minimal expression of VTN in all cells (approximately 1 TPM), consistent with observations that human brain pericytes lack VTN despite robust expression in mouse brain pericytes (35, 36, 51), while other ECM-related genes (FN1, COL4A1, COL4A2, COL1A1, and LAMA4) were indeed upregulated in GFP$^+$ cells (FIG. 3C-E). Together, these results suggest that cells derived from hPSCs via this strategy (i) are mural cells, (ii) have molecular hallmarks that distinguish brain and non-brain mural cells, and (iii) can at least partially capture species-specific differences in mural cell gene expression observed in vivo.

Figure 14:
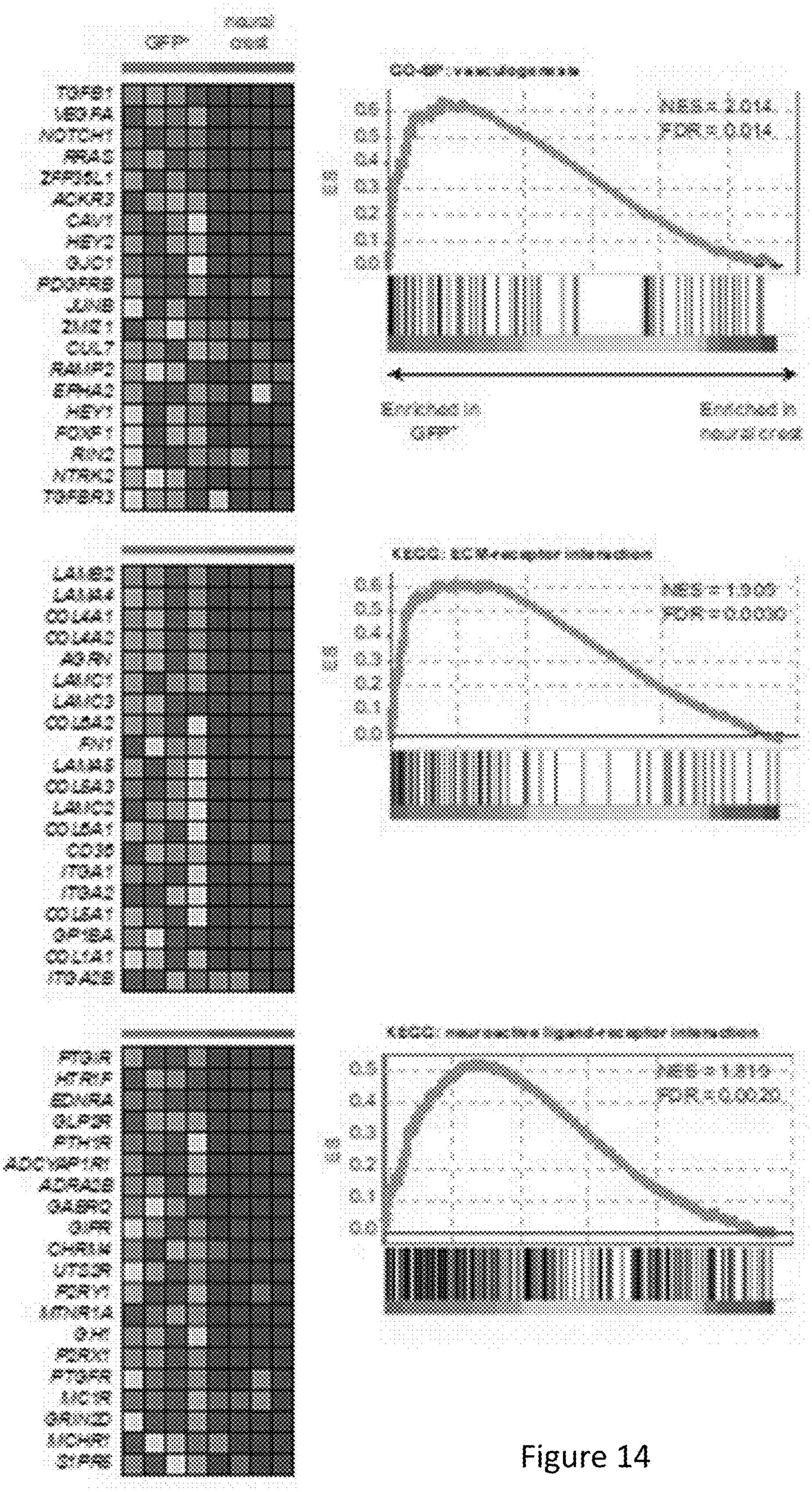
FIG. 14. Gene sets enriched in $GFP^+$ cells compared to neural crest. GSEA enrichment plots for 6 gene sets of interest are shown. For each gene set, plots at left display normalized expression of up to 20 genes listed as core enrichments for each gene set, in order of GSEA rank. NES: normalized enrichment score.
Figure 14:
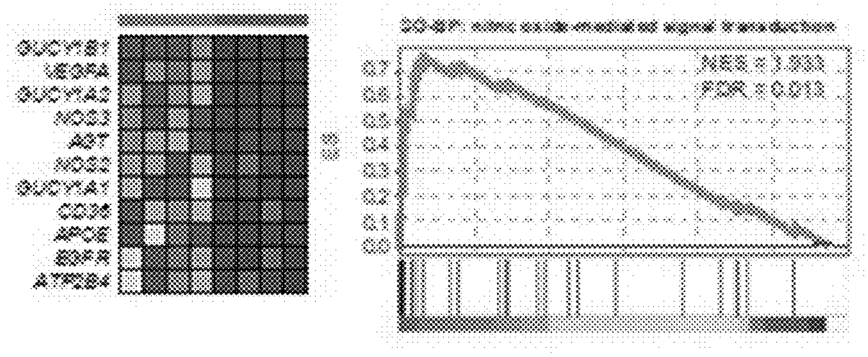
Figure 14:
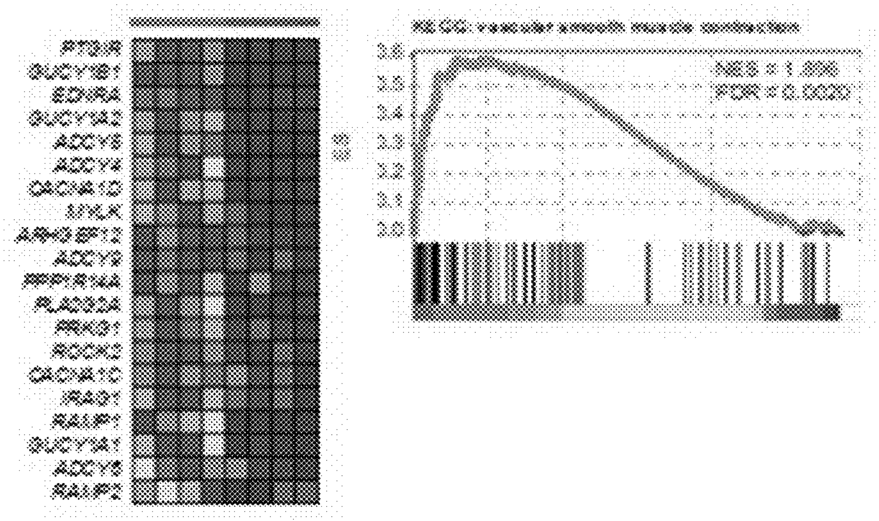
Figure 14:
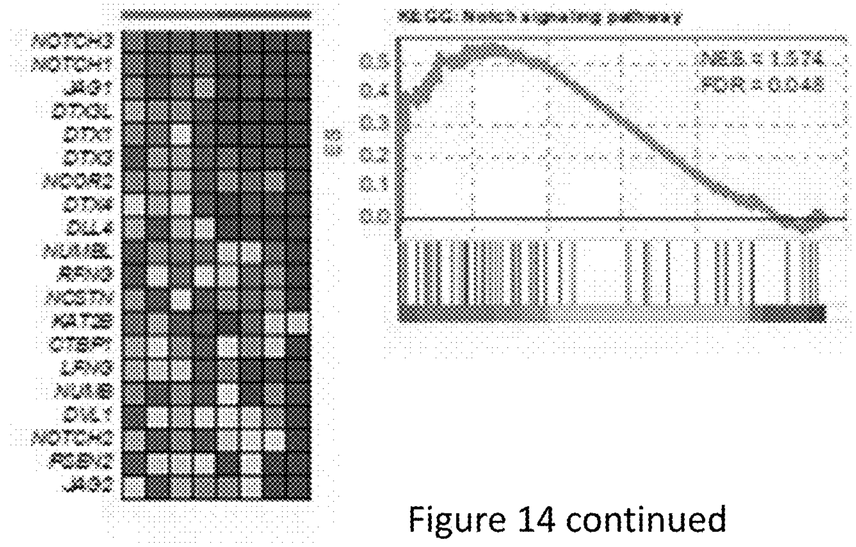

We next identified gene sets enriched in GFP$^+$ cells compared to neural crest, using the KEGG and gene ontology-biological process (GO-BP) databases (FIG. 3F; FIG. 14). As expected, the Notch Signaling Pathway gene sets from both KEGG and GO-BP databases were enriched (FIG. 14). Additional enriched gene sets included GO-BP Vasculogenesis, GO-BP Nitric Oxide-Mediated Signal Transduction, and KEGG Vascular Smooth Muscle Contraction, which was driven by enrichment of genes encoding guanylate and adenylate cyclases (e.g., GUCY1B1, GUCY1A2, ADCY5) and regulators of actomyosin contraction and cytoskeleton (e.g., PPP1R14A, MYLK, ROCK1), consistent with vascular mural cell identity (FIG. 3F; FIG. 14). Consistent with previously noted upregulation of ECM-related genes, the KEGG gene set ECM-Receptor Interaction was enriched (FIG. 3F; FIG. 14). Notably, we observed enrichment of the KEGG gene set Neuroactive Ligand-Receptor Interaction, which we previously reported as depleted in cultured primary brain pericytes compared to in vivo pericytes (36) (FIG. 3F). Highly enriched genes in this set included PTGIR, PTHIR, EDNRA, and GIPR (FIG. 14), but some genes encoding key mural cell receptors such as P2RY14, were not expressed (FIG. 13D), suggesting that other factors would be required to obtain cells with the complete mural cell receptor repertoire. Finally, we directly compared the average transcriptome profile of GFP$^+$ cells to that of in vivo human brain pericytes (FIG. 3G). While the overall correlation was similar to that of existing hPSC-derived brain pericyte-like cells (FIG. 6A), GFP$^+$ cells exhibited a notable improvement in the expression of key mural cell transcription factors and other markers (FIG. 3G).

Functional Attributes of Resulting Mural Cells

Figure 4:
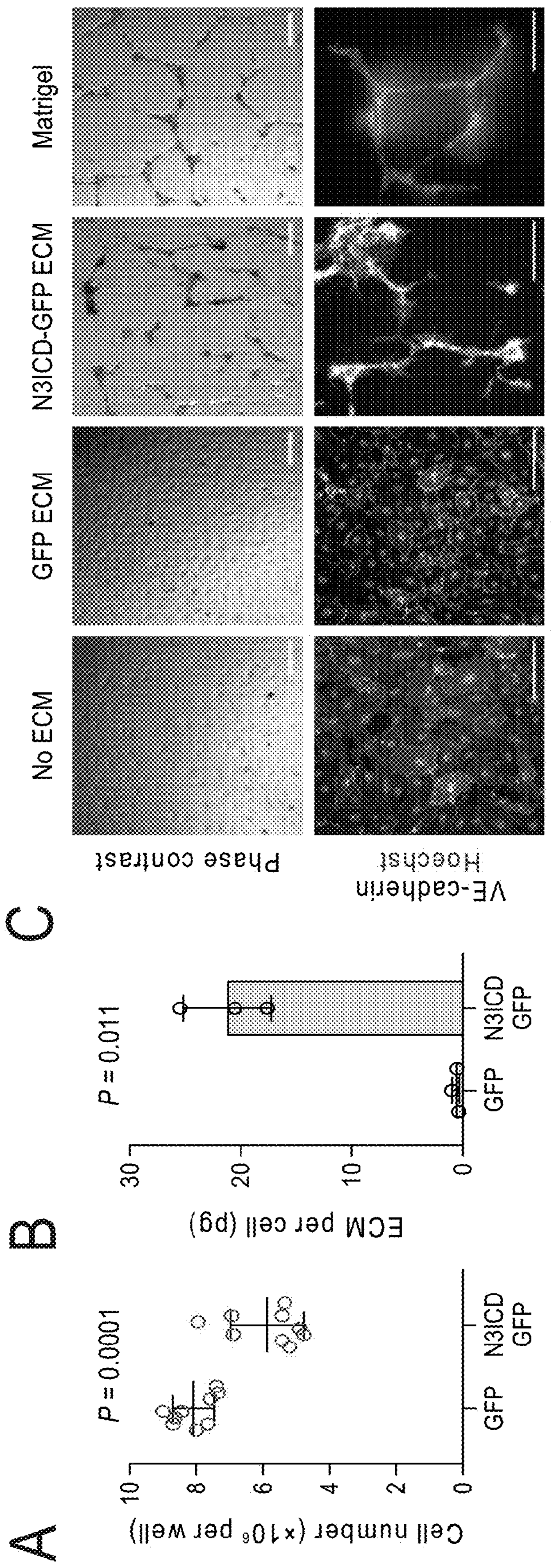
FIG. 4. Functional properties of mural cells. (A) Number of resulting cells 6 days after transduction of neural crest with GFP or N3ICD-GFP lentiviruses. Points represent replicate wells from three differentiations of the H9 hPSC line, each differentiation indicated with a different color. Bars indicate mean values±SD. P-value: two-way ANOVA. (B) Total extracellular matrix production 6 days after transduction of neural crest with GFP or N3ICD-GFP lentiviruses. Each point represents the average ECM quantity from three wells of a differentiation of the H9 hPSC line, normalized to average cell number from three parallel wells within the differentiation. P-value: paired Student's t test. (C) HUVEC cord formation assay on decellularized ECM from GFP- or N3ICD-GFP-transduced cultures, and from no ECM and Matrigel controls. Phase contrast and VE-cadherin immunocytochemistry images are shown. Hoechst nuclear counterstain overlaid in immunocytochemistry images. Scale bars: 200 μm. (D) Quantification of HUVEC cord formation for the conditions described in (C). Blinded images were scored from 0 (no cords) to 3 (virtually all cells associated with cords); see Methods. Data from the GFP ECM and N3ICD-GFP ECM conditions are derived from three independent differentiations, two in the H9 hPSC line and one in the IMR90-4 hPSC line; data from no ECM and Matrigel controls are derived from two independent experiments. P-values: Kruskal-Wallis test followed by Steel-Dwass test. (E) Coculture cord formation assay with HUVECs, HUVECs and neural crest cells (+NC), HUVECs and $GFP^-$ cells from a N3ICD-GFP-transduced culture (5 days post-FACS; $+GFP^-$), and HUVECs and $GFP^+$ cells from a N3ICD-GFP-transduced culture ($+GFP^+$). Images (overlays of phase contrast and GFP fluorescence) are shown from 24 h and 72 h after initiating assay. Scale bars: 200 μm. (F) Calcium response of cells in a N3ICD-GFP-transduced culture to KCl application. 40 mM KCl was added at t=50 s. (G) Phase contrast images of $GFP^+$ cells from a N3ICD-GFP-transduced culture (2 days post-FACS) at t=0 min and t=15 min after treatment with 40 mM KCl. Scale bars: 50 μm. (H) Change in area of $GFP^+$ cells (2 days post-FACS) 15 min after treatment with water (vehicle) or 40 mM KCl. Points represent replicate wells from three differentiations of the H9 hPSC line, each differentiation indicated with a different color. Bars indicate mean values±SD. P-value: two-way ANOVA. (I) Intracellular calcium 30 s after addition of 40 mM KCl to GFP-transduced or N3ICD-GFP-transduced cultures pretreated with pinacidil or DMSO (vehicle). Points represent replicate wells from three differentiations of the H9 hPSC line, each differentiation indicated with a different color. Bars indicate mean values±SD. P-values: Tukey's HSD test following ANOVA, P=0.0011 for interaction (DMSO v. pinacidil)×(GFP v. N3ICD-GFP).
Figure 4:
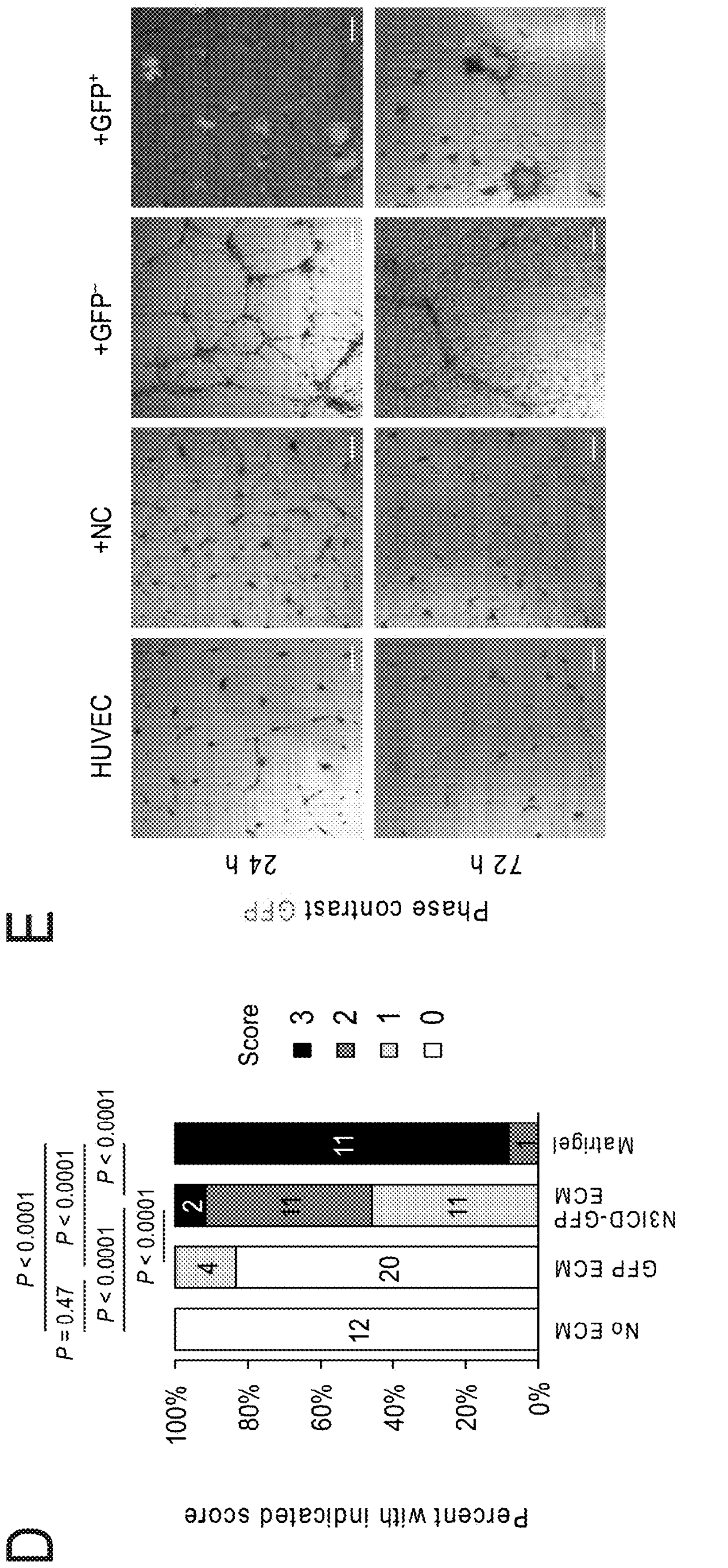
Figure 4:
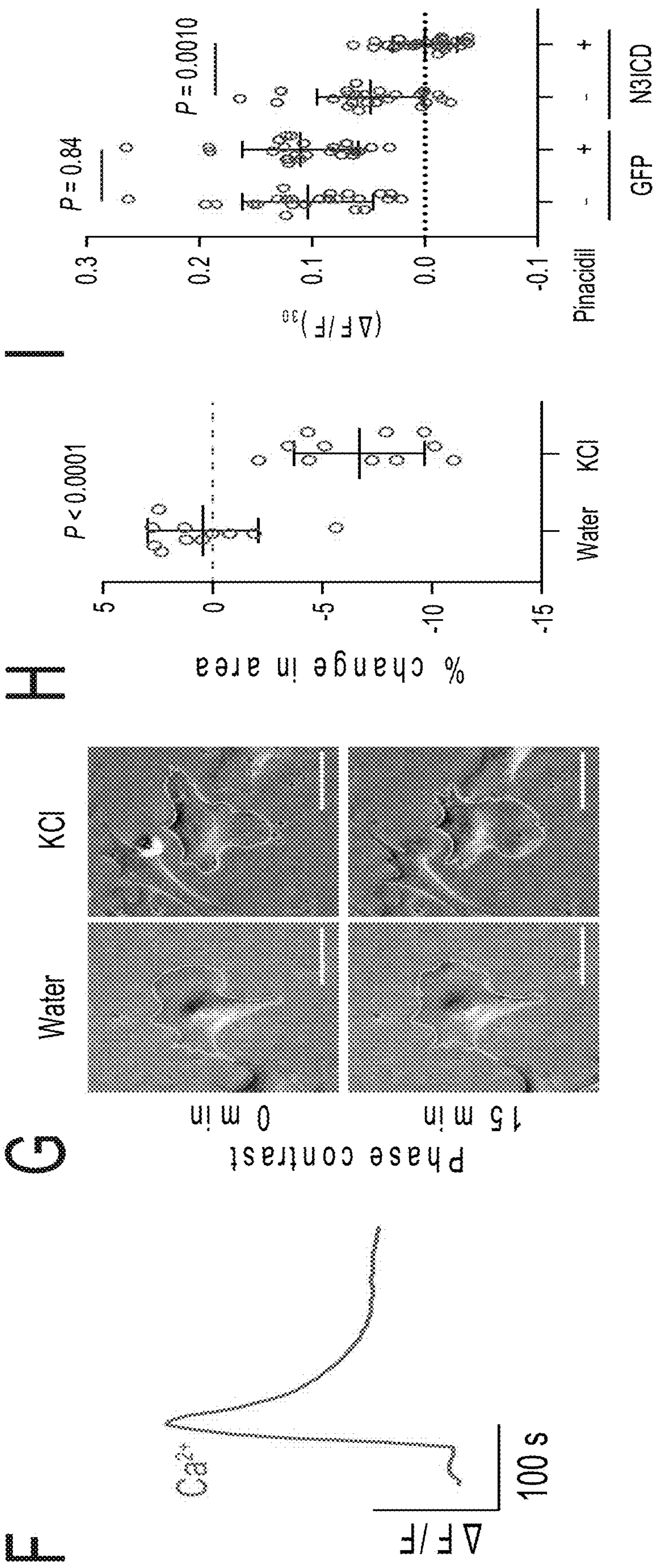
Figure 15:
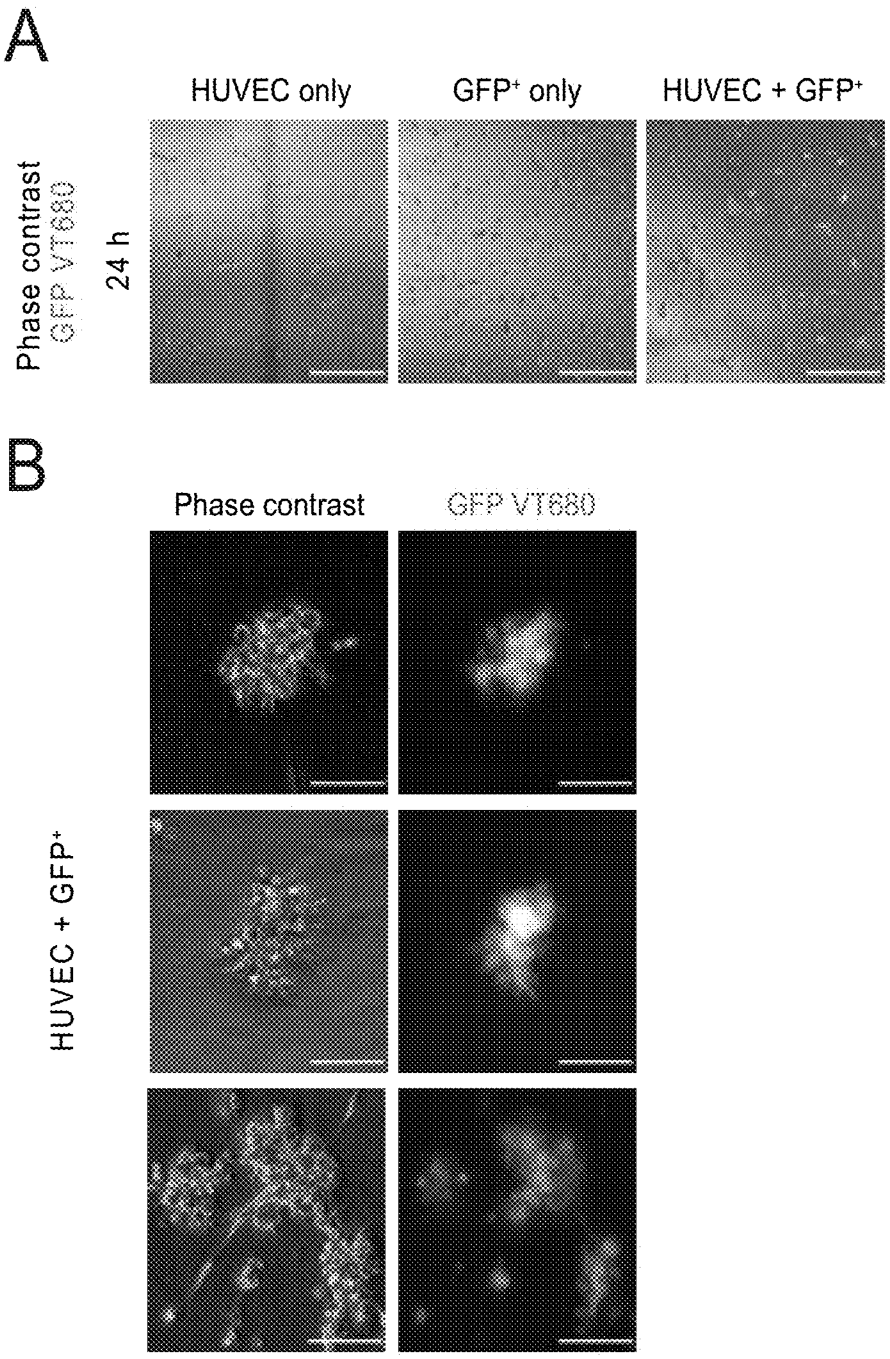
FIG. 15. Mural cell-HUVEC aggregates. (A) Coculture cord formation assay with HUVECs only, $GFP^+$ cells from a N3ICD-GFP-transduced culture only, and HUVECs and $GFP^+$ cells from a N3ICD-GFP-transduced culture (HUVEC+$GFP^+$). HUVECs were prelabeled with VivoTrack680 dye (VT680). Images (overlays of phase contrast, GFP fluorescence, and VT680 fluorescence) are shown from 24 h after initiating assay. Scale bars: 500 (B) High-magnification images of aggregates from the HUVEC+$GFP^+$ condition as described above. Scale bars: 100 μm.

Production of vascular basement membrane is a key function of mural cells. We visually observed an apparent enrichment in the amount of ECM produced by cultures transduced with N3ICD-GFP compared to GFP, which we confirmed by decellularization followed by quantification of remaining total protein (see Methods). Compared to GFP-transduced cultures, N3ICD-overexpressing cultures generated approximately 20 times more extracellular matrix per cell despite a slight reduction in total cell number (FIG. 4A-B), consistent with the marked upregulation of ECM-encoding genes in RNA-seq data and protein-level enrichment of fibronectin. We next evaluated the ability of these decellularized matrices to support formation of endothelial cords, a widely used in vitro proxy for angiogenic potential (38, 41, 52, 53). While human umbilical vein endothelial cells (HUVECs) cultured on ECM from GFP-transduced cultures adopted the same cobblestone morphology as HUVECs cultured on no ECM, HUVECs cultured on ECM from N3ICD-GFP-transduced cultures formed cords, albeit more variably than on the positive control Matrigel substrate (FIG. 4C-D). We also directly cocultured neural crest cells, and GFP$^+$ and GFP$^-$ cells 5 days after FACS with HUVECs on the Matrigel substrate. 24 h after cell seeding, cords formed from HUVECs alone and those formed in neural crest cocultures were similar, while cords in GFP$^-$ cell cocultures were longer, consistent with the ability of many mesenchymal cell types to associate with endothelial cords and modulate cord formation (53, 54). In GFP$^+$ cell cocultures, however, we observed highly reproducible formation of mural-endothelial aggregates, a phenomenon previously observed in primary pericyte cocultures at later timepoints (41) and in cocultures with immature smooth muscle cells derived from hPSCs (53) (FIG. 4E). Importantly, aggregates contained both GFP+ cells and HUVECs, and GFP+ cells did not form such large aggregates in the absence of HUVECs (FIG. 15). Thus, while GFP$^+$ cells undergo molecular changes after FACS and replating (FIG. 11), these results support a persistent, striking difference in functional phenotype between GFP$^+$ and GFP$^-$ cells.

Mural cells regulate vascular tone, and while the relative contributions of different mural cell subtypes to neurovascular coupling remain the subject of debate, virtually all mural cells appear capable of contraction, at least under artificial stimuli (55). Potassium (at concentrations causing depolarization) is widely used to assess contractility of pericytes and smooth muscle cells in vitro and in vivo (40, 56). We first used calcium imaging of a N3ICD-GFP-transduced culture to confirm that application of 40 mM KCl led to depolarization and calcium influx (FIG. 4F). Because the cell density at this time point precludes assessment of cell size, we asked whether KCl application would cause contraction of GFP$^+$ cells isolated via FACS and replated at low cell density (FIG. 4G). Two days after FACS, cells underwent an average reduction in area of approximately 7% 15 min after KCl addition, compared to an average 0% change after addition of water, with cells in both conditions extending and withdrawing cellular processes (FIG. 4G,H). These results support the contractile ability of mural cells derived from neural crest via N3ICD overexpression. Our RNA-seq data demonstrated upregulation of KCNJ8 and ABCC9 in GFP$^+$ mural cells (FIG. 3E). These genes encode subunits of the ATP-sensitive potassium channel (K-Alp), which has been implicated in mural cell propagation of hyperpolarizing signals during neurovascular coupling (57). We therefore used the $K_{ATP}$ channel inhibitor pinacidil to assess the functionality of this channel in our cells. N3ICD-GFP-transduced cultures pretreated with pinacidil exhibited reduced intracellular calcium after KCl-induced depolarization compared to control (DMSO)-treated cells; such a difference was not observed in GFP-transduced cultures (FIG. 41). These results suggest that $K_{ATP}$ channels are functional in mural cells derived via N3ICD overexpression.

Figure 5:
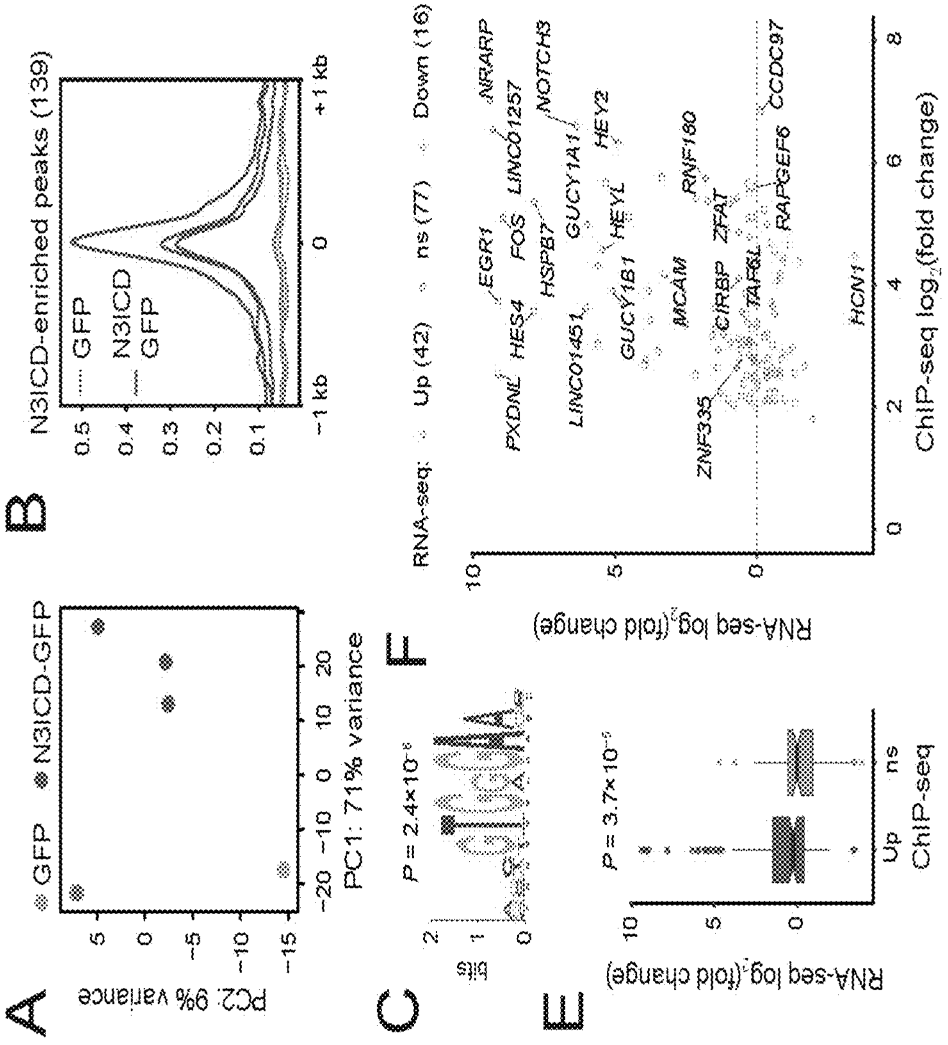
FIG. 5. Notch3 ChIP-seq of N3ICD-GFP- and GFP-transduced cells. (A) Principal component analysis based on all peaks. Points are colored by cell type: GFP-transduced cells (gray), N3ICD-GFP-transduced cells (green). Data are from three independent differentiations of the H9 hPSC line. (B) Profile plots for the 139 N3ICD-enriched peaks. Lines represent the average peak profile from each sample. (C) Motif logo for the overrepresented motif in N3ICD-enriched peaks. P-value as reported by MEME-ChIP (101). (D) Representative genome browser plots for genes of interest. From top, tracks are: Notch3 ChIP-seq signal from GFP-transduced cells, Notch ChIP-seq signal from N3ICD-GFP-transduced cells, N3ICD-enriched peaks as identified by DiffBind, ATAC-seq signal from a human cortex endothelial/mural cell cluster (61), endothelial/mural ATAC-seq peaks as identified by MACS (61), ENCODE cCREs (red: promoter-like signature, orange: proximal enhancer-like signature, yellow: distal enhancer-like signature) (62), and putative RBPJ binding sites from the JASPAR database (63). Additional genome browser plots are shown in FIG. 16. (E) RNA-seq log 2 (fold change) data from comparison of $GFP^+$ (mural) and neural crest cells for genes associated with N3ICD-enriched Notch3 ChIP-seq peaks (Up, n=134) and genes associated with non-enriched peaks (ns, n=75). P-value: Student's t test. (F) Comparison of RNA-seq log 2 (fold change) data ($GFP^+$ (mural) versus neural crest cells) and ChIP-seq log 2 (fold change) data (N3ICD-GFP-transduced versus GFP-transduced cells) for genes associated with N3ICD-enriched Notch3 ChIP-seq peaks. Points are colored by differential expression in RNA-seq data and the numbers of upregulated, downregulated, and non-significant genes are shown in the legend.
Figure 5:
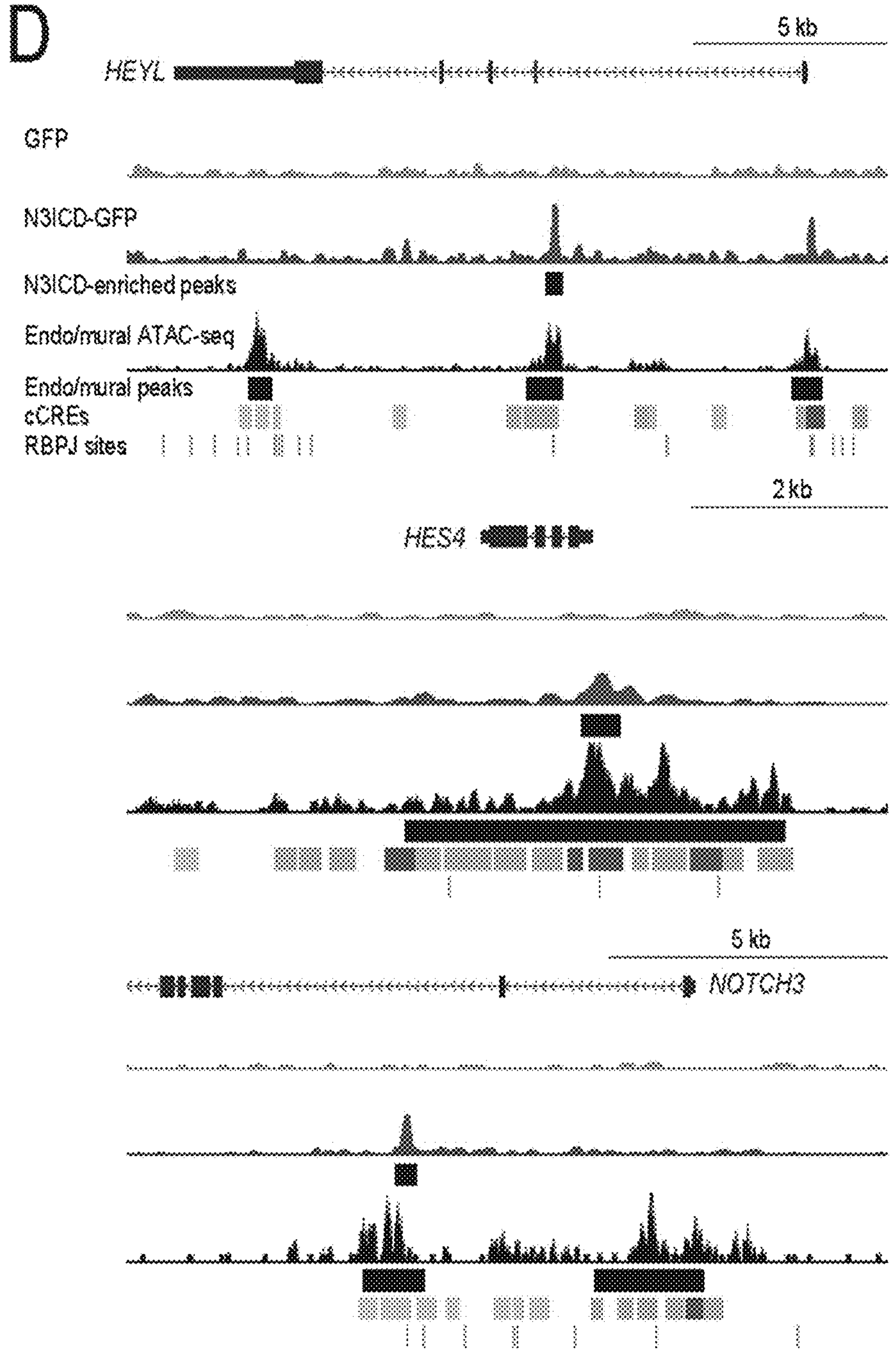
Figure 16:
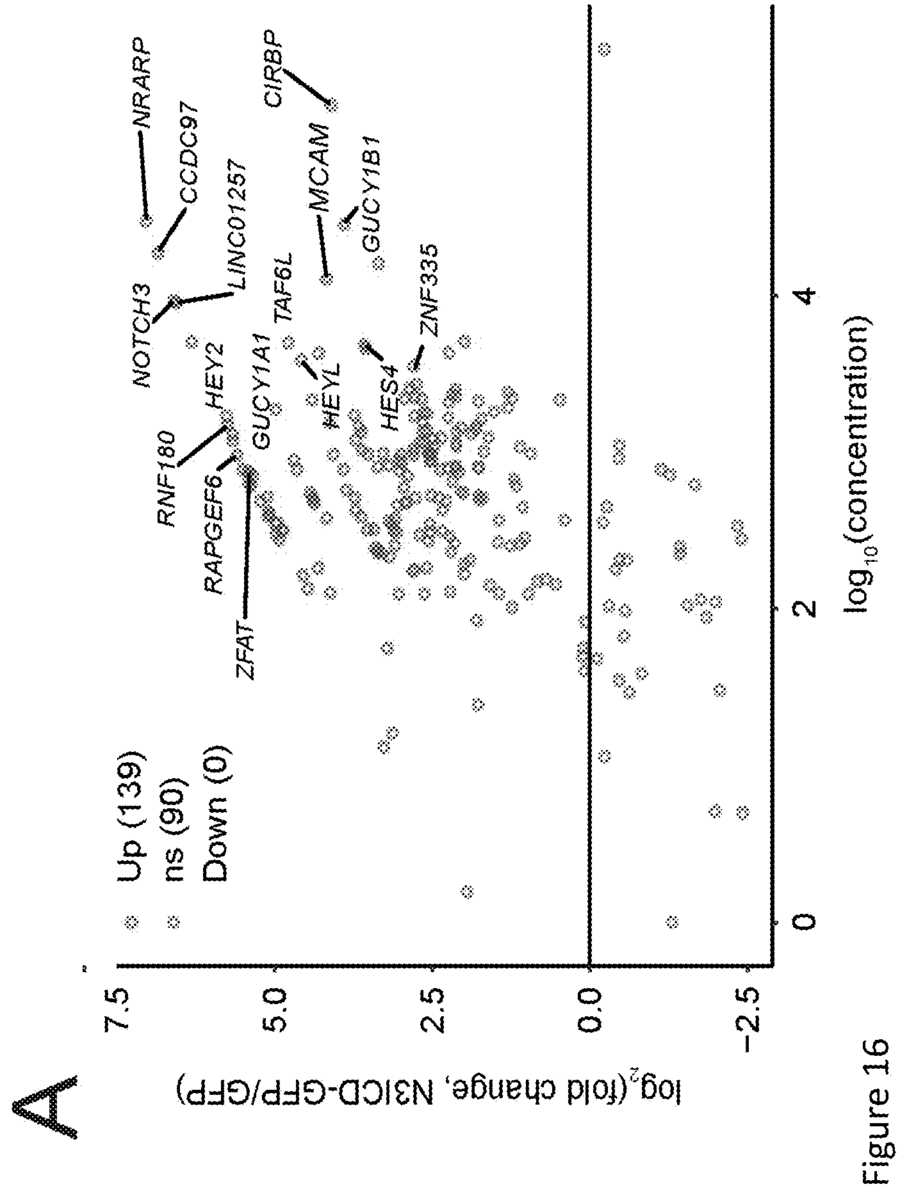
FIG. 16. N3ICD-enriched peaks from Notch3 ChIP-seq. (A) Peak enrichment analysis of N3ICD-GFP-transduced cells compared to GFP-transduced cells. Data are displayed in a MA plot. N3ICD-enriched peaks (adjusted P-values <0.05, DiffBind/DESeq2 Wald test with Benjamini-Hochberg correction) are highlighted in green, and the numbers of enriched (Up) and non-significant (ns) peaks are shown in the legend. Selected points are annotated with putative target gene names. (B) Genome browser plots for genes of interest. From top, tracks are: Notch3 ChIP-seq signal from GFP-transduced cells (data from three differentiations), Notch ChIP-seq signal from N3ICD-GFP-transduced cells (data from three differentiations), N3ICD-enriched peaks as identified by DiffBind, ATAC-seq signal from a human cortex endothelial/mural cell cluster (61), endothelial/mural ATAC-seq peaks as identified by MACS (61), ENCODE cCREs (red: promoter-like signature, orange: proximal enhancer-like signature, yellow: distal enhancer-like signature) (62), and putative RBPJ binding sites from the JASPAR database (63).
Figure 16:
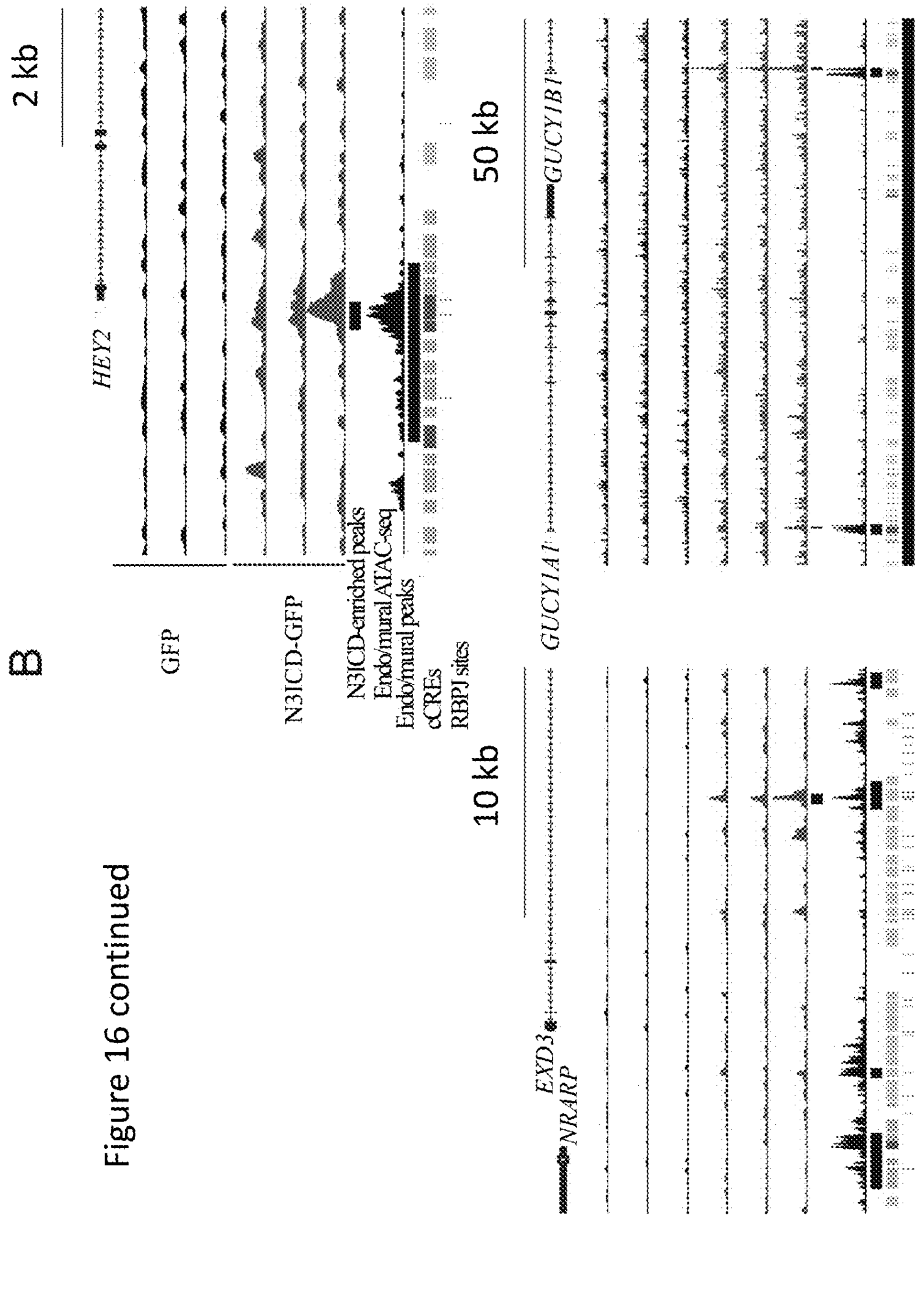

Cis-Regulatory Elements Underlying Notch3 Function in Mural Cell Differentiation In the canonical model of Notch signaling, Notch intracellular domains (NICDs) activate transcription of a small number of transcription factors (i.e., HES and HEY family members); however, the genome contains tens of thousands of putative RBPJ binding sites, and NICDs regulate a diverse array of genes in a cell type/tissue-specific context (58). Thus, as a first step toward defining the gene regulatory network underlying neural crest-to-mural cell differentiation, we used Notch3 ChIP-seq to identify cis-regulatory elements (CREs) directly bound by N3ICD in N3ICD-GFP-transduced cultures. In principal component analysis based on all Notch3 peaks (called by comparison of Notch3 IP and matched input controls), N3ICD-GFP-transduced cells clustered distinctly from control GFP-transduced cells along principal component 1, which explained 71% of the variance (FIG. 5A). Peak enrichment analysis using the DiffBind package (59) revealed 139 peaks enriched in N3ICD-GFP-transduced cells ("N3ICD-enriched peaks"), 90 non-enriched peaks, and no Notch3 peaks enriched in GFP-transduced cells (FIG. 5B; FIG. 16A), consistent with the lack of Notch3-RBPJ coimmunoprecipitation in GFP-transduced cells (FIG. 8B). Importantly, the RBPJ consensus motif GTGGGAA (60) was overrepresented in N3ICD-enriched peaks (FIG. 5C), and N3ICD-enriched peaks were located proximal to canonical transcriptional targets of Notch3 signaling, including HEYL, HES4, HEY2, and NRARP (FIG. 5D; FIG. 16A, B). We also identified a putative enhancer peak within the first intron of the NOTCH3 gene (FIG. 5D), consistent with the positive feedback observed on the transcript and protein levels. Additional N3ICD-enriched peaks were proximal to genes including MCAM, GUCY1A1, GUCYIB1, CIRBP, ZNF335, RNF180, and TAF6L, in addition to a small number of distal intergenic peaks (FIG. 16A, B). N3ICD-enriched peaks aligned with single cell ATAC-seq peaks from a human cortex mural cell/endothelial cell cluster (61), putative promoter and enhancer signatures from the ENCODE candidate CRE database (62), and putative RBPJ binding sites from the JASPAR database (63) (FIG. 5D; FIG. 16B).

In RNA-seq differential expression analysis of $GFP^+$ mural cells and neural crest, the average fold change of genes associated with N3ICD-enriched peaks exceeded that of non-enriched peaks (FIG. 5E). Many genes associated with N3ICD-enriched peaks were upregulated in RNA-seq data, including HEYL, HES4, HEY2, NRARP, NOTCH3, GUCY1A1, GUCYIB1, EGR1, and FOS (FIG. 5F). Other peak-associated genes, including the transcriptional regulators ZNF335 and TAF6L, were not differentially expressed and thus likely do not regulate downstream differentiation processes (FIG. 5F). Notably, non-HES/HEY family mesenchymal and mural cell transcription factors such as FOXF2, FOXC1, FOXS1, TBX18, and TBX2, which were upregulated on the transcript level, were not associated with Notch3 ChIP-seq peaks, suggesting transcriptional regulation downstream of HEYL, HES4, HEY2, and potentially other upstream factors. In summary, these data suggest that Notch3 regulates mural cell differentiation by serving as an input to a relatively small number of transcriptional targets.

Methods hPSC Maintenance

Matrigel-coated plates were prepared by resuspending a frozen 2.5 mg aliquot of Matrigel, Growth Factor Reduced (Corning, Glendale, Ariz.) in 1 mL of DMEM/F12 (Life Technologies, Carlsbad, Calif.) and diluting the resulting solution in 29 mL of DMEM/F12. 1 mL of this solution was used to coat each well of five 6-well plates. Plates were stored at 37° C. for at least 1 h prior to use, and up to 1 week. The following hPSC lines were used: H9 hESCs (77) (WiCell, Madison, Wis.); IMR90-4 iPSCs (78) (WiCell); DF19-9-11 iPSCs (79) (WiCell); WTC11 iPSCs (80) (Gladstone Institutes, San Francisco, CA). hPSCs were maintained at 37° C., 5% $CO_2$ on Matrigel-coated plates in E8 medium (STEMCELL Technologies, Vancouver, Canada) with daily medium changes. When hPSCs colonies began to touch, cells were dissociated as colonies using ~7 min of Versene (Life Technologies) treatment and transferred to a new Matrigel-coated plate at a split ratio of 1:12.

Neural Crest Differentiation

Neural crest was differentiated according to a previously established protocol (38, 39). When hPSC colonies began to touch, 3-4 wells of cells were dissociated using ~7 min of Accutase (Innovative Cell Technologies, San Diego, CA) treatment, 1 mL per well. The Accutase/single cell suspension was transferred to 4× volume of DMEM/F12 medium and cells were counted using a hemocytometer. Cells were centrifuged for 5 min at 200×g. The cell pellet was resuspended in 1 mL of E8 medium and a volume of the resulting suspension containing $2.84\times10^6$ cells transferred to a tube containing 6.5 mL E8 medium supplemented with 10 μM ROCK inhibitor Y-27632 (Tocris, Bristol, United Kingdom). The resulting cell suspension was distributed to 3 wells of a Matrigel-coated 6-well plate, 2 mL per well. Cells were incubated at 37° C., 5% $CO_2$. The following day, differentiation was initiated by changing medium to E6-CSFD medium. E6-CSFD medium is E6 medium prepared according to ref. (81) supplemented with 1 μM CHIR 99021 (Tocris), 10 μM SB431542 (Tocris), 10 ng/mL FGF2 (Waisman Biomanufacturing, Madison, WI), 1 μM dorsomorphin dihydrochloride (Tocris), and 22.5 μg/mL heparin sodium salt from porcine intestinal mucosa (Sigma-Aldrich, St. Louis, MO). E6-CSFD medium was replaced daily for 15 days. Cells were passaged when confluent: one well of cells was dissociated with 1 mL of Accutase for ~5 min. The Accutase/single cell suspension was transferred to 4× volume of DMEM/F12 medium and centrifuged for 5 min at 200×g. The cell pellet was resuspended in 600 μL of E6-CSFD medium and 100 μL of the resulting suspension transferred to each of 3-6 wells of a 6-well plate each containing 2 mL E6-CSFD medium (for a split ratio of 1:6).

Magnetic-Activated Cell Sorting of Neural Crest

On day 15, 3-6 wells of neural crest cells were dissociated using ~5 min of Accutase treatment, 1 mL per well. The Accutase/single cell suspension was transferred to 4× volume of DMEM/F12 medium and cells were counted using a hemocytometer. Cells were centrifuged for 5 min at 180×g, 4° C. MACS buffer was prepared by supplementing Dulbecco's phosphate-buffered saline, no calcium, no magnesium (Life Technologies) with 0.5% bovine serum albumin (Sigma-Aldrich) and 2 mM ethylenediaminetetraacetic acid (Sigma-Aldrich). The cell pellet was resuspended in 60 μL MACS buffer per $10^7$ cells. FcR Blocking Reagent, human (Miltenyi Biotec, Auburn, CA) and Neural Crest Stem Cell Microbeads, human (Miltenyi Biotec) were added to the cell suspension at 20 μL each per $10^7$ cells. Cells were incubated for 15 min at 4° C. Cells were sorted through an LS Column in a MidiMACS Separator (Miltenyi Biotec) according to manufacturer protocols. Briefly, the column was primed with 3 mL MACS buffer, cells were loaded onto the column, the column was washed 3 times with 3 mL MACS buffer, the column was removed from the MidiMACS Separator, and the cells were eluted with 5 mL MACS buffer. The eluate was centrifuged for 5 min at 180×g, 4° C. and sorted through another LS Column. Cells in the eluate were counted using a hemocytometer. The eluate was centrifuged for 5 min at 180×g, 4° C. The resulting cell pellet was resuspended in a volume of E6-CSFD medium required to achieve a concentration of $10^5$ cells/mL. The resulting cell suspension was distributed to Matrigel-coated 6-well plates, 2 mL per well.

For some experiments, Matrigel-coated 12-well plates (1 mL cell suspension per well), 24-well plates (500 μL cell suspension per well), or 48-well plates (250 μL cell suspension per well) were used. Cells were incubated at 37° C., 5% $CO_2$.

Flow Cytometry

On D15 of the neural crest differentiation, two aliquots of $10^6$ cells were transferred to conical tubes prior to MACS and kept on ice until MACS was complete. $10^6$ cells from the final MACS eluate were also transferred to a conical tube. These three cell suspensions were centrifuged for 5 min at 180×g, 4° C. One pre-MACS cell pellet and the post-MACS cell pellet were each resuspended in 100 μL DPBS containing 0.2 μL p75 antibody and 0.2 μL HNK-1 antibody (Table 1). The other pre-MACS cell pellet was resuspended in 100 μL DPBS containing the mouse IgG1 isotype control antibody and the mouse IgM isotype control antibody (Table 1) at concentrations matched to the corresponding p75 and HNK-1 antibodies. Samples were incubated for 30 min on ice, washed by adding 2 mL DPBS, and centrifuged for 5 min at 180×g, 4° C. Each cell pellet was resuspended in 100 μL DPBS containing 1:500 goat anti-mouse IgG1 Alexa Fluor 647 antibody and 1:500 goat anti-mouse IgM Alexa Fluor 488 antibody. Samples were incubated for 30 min on ice protected from light, washed by adding 2 mL DPBS, and centrifuged for 5 min at 180×g, 4° C. Cell pellets were fixed in 500 μL 4% paraformaldehyde (Electron Microscopy Sciences, Hatfield, Pa.) for 15 min at room temperature protected from light. Samples were centrifuged for 5 min at 180×g, resuspended in 300 μL DPBS, transferred to 5 mL flow cytometry tubes, and analyzed on a FACSCalibur flow cytometer (BD Biosciences, San Jose, CA) with excitation at 488 nm and 635 nm, Alexa Fluor 488 emission detected with a 530/30 filter and Alexa Fluor 647 emission detected with a 661/16 filter. FlowJo software (BD Biosciences) was used for analysis.

TABLE 1

Antibodies

| Target | Species/ isotype | Manufacturer, clone (product number), RRID | Fluorophore | App.[a] | Dilution |
|---|---|---|---|---|---|
| p75-NGFR | Mouse IgGl | Advanced Targeting Systems, ME20.4 (AB-N07) RRID:AB_171797 | Unconjugated | FC | 0.2 μL/ $10^6$ cells |
| HNK-1 | Mouse IgM | Sigma-Aldrich, VC1.1 (C6680) RRID:AB_1078474 | Unconjugated | FC | 0.2 μL/ $10^6$ cells |
| PDGFRβ | Rabbit IgG | Cell Signaling Technology, 28E1 (3169) RRID :AB_2162497 | Unconjugated | ICC<br>WB | 1:100<br>1:500 |
| Notch3 | Rabbit IgG | Cell Signaling Technology, D11B8 (5276) RRID: AB_10560515 | Unconjugated | ICC<br>WB<br>IP<br>ChIP | 1:100<br>1:1000<br>1:200<br>1:200 |
| Isotype control | Rabbit IgG | Cell Signaling Technology, DAIE (3900) RRID:AB_1550038 | Unconjugated | IP | 1:688 |
| Notch1 | Rabbit IgG | Cell Signaling Technology, D1E11 (3608) RRID:AB_2153354 | Unconjugated | WB | 1:1000 |
| VE-cadherin | Mouse IgG2a | Santa Cruz, BV9 (sc-52751) RRID:AB_628919 | Unconjugated | ICC | 1:100 |
| Tbx2 | Rabbit polyclonal | Prestige Antibodies, (HPA008586) RRID:AB_1080222 | Unconjugated | ICC<br>WB | 1:100<br>1:500 |
| Fibronectin | Mouse IgG1 | Santa Cruz, EP5 (sc-8422) RRID:AB_627598 | Unconjugated | ICC<br>WB | 1:50<br>1:250 |
| Calponin | Mouse IgG1 | Sigma-Aldrich, hCP (C2687) RRID:AB_476840 | Unconjugated | ICC | 1:15,000 |
| SM22α | Rabbit polyclonal | Abcam, (abl4106) RRID:AB_443021 | Unconjugated | ICC | 1:1000 |
| α-SMA | Mouse IgG2a | Lab Vision, 1A4 (MS-113-P) RRID:AB_64000 | Unconjugated | ICC | 1:100 |
| GFP | Mouse IgG2a | Santa Cruz, B-2 (sc-9996) RRID:AB_627695 | Unconjugated | ICC<br>WB | 1:50<br>1:250 |
| RBPJ | Rabbit IgG | Cell Signaling Technology, D10A4 (5313) RRID:AB_2665555 | Unconjugated | WB | 1:1000 |
| β-actin | Rabbit IgG | Cell Signaling Technology, 13E5 (4970) RRID:AB_2223172 | Unconjugated | WB | 1:1000 |
| Rabbit IgG (conformation-specific) | Mouse IgG | Cell Signaling Technology, L27A9 (3678) RRID: RRID:AB_1549606 | Unconjugated | WB | 1:2000 |
| Rabbit IgG | Goat polyclonal | LI-COR, (925-68071) RRID :AB_10956166 | IRDye 680RD | WB | 1:5000 |
| Mouse IgG | Goat polyclonal | LI-COR, (926-68070) RRID:AB_10956588 | IRDye 680RD | WB | 1:5000 |
| Rabbit IgG | Goat polyclonal | LI-COR, (926-32211) RRID :AB_621843 | IRDye 800CW | WB | 1:5000 |
| Mouse IgG | Goat polyclonal | LI-COR, (926-32210) RRID :AB_621842 | IRDye 800CW | WB | 1:5000 |

TABLE 1-continued

| Antibodies | | | | | |
|---|---|---|---|---|---|
| Target | Species/ isotype | Manufacturer, clone (product number), RRID | Fluorophore | App.[a] | Dilution |
| Mouse IgGl | Goat polyclonal | Invitrogen, (A-21240) RRID:AB_2535809 | Alexa Fluor 647 | FC | 1:500 |
| Mouse IgM | Goat polyclonal | Invitrogen, (A-21042) RRID:AB_2535711 | Alexa Fluor 488 | FC | 1:500 |
| Rabbit IgG | Goat polyclonal | Invitrogen, (A-21245) RRID:AB_2535813 | Alexa Fluor 647 | ICC | 1:200 |
| Mouse IgG | Goat polyclonal | Invitrogen, (A-21235) RRID:AB_2535804 | Alexa Fluor 647 | ICC | 1:200 |
| Mouse IgG | Goat polyclonal | Invitrogen, (A-11001) RRID:AB_2534069 | Alexa Fluor 488 | ICC | 1:200 |
| Mouse IgG | Goat polyclonal | Invitrogen, (A-21424) RRID:AB_141780 | Alexa Fluor 555 | ICC | 1:200 |

[a]Application: FC, Flow cytometry; ICC, immunocytochemistry; WB, Western blotting; IP, immunoprecipitation; ChIP: chromatin immunoprecipitation Lentivirus Production The lentiviral plasmids pWPI (Addgene plasmid #12254), psPAX2 (Addgene plasmid #12260), and pMD2.G (Addgene plasmid #12259) were obtained from Addgene (Watertown, Mass.) as gifts from Didier Trono. To generate pWPI-N3ICD, we amplified a cDNA fragment encoding the intracellular domain of Notch3 from a cDNA library generated from hPSC-derived neural crest. This fragment spans nucleotides 5,074-7056 of NCBI Reference Sequence NM_000435.3, corresponding to amino acids 1,662-2,321 of NP_00426.2. To generate pWPI-N1ICD, we amplified a cDNA fragment encoding the intracellular domain of Notch1 from the neural crest cDNA library. This fragment spans nucleotides 5,522-7,930 of NM_017617.5, corresponding to amino acids 1,754-2,556 of NP060087.3. For N3ICD and N1ICD, the forward primers (Table 2) contained a Kozak consensus sequence and start codon; forward and reverse primers (Table 2) included PacI restriction enzyme sites. To generate pWPI-TBX2, we amplified the TBX2 coding sequence from pcDNA3.1-TBX2 (NCBI Reference Sequence NM_005994.4) (GenScript, Piscataway, NJ). The forward primer (Table 2) contained a Kozak consensus sequence; forward and reverse primers (Table 2) included PacI restriction enzyme sites. pWPI and the resulting PCR fragments were digested with PacI. Ligation was performed with Instant Sticky-end Ligase Master Mix (New England Biolabs, Ipswich, MA), and resulting products transformed into NEB Stable Competent *E. coli* (New England Biolabs). Single ampicillin-resistant colonies were picked and PCR screened for presence of insert using primers annealing to the EF-1α promoter and IRES (Table 2). Sanger sequencing was used to identify clones with forward-oriented inserts. pWPI, pWPI-N3ICD, pWPI-N1ICD, and pWPI-TBX2 plasmids were expanded and purified using the EndoFree Plasmid Maxi Kit (Qiagen, Germantown, MD).

293TN cells (System Biosciences, Palo Alto, CA) were maintained on uncoated 6-well plates in DMEM (Life Technologies) supplemented with 10% fetal bovine serum (Peak Serum, Wellington, CO), 1 mM sodium pyruvate (Life Technologies), and 0.5× GlutaMAX Supplement (Life Technologies). When 293TN cells reached 90% confluence, psPAX2 (1 μg/well), pMD2.G (0.5 μg/well), and pWPI or pWPI-N3ICD or pWPI-N1ICD or pWPI-TBX2 (1.5 μg/well) were cotransfected using FuGENE HD Transfection Reagent (9 μL/well) (Promega, Madison, WI). Medium was replaced 16 hours after transfection, and virus-containing supernatants collected 24, 48, and 72 hours later. Supernatants were filtered through a 0.45 μm filter and concentrated 100× using Lenti-X Concentrator (Takara Bio, Mountain View, CA).

TABLE 2

| Primer sequences | | |
|---|---|---|
| Gene | Forward primer sequence | SEQ ID NO: |
| Primers for cloning | | |
| NOTCH3 forward | TAA GCA TTA ATT AAG CCA CCA TGG TCA TGG TGG CCC GG | 7 |
| NOTCH3 reverse | TGC TTA TTA ATT AAT CAG GCC AAC ACT TGC C | 8 |
| NOTCH1 forward | TAA GCA TTA ATT AAG CCA CCA TGG TGC TGC TGT CCC GCA AGC G | 9 |
| NOTCH1 reverse | TGC TTA TTA ATT AAT TAC TTG AAG GCC TCC GGA A | 10 |
| TBX2 forward | TAA GCA TTA ATT AAG CCA CCA TGA GAG AGC CGG CGC | 11 |
| TBX2 reverse | TGC TTA TTA ATT AAT CAC TTG GGC GAC TCC C | 12 |

TABLE 2-continued

| Primer sequences | | |
|---|---|---|
| Gene | Forward primer sequence | SEQ ID NO: |
| EF-1α promoter forward | TCA AGC CTC AGA CAG TGG TTC | 13 |
| IRES reverse | CCT CAC ATT GCC AAA AGA CG | 14 |
| Primers for RT-qPCR | | |
| eGFP forward | GAA CCG CAT CGA GCT GAA | 15 |
| eGFP reverse | TGC TTG TCG GCC ATG ATA TAG | 16 |
| NGFR forward | GTG GGA CAG AGT CTG GGT GT | 17 |
| NGFR reverse | AAG GAG GGG AGG TGA TAG GA | 18 |
| PDGFRB forward | GCT CAC CAT CAT CTC CCT TAT C | 19 |
| PDGFRB reverse | CTC ACA GAC TCA ATC ACC TTC C | 20 |
| RGS5 forward | GGA GGC TCC TAA AGA GGT GAA TA | 21 |
| RGS5 reverse | CCA TCA GGG CAT GGA TTC TTT | 22 |
| KCNJ8 forward | AAC CTG GCG CAT AAG AAC ATC | 23 |
| KCNJ8 reverse | CCA CAT GAT AGC GAA GAG CAG | 24 |
| NOTCH3 forward[a] | GAG ACG CTC GTC AGT TCT TAG | 25 |
| NOTCH3 reverse[a] | GGT GGA AAG AGA AGA GGA TGA A | 26 |
| TBX2 forward | ACA TCC TGA AGC TGC CTT AC | 27 |
| TBX2 reverse | AGC TGT GTG ATC TTG TCA TTC T | 28 |
| HEYL forward | CAG ATG CAA GCC AGG AAG AA | 29 |
| HEYL reverse | GGA AGA GCC CTG TTT CTC AAA | 30 |
| FOXS1 forward | CCA AGG ACA ACC ACA CAG AA | 31 |
| FOXS1 reverse | GCC ACA GAG TAA ATC CCA AGA G | 32 |
| TBX18 forward | CCC AGG ACT CCC TCC TAT GT | 33 |
| TBX18 reverse | TAG GAA CCC TGA TGG GTC TG | 34 |
| FOXF2 forward[b] | ACC AGA GCG TCT GTC AGG ATA TT | 35 |
| FOXF2 reverse[b] | GTG ACT TGA ATC CGT CCC AGT TTC | 36 |
| MYL9 forward | GTC CCA GAT CCA GGA GTT TAA G | 37 |
| MYL9 reverse | CAT CAT GCC CTC CAG GTA TT | 38 |
| NDUFA4L2 forward | AGA GGA CCA GAC TGG GAA A | 39 |
| NDUFA4L2 reverse | CAG GCA GAT TAA GCC GAT CA | 40 |
| HIGD1B forward | CGA AGA CTG TGT GTC TGA GAA G | 41 |
| HIGD1B reverse | CTC AGC CGG TAA ATC CTG TAT G | 42 |
| ACTA2 forward | TGT TCC AGC CAT CCT TCA TC | 43 |
| ACTA2 reverse | GCA ATG CCA GGG TAC ATA GT | 44 |

[a]Primers target 3'UTR and thus do not amplify transgene-derived transcripts
[b]From ref. (103)

Lentiviral Transduction

When neural crest cells reached ~40-50% confluence (~2-3 days post-MACS), lentiviral transduction was performed by replacing medium in each well E6-CSFD medium containing 30-50 μL N3ICD-GFP, N1ICD-GFP, or TBX2-GFP lentivirus per mL, or 5-8 μL GFP (control) lentivirus per mL, which achieved transduction efficiencies of 50-80%. E6-CSFD medium was replaced every other day for 6 days. In some experiments, culture medium was supplemented with 10 μM CB-103 (MedChemExpress, Monmouth Junction, NJ). The resulting cultures were either used directly for analysis or sorted to isolate $GFP^+$ and $GFP^-$ cells as described below.

RT-qPCR

RNA extraction was performed using the RNeasy Plus Micro Kit (Qiagen). Cells were lysed with 350 μL Buffer RLT supplemented with 1% β-mercaptoethanol (Sigma) and transferred to gDNA Eliminator spin columns. 350 μL 70% ethanol was added to each lysate, and lysates were loaded onto RNeasy MinElute spin columns. Columns were washed with Buffer RW1, Buffer RPE, and 80% ethanol according to manufacturer protocols. RNA was eluted with RNase-free water and concentration quantified using a NanoDrop 2000 spectrophotometer (Thermo Scientific, Waltham, MA). 250-1000 ng of RNA was reverse-transcribed for 1 h at 37° C. using the OmniScript RT Kit (Qiagen) and 1 μM Oligo(dT)$_{12-18}$ primers (Life Technologies). 1 U/μL RNaseOUT (Life Technologies) was included in the reverse-transcription reactions. Reaction products were diluted to 10 ng/μL. 20 μL qPCR reactions were carried out with 10 ng cDNA and 500 nM each forward and reverse primers (Table 2) using PowerUp SYBR Green Master Mix (Life Technologies) and an AriaMx Real-Time PCR System (Agilent Technologies, Santa Clara, CA). An annealing temperature of 60° C. was used for all reactions.

Immunoprecipitation

Cells were washed once with DPBS and lysed with Cell Lysis Buffer (Cell Signaling Technology, Danvers, MA) supplemented with 1× Halt Protease Inhibitor Cocktail (Thermo Scientific). Lysates were sonicated with three 5 s pulses at 40% power with a ⅛-inch probe and centrifuged at 4° C. for 5 min, 14,000×g. Supernatants were transferred to new tubes and protein concentrations quantified using the Pierce BCA Protein Assay Kit (Thermo Scientific). Lysates were diluted with lysis buffer to 1 mg/mL. 420 μl of each lysate was precleared by adding 40 μl of prewashed Protein A Magnetic Beads (Cell Signaling Technology) and incubating with rotation for 20 min at room temperature. Beads were removed using a magnetic separation rack. To reduce nonspecific adsorption of DNA to magnetic beads, DNA was fragmented by adding 2 μl (2000 U) micrococcal nuclease to each lysate and incubating for 30 min at 37° C. Digestion was stopped by adding 10 μl of 0.5 M EDTA to each lysate. A 20 μl aliquot of each lysate was removed and stored at −80° C. to serve as a 10% input control. The remaining 400 μl of each lysate was split between two new tubes, and Notch3 or isotype control antibody (at matched concentration, Table 1) added. Lysates were incubated with rotation overnight at 4° C. 20 μl of prewashed Protein A Magnetic Beads were added to each lysate and incubated with rotation for 20 min at room temperature. Beads were pelleted using a magnetic separation rack, supernatant removed, and beads washed with 500 μl of lysis buffer. This step was repeated for a total of 5 washes. After the final wash, beads were pelleted, supernatant removed, and beads resuspended in 20 μl of Western blot sample buffer. 20 μl Western blot sample buffer was also added to each 10% input sample. All samples were heated at 95° C. for 5 min. Beads were pelleted via centrifugation and resulting supernatants and 10% input samples processed for anti-RBPJ Western blotting as described below, except a mouse anti-rabbit IgG conformation-specific secondary antibody (Table 1) was used for detection.

Western Blotting

Cells were lysed with radioimmunoprecipitation assay (RIPA) buffer (Rockland Immunochemicals, Pottstown, PA) supplemented with 1× Halt Protease Inhibitor Cocktail and centrifuged at 4° C. for 5 min, 14,000× g. Supernatants were collected, transferred to new tubes, and protein concentrations quantified using the Pierce BCA Protein Assay Kit. For each sample, ~20 μg of protein was diluted to equal volume with water, mixed with sample buffer, and heated at 95° C. for 5 min. Samples were resolved on 4-12% Tris-Glycine gels and transferred to nitrocellulose membranes. Membranes were blocked for 1 h in tris-buffered saline plus 0.1% Tween-20 (TBST) supplemented with 5% non-fat dry milk. Primary antibodies (Table 1) were diluted in TBST supplemented with 5% non-fat dry milk and were added to membranes and incubated overnight at 4° C. on a rocking platform. Membranes were washed five times with TB ST. Secondary antibodies (Table 1) were diluted in TBST supplemented with 5% non-fat dry milk and were added to membranes and incubated for 1 h at room temperature on a rocking platform, protected from light. Membranes were washed five times with TBST and imaged using an Odyssey 9120 (LI-COR, Lincoln, NE). Band intensities were quantified using Image Studio software (LI-COR).

Fluorescence-Activated Cell Sorting (FACS) and Post-FACS Culture 6 days after lentiviral transduction, cells were dissociated using ~30 min of Accutase treatment, 1 mL per well. The Accutase/single cell suspension was transferred to 4× volume of DMEM/F12 medium and centrifuged for 5 min at 200×g. The cell pellet was resuspended in MACS buffer supplemented with 2 μg/mL 4',6-diamidino-2-phenylindole (DAPI; Life Technologies). A FACSAria III Cell Sorter (BD Biosciences) was used to isolate $DAPI^-$ $GFP^+$ cells (live, N3ICD-overexpressing cells) and $DAPI^-GFP^-$ cells (live, non-overexpressing cells). Excitation was at 405 nm and 488 nm, with DAPI emission detected with a 450/50 filter and GFP emission detected with a 502LP dichroic and 530/30 filter. Cells from a non-transduced well were used as a gating control. The resulting cell suspensions were centrifuged for 5 min at 200×g, 4° C. Cell pellets were resuspended in E6 medium and seeded on Matrigel-coated plates at $2\times10^4$ cells/$cm^2$. Medium was replaced daily.

Immunocytochemistry

Cells were washed once with DPBS and fixed with 4% paraformaldehyde for 15 min. Cells were washed three times with DPBS and blocked/permeabilized with DPBS supplemented with 10% goat serum (Life Technologies) and 0.1% Triton-X100 (Sigma-Aldrich) for 1 h at room temperature. Primary antibodies (Table 1) diluted in DPBS supplemented with 10% goat serum were added to cells and incubated overnight at 4° C. on a rocking platform. Cells were washed three times with DPBS. Secondary antibodies (Table 1) diluted in DPBS supplemented with 10% goat serum were added to cells and incubated for 1 h at room temperature on a rocking platform, protected from light. Cells were washed three times with DPBS. Cells were incubated for 5 min in DPBS supplemented with 4 μM Hoechst 33342 (Life Technologies). Images were acquired using an Eclipse Ti2-E epifluorescence microscope (Nikon, Tokyo, Japan) with a 20× objective.

RNA-Seq

RNA-seq was performed on cells from the H9, IMR90-4, DF19-9-11T, and WTC11 hPSC lines. For each line, differentiation-matched samples of neural crest cells, and $GFP^-$ and $GFP^+$ cells isolated via FACS 6 days after transduction of neural crest with N3ICD-GFP lentivirus, were analyzed. Neural crest cells were dissociated with Accutase for ~5 min. The Accutase/single cell suspension was transferred to 4× volume of DMEM/F12 medium and centrifuged for 5 min at 200×g, 4° C. FACS was performed as described above; resulting $GFP^-$ and $GFP^+$ populations were centrifuged for 5 min at 200×g, 4° C. Supernatants were aspirated and the resulting cell pellets immediately lysed with Buffer RLT Plus (Qiagen) supplemented with 1% β-mercaptoethanol and frozen at −80° C. RNA extraction was performed using the RNeasy Plus Micro Kit (Qiagen). Lysates were thawed on ice, processed through gDNA Eliminator spin columns, processed through RNeasy MinElute spin columns per manufacturer instructions, and eluted into RNase-free water.

RNA quality control, library preparation, and sequencing were performed by Novogene (Sacramento, CA). RNA quantity was assessed using a NanoDrop spectrophotometer; RNA quality was assessed using an Agilent 2100 Bioanalyzer. Poly(A) mRNA enrichment was performed using poly(T) oligo-conjugated magnetic beads, first-strand cDNA synthesis performed using random hexamer primers, second-strand cDNA synthesis performed, and libraries prepared using the NEBNext Ultra II RNA Library Prep Kit for Illumina (New England Biolabs). Libraries were sequenced on a NovaSeq 6000 (Illumina, San Diego, CA) with approximately 20 million 150 bp paired-end reads obtained for each sample.

RNA-Seq Data Analysis

A DNA sequence from lentiviral transfer plasmid pWPI extending from the PacI site to the 3' end of the WPRE (containing the IRES and eGFP CDS) was added to the reference genome (hg38) to permit quantification of transgene-derived transcripts. RNA-seq FASTQ files from the experiment described above and from the literature (obtained from the Gene Expression Omnibus, Table 3) were aligned to the resulting reference genome using STAR (version 2.5.3a) (82). Gene-level counts were generated using the featureCounts function from Subread (version 2.0.3) (83). Transcripts per million (TPM) were calculated using gene lengths derived from featureCounts as previously described (35).

TABLE 3

Published RNA-seq datasets used

| Reference | Description | Source | Accession Numbers/Identifiers |
|---|---|---|---|
| (38) | hPSC-derived brain pericyte-like cells | https://www.ncbi.nlm.nih.gov/geo/query/acc.cgi?acc=GSE124579 | GSM3537065 (SRR8385490, SRR8385491)<br>GSM3537067 (SRR8385494, SRR8385495)<br>GSM3537068 (SRR8385496, SRR8385497)<br>GSM3537069 (SRR8385498, SRR8385499)<br>GSM3537070 (SRR8385500, SRR8385501) |
| (40) | hPSC-derived brain pericyte-like cells | https://www.ncbi.nlm.nih.gov/geo/query/acc.cgi?acc=GSE104141 | GSM2790557 (SRR6059668)<br>GSM2790558 (SRR6059669)<br>GSM2790559 (SRR6059670) |
| (41) | hPSC-derived brain pericyte-like cells | https://www.ncbi.nlm.nih.gov/geo/query/acc.cgi?acc=GSE132857 | GSM3895132 (SRR9312712)<br>GSM3895133 (SRR9312713)<br>GSM3895134 (SRR9312714)<br>GSM3895135 (SRR9312715) |
| (93) | Mouse developing brain scRNA-seq | http://mousebrain.org/development/downloads.html | dev_all.loom |
| (36) | Meta-analysis of human brain scRNA-seq datasets (enumerated below) | | |
| (84) | Adult human neocortex ScRNA-seq | https://portal.bram-map.org/atlases-and-data/rnaseq/human-multiple-cortical-areas-smart-seq | |
| (85) | GW17-18 human neocortex ScRNA-seq | http://solo.bmap.ucla.edu/shiny/webapp/ | |
| (87) | Adult human temporal lobe and cerebellum scRNA-seq | https://www.ncbi.nlm.nih.gov/geo/query/acc.cgi?acc=GSE134355 | GSM3980129, GSM4008656, GSM4008657, GSM4008658 |
| (86) | GW6-11 human ventral midbrain scRNA-seq | https://www.ncbi.nlm.nih.gov/geo/query/acc.cgi?acc=GSE76381 | |
| (88) | GW16-27 human hippocampus scRNA-seq | https://www.ncbi.nlm.nih.gov/geo/query/acc.cgi?acc=GSE119212 | |

Transcriptome comparison between hPSC-derived brain pericyte-like cells, $GFP^+$ cells from this work, and in vivo human brain pericytes was performed for protein-coding genes (based on the list at genenames.org/download/statistics-and-files). Data for in vivo brain pericytes were obtained from a previous meta-analysis of single cell RNA-seq studies (36). In this meta-analysis, a mock bulk RNA-seq dataset was constructed from each source dataset (84-88) by (i) averaging gene counts across the pericyte cluster, (ii) obtaining the subset of protein-coding genes, and (iii) generating mock TPM values by normalizing total counts to $10^6$. Bulk RNA-seq TPM values from hPSC-derived brain pericyte-like cells (from the literature) and $GFP^+$ cells (this work) were similarly re-normalized to $10^6$ after obtaining the subset of protein-coding genes. To generate the scatterplots FIG. 6A and FIG. 8G, resulting TPM values for each gene across the 11 hPSC-derived brain pericyte-like cell datasets or 4 $GFP^+$ cell datasets were averaged, and TPM values for each gene across the 5 in vivo human brain pericyte datasets were averaged, followed by log-transformation as log 2 (TPM+1). The Pearson correlation coefficients were calculated based on the log-transformed average TPM values.

Raw counts from featureCounts were input to DESeq2 (version 1.32.0) (89) for differential expression and principal component analyses. The DESeq2 variance stabilizing transformation was used to generate counts data for input to principal component analysis and hierarchical clustering. Hierarchical clustering on genes and samples (one minus Pearson correlation with average linkage) was performed using Morpheus (software.broadinstitute.org/morpheus/). Differential expression analysis was performed using the DESeq2 Wald test with Benjamini-Hochberg correction. The DESeq2 design included differentiation (hPSC line) matching as described above. Genes with adjusted P-values <0.05 were considered differentially expressed. Gene Set Enrichment Analysis (version 4.2.3) (90) was performed using DESeq2-normalized counts for neural crest and $GFP^+$ cell samples. GSEA was performed with gene set permutation and otherwise default settings. Genes enriched in $GFP^+$ cells compared to neural crest were tested against the KEGG (91) and gene ontology-biological processes (GO-BP, (92)) databases (version 7.5.1). Gene sets with false discovery rates (FDR)<0.05 were considered enriched. Visualization of reads aligned to the human genome was performed using Integrative Genomics Viewer (version 2.5.0).

Analysis of single cell RNA-seq data from developing mouse brain (93) was performed in Scanpy (94) (version 1.9.1). The loom file containing expression data and metadata was obtained from the authors' website (Table 3). Clusters annotated as neural crest and mesenchymal cell types by the authors were selected for analysis. A complete list of the authors' ClusterName identifiers is shown in FIG. 7A, along with the authors' Subclass, Age, and PseudoAge annotations. For visualization, we selected of highly variable genes, regressed out total counts and percent of counts derived from mitochondrial genes, and performed principal component analysis, neighbor finding, and UMAP embedding (40 principal components) using Scanpy default parameters. A dot plot was used to visualize expression of neural crest, pan-mesenchymal, fibroblast, pan-mural, pericyte, and VSMC markers.

Decellularization and Quantification of Extracellular Matrix

Decellularization was performed 6 days after transduction of neural crest cultures in 12-well plates with GFP or N3ICD-GFP lentiviruses as described above. The decellularization protocol was adapted from ref (95). The following buffers were pre-warmed to 37° C.: DPBS, Wash Buffer 1 (100 mM disodium phosphate, 2 mM magnesium chloride, 2 mM EDTA, pH 9.6), Lysis Buffer (8 mM disodium phosphate, 1% Triton X-100, pH 9.6), Wash Buffer 2 (10 mM disodium phosphate, 300 mM potassium iodide, pH 7.5). Cells were washed twice with 1 mL DPBS and three times with 1 mL Wash Buffer 1. Cells were incubated with 1 mL Lysis Buffer for 15 min at 37° C. Lysis Buffer was replaced with 1 mL fresh Lysis Buffer; cells were incubated for 1 h at 37° C. Lysis Buffer was replaced with 1 mL fresh Lysis Buffer; cells were incubated for an additional 1 h at 37° C. Lysis Buffer was removed and the resulting extracellular matrix washed 3 times with 1 mL Wash Buffer 2 and 4 times with 1 mL water. Water was removed and 250 μL RIPA buffer added. Extracellular matrix was scraped from the bottom of the well. The resulting solution was transferred to a microcentrifuge tube and sonicated with two 10 s pulses at 40% power with a ⅛-inch probe. Protein concentration in the resulting solution was quantified using the BCA assay. For normalization of total protein to cell number, cells from a parallel well of the 12-well plate were dissociated using Accutase and counted using a hemocytometer.

Cord Formation Assays

The coculture cord formation assay was performed 5 days after isolation of $GFP^+$ and $GFP^-$ cells via FACS from a N3ICD-GFP-transduced culture as described above. 8-well chamber slides were coated with Matrigel, growth factor reduced, at 250 μL per well. Matrigel was allowed to gel at 37° C. for 1 h. HUVECs (American Type Culture Collection, Manassas, VA) maintained in EGM-2 medium (Lonza, Walkersville, MD), were dissociated using a ~15 min treatment with 0.25% trypsin-EDTA (Gibco). The resulting cell suspension was transferred to a 4× volume of DMEM supplemented with 10% FBS. Neural crest cells, $GFP^+$ cells, and $GFP^-$ cells were dissociated using 5-15 min of Accutase treatment and the resulting cell suspensions were transferred to 4× volumes of DMEM/F12 medium. Cells were counted using a hemocytometer and centrifuged for 5 min at 200×g. Supernatants were removed and cell pellets resuspended in 1 mL EGM-2 medium. For the HUVEC-only control, HUVEC cell suspension and EGM-2 medium were combined to yield a suspension containing $2.2\times10^4$ HUVECs per 500 μL. For the coculture conditions, HUVEC cell suspension, coculture cell suspension (neural crest, $GFP^+$, or $GFP^-$ cell suspension), and EGM-2 medium were combined to yield suspensions containing $2.2\times10^4$ HUVECs and $6.6\times10^4$ coculture cells per 500 μL. 500 μL of the resulting cell suspensions were added to the prepared wells of the 8-well chamber slides. Phase contrast and GFP images were acquired after 24 h and 72 h using an Eclipse Ti2-E microscope with a 4× objective.

To assess the ability of extracellular matrix from GFP- and N3ICD-GFP-transduced cells to support endothelial cord formation, neural crest cultures in 48-well plates 6 days post-transduction with GFP or N3ICD-GFP lentiviruses were decellularized. The decellularization protocol was as described above, except all wash and incubation steps performed using 200 μL of solution, and the protocol terminated after the final wash with water. This procedure was also performed on parallel cell-free wells to serve as a no-extracellular matrix control. Additional parallel wells were coated with 200 μL Matrigel, Growth Factor Reduced, which was allowed to gel at 37° C. for 1 h. $2.75\times10^4$ HUVECs in 250 μL EGM-2 medium were added to each well. Phase contrast images were acquired 16 h after addition of HUVECs using an Eclipse Ti2-E microscope with a 4× objective. Cells were subsequently fixed and processed for VE-cadherin immunocytochemistry as described above. To quantify the extent of cord formation, blinded phase contrast images were scored on the following 4-point scale. 0: No cords apparent. 1: Few cords apparent, most cells not associated with cords. 2: Many cords apparent, most cells associated with cords. 3: Virtually all cells associated with cords.

Calcium Imaging and Contraction Assay

Calcium imaging was performed 6 days after transduction of a neural crest cultures with N3ICD-GFP lentivirus as described above. FLIPR Calcium 6 dye (Molecular Devices, San Jose, Calif.) was prepared according to manufacturer instructions. 500 μL of prepared dye was added to the existing 500 μL of culture medium and cells incubated at 37° C., 5% $CO_2$ for 2 h. The plate was transferred to a microscope environmental chamber at 37° C., 5% $CO_2$ and equilibrated for 30 min. Images were acquired every 5 s for 300 s using an Eclipse Ti2-E microscope with a 4× objective. At t=50 s, a 1:114 dilution of saturated KCl solution (4.56 M, for a final concentration of 40 mM) was added to the well. ImageJ was used to quantify mean fluorescence intensity $F_t$ at each time point and data are displayed as $\Delta F/F=(F_t-F_0)/F_0$.

To assess function of $K_{ATP}$ channels, cells 6 days after transduction with GFP or N3ICD-GFP lentiviruses were labeled with FLIPR Calcium 6 dye as above, and 20 μM pinacidil (Santa Cruz Biotechnology, Dallas, TX) or DMSO added 1.5 h after addition of dye. After an additional 30 min incubation, the plate was transferred to the microscope environmental chamber. Images were acquired every 5 s for 60 s and 40 mM KCl added at t=20 s. Mean fluorescence intensity was quantified as above.

The contraction assay was performed 2 days after isolation of $GFP^+$ cells via FACS from a N3ICD-GFP-transduced culture as described above. The plate was transferred to a microscope environmental chamber at 37° C., 5% $CO_2$ and equilibrated for 30 min. At t=0 min, a 1:114 dilution of saturated potassium chloride solution, or an equivalent volume of water, was added to the culture medium and the plate briefly rocked to mix. Phase contrast images were acquired immediately upon addition of potassium chloride or water and 15 min thereafter using an Eclipse Ti2-E microscope with a 20× objective. The Freehand Selection Tool in ImageJ was used to trace the outlines of 16 cells per 20× field at times 0 and 15 min, and the Measure function used to obtain $A_0$ and $A_{15}$, the cell areas at times 0 and 15 min, respectively. For each cell, the percent change in area was computed as $(A_{15}-A_0)/A_0\times100\%$. These values were averaged across the 16 cells in each field to generate the values shown in FIG. 4.

ChIP-Seq

ChIP-seq was performed on cells 6 days after transduction of neural crest cultures with GFP and N3ICD-GFP lentivirus as described above. Three independent differentiations were performed, with average transduction efficiency of GFP-transduced cultures 82±9% $GFP^+$ and N3ICD-GFP-transduced cultures 87±3% $GFP^+$. Cells were dissociated with Accutase and transferred to DMEM/F-12. Crosslinking was performed with 1% formaldehyde for 10 min and the reaction quenched with glycine. Cells were centrifuged for 5 min at 2,000×g, 4° C. Supernatants were removed and cell pellets stored at −80° C. Nuclei isolation and chromatin digestion with micrococcal nuclease were performed using the SimpleChIP Enzymatic Chromatin IP Kit (Magnetic Beads) (Cell Signaling Technology) according to manufacturer protocols. 50 μl of resulting chromatin preparation from a GFP-transduced sample was subject to crosslink reversal and DNA purification to confirm appropriate digestion and estimate chromatin concentration. Approximately 60 μg of chromatin was used for each immunoprecipitation. Samples were diluted to 500 μL and Notch3 antibody (Table 1) added. Samples were incubated overnight with rotation at 4° C. Antibody-bound fragments were isolated using Protein G magnetic beads. Resulting chromatin samples and matched 10% input control samples were subject to cross-links reversal and DNA purification using the SimpleChIP Enzymatic Chromatin IP Kit, per manufacturer protocols. DNA quality control, library preparation, and sequencing were performed by Novogene. Libraries were sequenced on a NovaSeq 6000 with approximately 30 million 150 bp paired-end reads obtained for each sample.

ChIP-Seq Data Analysis

Sequencing reads were aligned to the human genome (hg38) using bowtie2 (version 2.2.1) (96). Sambamba (version 0.8.2) and bedtools (version 2.30.0) were used to remove unmapped reads, reads mapped to blacklist regions (using the database available at https://github com/Boyle-Lab/Blacklist) (97), and reads mapped to decoys and non-chromosomal assemblies. Peakcalling was performed with MACS (version 3.0.0a7) (98), using IP and matched input control samples, paired-end mode, and a P-value cutoff of 0.0005. DiffBind (version 3.2.7) (59) calling DESeq2 (89) was used to identify peaks enriched in N3ICD-GFP-transduced samples compared to GFP-transduced samples (adjusted P-value <0.05, DESeq2 Wald test with Benjamini-Hochberg correction). ChIPseeker (version 1.28.3) (99) was used for peak annotation. DeepTools (version 3.5.1) (100) was used to generate bigWig files and peak profile plots. MEME-ChIP (https://meme-suite.org/meme/tools/meme-chip, version 5.4.1) (101) was used for motif enrichment analysis. Genome browser visualizations were created using the UCSC Genome Browser (102).

Statistics

Individual wells of cultured cells that underwent identical experimental treatments are defined as replicates. Details of replication strategy are provided in figure legends. Student's unpaired or paired t tests were used for comparison of means from two experimental groups. One-way analysis of variance (ANOVA) was used for comparison of means from three or more experimental groups. Two- or three-way ANOVA was used for comparison of means and blocking of differentiation-based variability if data from multiple differentiations were combined (one/two factors being the experimental treatment(s) and one factor being the differentiation). Following ANOVA, Dunnett's post-hoc test was used for comparison of multiple treatments to a single control, or Tukey's honest significant difference (HSD) test was used for multiple pairwise comparisons. For cord formation score data, the nonparametric Kruskal-Wallis test was used followed by the Steel-Dwass test for multiple pairwise comparisons.

REFERENCES

1. A. Armulik, A. Abramsson, C. Betsholtz, Endothelial/pericyte interactions. *Circ. Res.* 97, 512-523 (2005).
2. A. Armulik, G. Genové, C. Betsholtz, Pericytes: Developmental, Physiological, and Pathological Perspectives, Problems, and Promises. *Dev. Cell* 21, 193-215 (2011).
3. P. S. Hosford, et al., A critical role for the ATP-sensitive potassium channel subunit KIR6.1 in the control of cerebral blood flow. *J. Cereb. Blood Flow Metab.* 39, 2089-2095 (2019).

4. A. M. Nikolakopoulou, et al., Pericyte loss leads to circulatory failure and pleiotrophin depletion causing neuron loss. *Nat. Neurosci.* 22, 1089-1098 (2019).
5. K. Kisler, et al., Acute Ablation of Cortical Pericytes Leads to Rapid Neurovascular Uncoupling. *Front. Cell. Neurosci.* 14, 1-8 (2020).
6. K. Kisler, et al., Pericyte degeneration leads to neurovascular uncoupling and limits oxygen supply to brain. *Nat. Neurosci.* 20, 406-416 (2017).
7. C. N. Hall, et al., Capillary pericytes regulate cerebral blood flow in health and disease. *Nature* 508, 55-60 (2014).
8. R. A. Hill, et al., Regional Blood Flow in the Normal and Ischemic Brain Is Controlled by Arteriolar Smooth Muscle Cell Contractility and Not by Capillary Pericytes. *Neuron* 87, 95-110 (2015).
9. C. M. Peppiatt, C. Howarth, P. Mobbs, D. Attwell, Bidirectional control of CNS capillary diameter by pericytes. *Nature* 443, 700-704 (2006).
10. R. L. Rungta, E. Chaigneau, B.-F. F. Osmanski, S. Charpak, Vascular Compartmentalization of Functional Hyperemia from the Synapse to the Pia. *Neuron* 99, 362-375.e4 (2018).
11. A. Armulik, et al., Pericytes regulate the blood-brain barrier. *Nature* 468, 557-561 (2010).
12. R. D. Bell, et al., Pericytes Control Key Neurovascular Functions and Neuronal Phenotype in the Adult Brain and during Brain Aging. *Neuron* 68, 409-427 (2010).
13. R. Daneman, L. Zhou, A. A. Kebede, B. A. Barres, Pericytes are required for blood-brain barrier integrity during embryogenesis. *Nature* 468, 562-6 (2010).
14. S. Grubb, et al., Precapillary sphincters maintain perfusion in the cerebral cortex. *Nat. Commun.* 11, 395 (2020).
15. D. A. Hartmann, et al., Brain capillary pericytes exert a substantial but slow influence on blood flow. *Nat. Neurosci.* 24, 633-645 (2021).
16. R. D. Bell, et al., Apolipoprotein e controls cerebrovascular integrity via cyclophilin A. *Nature* 485, 512-516 (2012).
17. M. R. Halliday, et al., Accelerated pericyte degeneration and blood-brain barrier breakdown in apolipoprotein E4 carriers with Alzheimer's disease. *J. Cereb. Blood Flow Metab.* 36, 1-9 (2015).
18. R. Nortley, et al., Amyloid β oligomers constrict human capillaries in Alzheimer's disease via signaling to pericytes. *Science* (80-.). 365, eaav9518 (2019).
19. A. Joutel, et al., The ectodomain of the Notch3 receptor accumulates within the cerebrovasculature of CADASIL patients. *J. Clin. Invest.* 105, 597-605 (2000).
20. M. Ghosh, et al., Pericytes are involved in the pathogenesis of cerebral autosomal dominant arteriopathy with subcortical infarcts and leukoencephalopathy. *Ann. Neurol.* 78,887-900 (2015).
21. H. C. Etchevers, C. Vincent, N. M. Le Douarin, G. F. Couly, The cephalic neural crest provides pericytes and smooth muscle cells to all blood vessels of the face and forebrain. Development 128, 1059-1068 (2001).
22. J. Korn, et al., Neuroectodermal origin of brain pericytes and vascular smooth muscle cells. *J. Comp. Neurol.* 442, 78-88 (2002).
23. E. Yamanishi, M. Takahashi, Y. Saga, N. Osumi, Penetration and differentiation of cephalic neural crest-derived cells in the developing mouse telencephalon. *Dev. Growth Differ.* 54, 785-800 (2012).
24. C. S. Le Lièvre, N. M. Le Douarin, Mesenchymal derivatives of the neural crest: analysis of chimaeric quail and chick embryos. *J. Embryol. Exp. Morphol.* 34, 125-154 (1975).
25. H. C. Etchevers, G. Couly, C. Vincent, N. M. Le Douarin, Anterior cephalic neural crest is required for forebrain viability. Development 126, 3533-43 (1999).
26. X. Jiang, S. Iseki, R. E. Maxson, H. M. Sucov, G. M. Morriss-Kay, Tissue Origins and Interactions in the Mammalian Skull Vault. *Dev. Biol.* 241, 106-116 (2002).
27. P. Lindahl, B. R. Johansson, P. Levéen, C. Betsholtz, Pericyte loss and microaneurysm formation in PDGF-B-deficient mice. *Science* (80-.). 277, 242-245 (1997).
28. M. Hellström, M. Kalén, P. Lindahl, A. Abramsson, C. Betsholtz, Role of PDGF-B and PDGFR-beta in recruitment of vascular smooth muscle cells and pericytes during embryonic blood vessel formation in the mouse. *Development* 126, 3047-3055 (1999).
29. K. Ando, et al., Peri-arterial specification of vascular mural cells from naïve mesenchyme requires Notch signaling. *Development* 146 (2019).
30. Y. Wang, L. Pan, C. B. Moens, B. Appel, Notch3 establishes brain vascular integrity by regulating pericyte number. *Development* 141, 307-317 (2014).
31. H. Wurdak, Inactivation of TGFβ signaling in neural crest stem cells leads to multiple defects reminiscent of DiGeorge syndrome. *Genes Dev.* 19, 530-535 (2005).
32. N. M. Shah, a K. Groves, D. J. Anderson, Alternative neural crest cell fates are instructively promoted by TGFbeta superfamily members. *Cell* 85, 331-43 (1996).
33. L. Menendez, et al., Wnt signaling and a Smad pathway blockade direct the differentiation of human pluripotent stem cells to multipotent neural crest cells. *Proc. Natl. Acad. Sci.* 109, 9220-9220 (2012).
34. G. Lee, et al., Isolation and directed differentiation of neural crest stem cells derived from human embryonic stem cells. *Nat. Biotechnol.* 25 (2007).
35. H. W. Song, et al., Transcriptomic comparison of human and mouse brain microvessels. *Sci. Rep.* 10, 12358 (2020).
36. B. D. Gastfriend, K. L. Foreman, M. E. Katt, S. P. Palecek, E. V. Shusta, Integrative analysis of the human brain mural cell transcriptome. *J. Cereb. Blood Flow Metab.* 41, 3052-3068 (2021).
37. B. D. Gastfriend, S. P. Palecek, E V Shusta, Modeling the blood-brain barrier: Beyond the endothelial cells. *Curr. Opin. Biomed. Eng.* 5, 6-12 (2018).
38. M. J. Stebbins, et al., Human pluripotent stem cell-derived brain pericyte-like cells induce blood-brain barrier properties. *Sci. Adv.* 5, eaau7375 (2019).
39. B. D. Gastfriend, M. J. Stebbins, F. Du, E. V. Shusta, S. P. Palecek, Differentiation of Brain Pericyte-Like Cells from Human Pluripotent Stem Cell-Derived Neural Crest. *Curr. Protoc.* 1, 1-32 (2021).
40. C. Griffin, R. Bajpai, Neural Crest-Derived Human Cranial Pericytes Model Primary Forebrain Pericytes and Predict Disease-Specific Cranial Vasculature Defects. *SSRN Electron. J.* (2018) https:/doi.org/10.2139/ssrn.3189103.
41. J. Sun, et al., Transplantation of hPSC-derived pericyte-like cells promotes functional recovery in ischemic stroke mice. *Nat. Commun.* 11 (2020).
42. P. D. Langridge, G. Struhl, Epsin-Dependent Ligand Endocytosis Activates Notch by Force. *Cell* 171, 1383-1396.e12 (2017).

43. R. Lehal, et al., Pharmacological disruption of the Notch transcription factor complex. *Proc. Natl. Acad. Sci. U.S.A* 117, 16292-16301 (2020).

44. G. La Manno, et al., Molecular architecture of the developing mouse brain. *bioRxiv* (2020) https:/doi.org/10.1101/2020.07.02.184051.

45. M. Vanlandewijck, et al., A molecular atlas of cell types and zonation in the brain vasculature. *Nature* 554, 475-480 (2018).

46. R. Soldatov, et al., Spatiotemporal structure of cell fate decisions in murine neural crest. *Science* (80-.). 364, eaas9536 (2019).

47. J. A. Siegenthaler, et al., Foxc1 is required by pericytes during fetal brain angiogenesis. *Biol. Open* 2, 647-659 (2013).

48. A. Reyahi, et al., Foxf2 Is Required for Brain Pericyte Differentiation and Development and Maintenance of the Blood-Brain Barrier. *Dev. Cell* 34, 19-32 (2015).

49. D. Bhattacharya, M. Rothstein, A. P. Azambuja, M. Simoes-Costa, Control of neural crest multipotency by Wnt signaling and the Lin28/let-7 axis. *Elife* 7, 1-24 (2018).

50. A. C. Yang, et al., A human brain vascular atlas reveals diverse mediators of Alzheimer's risk. *Nature* 603, 885-892 (2022).

51. F. J. Garcia, et al., Single-cell dissection of the human brain vasculature. *Nature* 603, 893-899 (2022).

52. Y. Kubota, H. K. Kleinman, G. R. Martin, T. J. Lawley, Role of laminin and basement membrane in the morphological differentiation of human endothelial cells into capillary-like structures. *J. Cell Biol.* 107, 1589-1598 (1988).

53. A. Kumar, et al., Specification and Diversification of Pericytes and Smooth Muscle Cells from Mesenchymoangioblasts. *Cell Rep.* 19, 1902-1916 (2017).

54. B. Lilly, S. Kennard, Differential gene expression in a coculture model of angiogenesis reveals modulation of select pathways and a role for Notch signaling. *Physiol. Genomics* 36, 69-78 (2009).

55. D. A. Hartmann, V. Coelho-Santos, A. Y. Shih, Pericyte Control of Blood Flow Across Microvascular Zones in the Central Nervous System. *Annu. Rev. Physiol.* 84, 1-24 (2022).

56. A. L. Gonzales, et al., Contractile pericytes determine the direction of blood flow at capillary junctions. *Proc. Natl. Acad. Sci. U.S.A* 117, 27022-27033 (2020).

57. S. A. Zambach, et al., Precapillary sphincters and pericytes at first-order capillaries as key regulators for brain capillary perfusion. *Proc. Natl. Acad. Sci.* 118 (2021).

58. S. J. Bray, M. Gomez-Lamarca, Notch after cleavage. *Curr. Opin. Cell Biol.* 51, 103-109 (2018).

59. R. Stark, G. Brown, DiffBind: differential binding analysis of ChIP-Seq peak data.

60. D. Castel, et al., Dynamic binding of RBPJ is determined by notch signaling status. *Genes Dev.* 27, 1059-1071 (2013).

61. R. S. Ziffra, et al., Single-cell epigenomics reveals mechanisms of human cortical development. *Nature* 598, 205-213 (2021).

62. Y. Luo, et al., New developments on the Encyclopedia of DNA Elements (ENCODE) data portal. *Nucleic Acids Res.* 48, D882-D889 (2020).

63. J. A. Castro-Mondragon, et al., *JASPAR* 2022: The 9th release of the open-access database of transcription factor binding profiles. *Nucleic Acids Res.* 50, D165-D173 (2022).

64. S. Chen, R. J. Lechleider, Transforming growth factor-beta-induced differentiation of smooth muscle from a neural crest stem cell line. *Circ. Res.* 94, 1195-202 (2004).

65. K. K. Hirschi, S. A. Rohovsky, P. A. D'Amore, PDGF, TGF-beta, and heterotypic cell-cell interactions mediate endothelial cell-induced recruitment of 10T1/2 cells and their differentiation to a smooth muscle fate. *J. Cell Biol.* 141, 805-814 (1998).

66. L. He, et al., Analysis of the brain mural cell transcriptome. *Sci. Rep.* 6, 35108 (2016).

67. C. Cheung, A. S. Bernardo, M. W. B. Trotter, R. A. Pedersen, S. Sinha, Generation of human vascular smooth muscle subtypes provides insight into embryological origin-dependent disease susceptibility. *Nat. Biotechnol.* 30, 165-173 (2012).

68. C. Cheung, Y. T. Y. Y. T. Y. Y. T. Goh, J. Zhang, C. Wu, E. Guccione, Modeling cerebrovascular pathophysiology in amyloid-β metabolism using neural-crest-derived smooth muscle cells. *Cell Rep.* 9, 391-401 (2014).

69. C. Patsch, et al., Generation of vascular endothelial and smooth muscle cells from human pluripotent stem cells. *Nat. Cell Biol.* 17, 994-1003 (2015).

70. T. Faal, et al., Induction of Mesoderm and Neural Crest-Derived Pericytes from Human Pluripotent Stem Cells to Study Blood-Brain Barrier Interactions. *Stem Cell Reports* 12, 451-460 (2019).

71. K. Ando, et al., KCNJ8/ABCC9-containing K-ATP channel modulates brain vascular smooth muscle development and neurovascular coupling. *Dev. Cell,* 1-17 (2022).

72. L. A. Brown, P. Sava, C. Garcia, A. L. Gonzalez, Proteomic Analysis of the Pericyte Derived Extracellular Matrix. *Cell. Mol. Bioeng.* 8, 349-363 (2015).

73. A. Montagne, et al., Pericyte degeneration causes white matter dysfunction in the mouse central nervous system. *Nat. Med.* 24, 326-337 (2018).

74. J. W. Blanchard, et al., Reconstruction of the human blood-brain barrier in vitro reveals a pathogenic mechanism of APOE4 in pericytes. *Nat. Med.* 26, 952-963 (2020).

75. B. D. Gastfriend, et al., Wnt signaling mediates acquisition of blood-brain barrier properties in naïve endothelium derived from human pluripotent stem cells. *Elife* 10 (2021).

76. H. Nishihara, et al., Intrinsic blood-brain barrier dysfunction contributes to multiple sclerosis pathogenesis. *Brain* (2022) https:/doi.org/10.1093/brain/awac019.

77. J. A. Thomson, Embryonic stem cell lines derived from human blastocysts. *Science* (80-.). 282, 1145-1147 (1998).

78. J. Yu, et al., Induced pluripotent stem cell lines derived from human somatic cells. *Science* 318, 1917-20 (2007).

79. J. Yu, et al., Human Induced Pluripotent Stem Cells Free of Vector and Transgene Sequences. *Science* (80-.). 324, 797-801 (2009).

80. F. R. Kreitzer, et al., A robust method to derive functional neural crest cells from human pluripotent stem cells. *Am. J. Stem Cells* 2, 119-31 (2013).

81. G. Chen, et al., Chemically defined conditions for human iPSC derivation and culture. *Nat. Methods* 8, 424-9 (2011).

82. A. Dobin, et al., STAR: Ultrafast universal RNA-seq aligner. *Bioinformatics* 29, 15-21 (2013).

83. Y. Liao, G. K. Smyth, W. Shi, FeatureCounts: An efficient general purpose program for assigning sequence reads to genomic features. *Bioinformatics* 30, 923-930 (2014).
84. R. D. Hodge, et al., Conserved cell types with divergent features in human versus mouse cortex. *Nature* 573, 61-68 (2019).
85. D. Polioudakis, et al., A Single-Cell Transcriptomic Atlas of Human Neocortical Development during Mid-gestation. *Neuron* 103, 785-801.e8 (2019).
86. G. La Manno, et al., Molecular Diversity of Midbrain Development in Mouse, Human, and Stem Cells. *Cell* 167, 566-580.e19 (2016).
87. X. Han, et al., Construction of a human cell landscape at single-cell level. *Nature* 581, 303-309 (2020).
88. S. Zhong, et al., Decoding the development of the human hippocampus. *Nature* 577, 531-536 (2020).
89. M. I. Love, W. Huber, S. Anders, Moderated estimation of fold change and dispersion for RNA-seq data with DESeq2. *Genome Biol.* 15, 550 (2014).
90. A. Subramanian, et al., Gene set enrichment analysis: A knowledge-based approach for interpreting genome-wide expression profiles. *Proc. Natl. Acad. Sci.* 102, 15545-15550 (2005).
91. M. Kanehisa, S. Goto, KEGG: kyoto encyclopedia of genes and genomes. *Nucleic Acids Res.* 28, 27-30 (2000).
92. M. Ashburner, et al., Gene ontology: tool for the unification of biology. The Gene Ontology Consortium. *Nat. Genet.* 25, 25-9 (2000).
93. G. La Manno, et al., Molecular architecture of the developing mouse brain. *Nature* 596, 92-96 (2021).
94. F. A. Wolf, P. Angerer, F. J. Theis, SCANPY: large-scale single-cell gene expression data analysis. *Genome Biol.* 19, 15 (2018).
95. M. E. Floy, et al., Developmental lineage of human pluripotent stem cell-derived cardiac fibroblasts affects their functional phenotype. *FASEB* J. 35, 1-23 (2021).
96. B. Langmead, S. L. Salzberg, Fast gapped-read alignment with Bowtie 2. *Nat. Methods* 9, 357-359 (2012).
97. H. M. Amemiya, A. Kundaje, A. P. Boyle, The ENCODE Blacklist: Identification of Problematic Regions of the Genome. *Sci. Rep.* 9, 1-5 (2019).
98. Y. Zhang, et al., Model-based analysis of ChIP-Seq (MACS). *Genome Biol.* 9 (2008).
99. G. Yu, L. G. Wang, Q. Y. He, ChIP seeker: An R/Bioconductor package for ChIP peak annotation, comparison and visualization. *Bioinformatics* 31, 2382-2383 (2015).
100. F. Ramirez, et al., deepTools2: a next generation web server for deep-sequencing data analysis. *Nucleic Acids Res.* 44, W160-W165 (2016).
101. P. Machanick, T. L. Bailey, MEME-ChIP: Motif analysis of large DNA datasets. *Bioinformatics* 27, 1696-1697 (2011).
102. W. J. Kent, et al., The Human Genome Browser at UCSC. *Genome Res.* 12, 996-1006 (2002).
103. J. L. Everson, et al., Sonic hedgehog regulation of Foxf2 promotes cranial neural crest mesenchyme proliferation and is disrupted in cleft lip morphogenesis. *Development* 144, 2082-2091 (2017).

We claim:

1. A method of producing a population of NOTCH3$^+$ PDGFRβ$^+$RGS5$^+$ brain mural cells comprising:

a) culturing human pluripotent cells (hPSCs) in E6-CSFD medium for about 15 days to produce p75-NGFR$^+$ HNK-1$^+$ neural crest stem cells (NCSCs), b) sorting p75-NGFR$^+$ cells and re-plating the p75-NGFR$^+$ cells of step (a) to produce a population of p75-NGFR$^+$ NCSCs;

c) activating Notch signaling in the sorted p75-NGFR$^+$ HNK-I$^+$ NCSCs of step (b); and d) culturing the cells of step (c) in serum free medium for a sufficient time to differentiate NOTCH3$^+$PDGFRβ$^+$ RGS5$^+$ brain mural cells, wherein the serum free medium comprises a base media supplemented with a GSK3β inhibitor, a TGFβ inhibitor, a BMP type I receptor inhibitor, and FGF2.

2. The method of claim 1, wherein step (c) comprises:

(i) introducing an exogenous construct encoding at least an intracellular domain of a Notch receptor and capable of expressing the intracellular domain within the NC cell;

(ii) culturing the NC cells in serum free medium in the presence of Notch ligands;

(iii) co-culturing the NC cells with cells overexpressing Notch ligands or (iv) activating the Notch pathway using a Notch activation factor.

3. The method of claim 2, wherein step (c) comprises step (i) and wherein the exogenous construct is a viral vector.

4. The method of claim 2, wherein step (c) comprises step (i) and wherein the intracellular domain is or comprises SEQ ID NO:2.

5. The method of claims 2, wherein step (c) comprises step (i) and wherein the intracellular domain is or comprises SEQ ID NO:4.

6. The method of claim 2, wherein step (c) comprises (ii) wherein the NC are contacted with beads coated with Notch ligands or Notch stimulating factor or with Notch coated plates.

7. The method of claim 1, wherein step (d) is culturing the Notch activated NCSCs for at least 6 days.

8. The method of claim 1, wherein the mural cells further express one or more of the markers selected from Tbx2, HEYL, RGS5, FOXS1, and endogenous Notch3.

9. The method of claim 1, wherein the mural cells further express one or more of the markers selected from KCNJ8, ABCC9, and HIGD1B.

10. The method of claim 1, wherein the method produces a cell population that is at least 90% NOTCH3$^{+}$PDGFR$\beta^{+}$ RGS5$^{+}$ brain mural cells.

11. The method of claim 2, wherein the Notch receptor is Notch 3.

12. The method of claim 1, wherein the population of cells produced is NOTCH3$^{+}$PDGFR$\beta^{+}$RGS5$^{+}$ brain mural cells which are able to double at least 5 times in culture and maintain expression of NOTCH3, PDGFRβ, and RGS5 within the cells.

13. The method of claim 12, wherein the cells further express one or more markers selected from FOXS1, TBX2, ABCC9, KCNJ8 and HEYL while cultured.

14. A population of NOTCH3$^{+}$PDGFR$\beta^{30}$ RGS5+ brain mural cells produced by the method of claim 1.

15. The NOTCH3$^{+}$PDGFR$\beta^{+}$RGS5$^{+}$ brain mural cells population of claim 14, wherein the population is capable of differentiating further into brain pericytes and vascular smooth muscle cells.

16. A BBB model, wherein the model comprises the population of NOTCH3$^{+}$PDGFR$\beta^{+}$RGS5$^{+}$ brain mural cells of claim 1, wherein the BBB model is capable of forming tight junctions.

17. The population of claim 14, wherein the population of NOTCH3$^{+}$PDGFR$\beta^{+}$RGS5$^{+}$ brain mural cells expresses KCNJ8 and/or ABCC9 and/or wherein the population forms a functional KATP channel.

* * * * *